United States Patent
Raichman

(10) Patent No.: US 12,178,245 B2
(45) Date of Patent: Dec. 31, 2024

(54) SMOKING DEVICE

(71) Applicant: Altria Client Services LLC, Richmond, VA (US)

(72) Inventor: Yossef Raichman, Herzliya (IL)

(73) Assignee: Altria Client Services LLC, Richmond, VA (US)

( * ) Notice: Subject to any disclaimer, the term of this patent is extended or adjusted under 35 U.S.C. 154(b) by 1032 days.

(21) Appl. No.: 16/333,446

(22) PCT Filed: Sep. 14, 2017

(86) PCT No.: PCT/IL2017/051041
§ 371 (c)(1),
(2) Date: Mar. 14, 2019

(87) PCT Pub. No.: WO2018/051346
PCT Pub. Date: Mar. 22, 2018

(65) Prior Publication Data
US 2019/0208823 A1    Jul. 11, 2019

Related U.S. Application Data

(60) Provisional application No. 62/525,773, filed on Jun. 28, 2017, provisional application No. 62/500,509, (Continued)

(51) Int. Cl.
*A24F 40/42* (2020.01)
*A24F 40/40* (2020.01)
(Continued)

(52) U.S. Cl.
CPC .............. *A24F 40/42* (2020.01); *A24F 40/40* (2020.01); *A24F 40/46* (2020.01); *A24F 40/50* (2020.01);
(Continued)

(58) Field of Classification Search
CPC .......... A24F 40/42; A24F 40/50; A24F 40/40; A24F 40/46; A24F 40/57; A24F 40/20;
(Continued)

(56) References Cited

U.S. PATENT DOCUMENTS 6,040,560 A    3/2000  Fleischhauer et al.
8,897,628 B2   11/2014 Conley et al.
(Continued)

FOREIGN PATENT DOCUMENTS

CA    2937980 A1   8/2015
CA    2953069 A2   1/2016
(Continued)

OTHER PUBLICATIONS

Office Action for Japanese Application No. 2019-572088 dated Mar. 8, 2022 and English translation.
(Continued)

*Primary Examiner* — Shawntina T Fuqua
(74) *Attorney, Agent, or Firm* — Harness, Dickey & Pierce, P.L.C.

(57) ABSTRACT

Apparatus and methods are described for use with a portion of plant material that includes at least one active ingredient. A vaporizing unit includes a heating element configured to heat the plant material, and a sensor configured to detect an indication of airflow rate through the vaporizing unit. Control circuitry is configured to receive an indication of the airflow rate through the vaporizing unit, and, in response thereto, to determine a smoking profile that is desired by the user. The control circuitry drives the heating element to vaporize the active ingredient of the plant material by heating the plant material according to the determined smoking profile. The control circuitry dynamically updates
(Continued)

the smoking profile in response to changes in airflow rate over the course of a smoking session. Other applications are also described.

22 Claims, 19 Drawing Sheets

Related U.S. Application Data filed on May 3, 2017, provisional application No. 62/453,544, filed on Feb. 2, 2017, provisional application No. 62/394,243, filed on Sep. 14, 2016.

(51) Int. Cl.

| | | |
|---|---|---|
| *A24F 40/46* | (2020.01) | |
| *A24F 40/50* | (2020.01) | |
| *A24F 40/57* | (2020.01) | |
| *A61K 9/00* | (2006.01) | |
| *A61K 31/05* | (2006.01) | |
| *A61K 31/352* | (2006.01) | |
| *A61K 36/185* | (2006.01) | |
| *A61M 11/04* | (2006.01) | |
| *A61M 15/00* | (2006.01) | |
| *A61M 15/06* | (2006.01) | |
| *A61P 1/08* | (2006.01) | |
| *A61P 11/06* | (2006.01) | |
| *A61P 25/08* | (2006.01) | |
| *A61P 25/18* | (2006.01) | |
| *A61P 25/30* | (2006.01) | |
| *A61P 25/36* | (2006.01) | |
| *A61P 27/06* | (2006.01) | |
| *A61P 29/00* | (2006.01) | |
| *A61P 43/00* | (2006.01) | |
| *A24F 40/20* | (2020.01) | |
| *A24F 40/60* | (2020.01) | |
| *A24F 40/95* | (2020.01) | |
| *A61M 16/00* | (2006.01) | |

(52) U.S. Cl.
CPC .............. *A24F 40/57* (2020.01); *A61K 9/007* (2013.01); *A61K 31/05* (2013.01); *A61K 31/352* (2013.01); *A61K 36/185* (2013.01); *A61M 11/042* (2014.02); *A61M 15/00* (2013.01); *A61M 15/003* (2014.02); *A61M 15/06* (2013.01); *A61P 1/08* (2018.01); *A61P 11/06* (2018.01); *A61P 25/08* (2018.01); *A61P 25/18* (2018.01); *A61P 25/30* (2018.01); *A61P 25/36* (2018.01); *A61P 27/06* (2018.01); *A61P 29/00* (2018.01); *A61P 43/00* (2018.01); *A24F 40/20* (2020.01); *A24F 40/60* (2020.01); *A24F 40/95* (2020.01); *A61M 15/002* (2014.02); *A61M 15/0021* (2014.02); *A61M 2016/0024* (2013.01); *A61M 2205/3334* (2013.01); *A61M 2205/3368* (2013.01); *A61M 2205/8206* (2013.01)

(58) Field of Classification Search
CPC ....... A24F 40/60; A24F 40/95; A61M 11/042; A61M 2205/3334; A61M 2205/3368; A61M 2205/8206; A61M 2205/07; A61M 2205/10; A61M 2205/18; A61M 2205/273; A61M 2205/3584; A61M 2205/3592; A61M 2205/0227; A61M 2205/0238; A61M 2205/3305; A61M 2205/3317; A61M 2205/362; A61M 2205/3653; A61M 2205/368; A61M 2205/505; A61M 2205/581; A61M 2205/582; A61M 2205/6027; A61M 2205/6036; A61M 2205/6054; A61M 2205/6072; A61M 2205/6081; A61M 2205/8262; A61M 2205/8237; A61M 2209/01; A61M 2209/086; A61M 19/00; A61M 15/00; A61M 15/003; A61M 15/06; A61M 15/0021; A61M 15/0065; A61M 15/0041; A61M 15/0006; A61M 15/0063; A61M 15/0045; A61M 2016/0024; A61M 2016/0021; A61K 9/0007; A61K 31/05; A61K 31/352; A61K 36/185; A61P 1/08; A61P 11/06; A61P 25/08; A61P 25/18; A61P 25/30; A61P 25/36; A61P 27/06; A61P 29/00; A61P 43/00

See application file for complete search history.

(56) References Cited

U.S. PATENT DOCUMENTS

| | | | |
|---|---|---|---|
| 2002/0092521 A1* | 7/2002 | Sullivan | A61M 15/0033 128/200.24 |
| 2009/0133691 A1 | 5/2009 | Yamada et al. | |
| 2009/0301471 A1* | 12/2009 | Stirzel | A61M 11/041 128/200.14 |
| 2009/0302019 A1 | 12/2009 | Selenski et al. | |
| 2012/0046352 A1 | 2/2012 | Hospodor | |
| 2013/0081623 A1 | 4/2013 | Buchberger | |
| 2013/0298905 A1 | 11/2013 | Levin et al. | |
| 2014/0299141 A1* | 10/2014 | Flick | A24F 40/50 219/494 |
| 2014/0366898 A1* | 12/2014 | Monsees | A24F 40/30 131/329 |
| 2014/0373857 A1 | 12/2014 | Steinberg | |
| 2015/0105455 A1 | 4/2015 | Bjorncrantz | |
| 2015/0128976 A1* | 5/2015 | Verleur | A24F 40/50 131/329 |
| 2015/0136158 A1 | 5/2015 | Stevens et al. | |
| 2015/0208727 A1 | 7/2015 | Kuczaj | |
| 2015/0216237 A1 | 8/2015 | Wensley et al. | |
| 2015/0223292 A1* | 8/2015 | Duffield | A61L 9/037 219/634 |
| 2015/0305410 A1 | 10/2015 | Liu | |
| 2016/0021930 A1 | 1/2016 | Minskoff et al. | |
| 2016/0150825 A1 | 6/2016 | Mironov et al. | |
| 2016/0219938 A1 | 8/2016 | Mamoun et al. | |
| 2016/0271347 A1 | 9/2016 | Raichman | |
| 2016/0309789 A1 | 10/2016 | Thomas, Jr. | |
| 2016/0310684 A1 | 10/2016 | McCullough | |
| 2016/0331913 A1 | 11/2016 | Bourque | |
| 2016/0338407 A1* | 11/2016 | Kerdemelidis | A24F 40/60 |
| 2017/0095624 A1* | 4/2017 | Davidson | A61P 1/14 |
| 2017/0127727 A1 | 5/2017 | Davidson et al. | |
| 2017/0273357 A1 | 9/2017 | Barbuck | |
| 2022/0022537 A1* | 1/2022 | Murray | A24F 40/485 |
| 2022/0338549 A1* | 10/2022 | Batista | A24F 40/50 |
| 2024/0188637 A1* | 6/2024 | Kim | A24F 40/485 |

FOREIGN PATENT DOCUMENTS

| | | | | |
|---|---|---|---|---|
| CA | 2980260 A1 | 9/2016 | | |
| CN | 103932406 A | 7/2014 | | |
| EP | 2399636 A1 | 12/2011 | | |
| EP | 3160552 A1 | 5/2017 | | |
| EP | 3868231 A2 | 8/2021 | | |
| WO | WO-2011/033396 A2 | 3/2011 | | |
| WO | WO-2013/060781 A1 | 5/2013 | | |
| WO | WO-2014/040988 A2 | 3/2014 | | |
| WO | WO-2014139611 A1 * | 9/2014 | ............ | A24F 47/00 |
| WO | 2015/116934 A1 | 8/2015 | | |
| WO | WO-2015/117704 A1 | 8/2015 | | |
| WO | WO-2016/001923 A2 | 1/2016 | | |
| WO | WO-2016/001925 A1 | 1/2016 | | |

(56) References Cited

FOREIGN PATENT DOCUMENTS

| WO | WO-2016/005602 A1 | 1/2016 |
| WO | WO-2016/096927 A1 | 6/2016 |
| WO | WO-2016/147188 A1 | 9/2016 |
| WO | WO-2016/162446 A1 | 10/2016 |

OTHER PUBLICATIONS

European Office Action dated May 3, 2021, issued in corresponding European Application No. 17850419.7.
Extended European Search Report dated Apr. 1, 2021, issued in corresponding European Patent Application No. 18823783.8.
International Search Report for corresponding PCT/IL2017/051041 application dated Dec. 21, 2017.
Office Action for corresponding U.S. Appl. No. 15/845,501 dated Sep. 24, 2019.
U.S. Appl. No. 16/801,780, filed Feb. 26, 2020.
U.S. Appl. No. 16/801,898, filed Feb. 26, 2020.
U.S. Appl. No. 15/845,501, filed Dec. 18, 2017.
International Preliminary Report on Patentability Chapter I issued on Dec. 31, 2019 in International Application No. PCT/US2018/038156.
International Search Report and Written Opinion for corresponding Application No. PCT/US18/38156 dated Aug. 30, 2018.
International Preliminary Report on Patentability Chapter I issued on Mar. 19, 2019 in International Application No. PCT/IL2017/051041.
Non-Final Office Action issued Feb. 19, 2019 in U.S. Appl. No. 15/845,501.
Notice of Allowance issued Mar. 31, 2020 in U.S. Appl. No. 15/845,501.
Extended European Search Report dated Apr. 17, 2020 for corresponding European Application No. 17850419.7.
Office Action dated Aug. 9, 2022, issued in corresponding U.S. Appl. No. 16/801,780.
Examination Report dated Jul. 14, 2022, issued in corresponding Australian Patent Application No. 2017328499.
Office Action dated Nov. 6, 2022 issued in related Israeli Patent Application No. 271521.
Notice of Allowance dated Nov. 30, 2022, issued in corresponding U.S. Appl. No. 16/801,780.
Notice of Allowance dated Nov. 30, 2022, issued in corresponding U.S. Appl. No. 16/801,898.
T. Veress et al., 'Determination of cannabinoid acids by high-performance liquid chromatography of their neutral derivatives formed by thermal decarboxylation' *Journal of Chromatography*, vol. 520, 1990, pp. 339-347.
Franz E. Dussy et al., 'Isolation of $\Delta^9$-THCA-A from hemp and analytical aspects concerning the determination of $\Delta^9$-THC in cannabis products' *Forensic Science International*, vol. 149, 2005, pp. 3-10.
Notice of Allowance dated Mar. 8, 2023 issued in related U.S. Appl. No. 16/801,898.
Notice of Allowance dated Mar. 16, 2023 issued in related U.S. Appl. No. 16/801,898.
Notice of Allowance dated Mar. 15, 2023 issued in related U.S. Appl. No. 16/916,573.
Notice of Allowance dated Mar. 20, 2023, issued in related U.S. Appl. No. 16/801,780.
Office Action, dated Oct. 26, 2023, issued in related Canadian Patent Application No. 3036636.
New Zealand Office Action, dated Mar. 22, 2024, issued in New Zealand Patent Application No. 792345.
New Zealand Office Action, dated Mar. 22, 2024, issued in New Zealand Patent Application No. 792339.
New Zealand Office Action, dated Mar. 22, 2024, issued in New Zealand Patent Application No. 751565.
New Zealand Office Action, dated Mar. 22, 2024, issued in New Zealand Patent Application No. 792346.
Office Action dated Jan. 24, 2024 issued in related Korean patent application No. 10-2020-7002439.
Office Action dated Feb. 6, 2024 issued in related Japanese patent application No. 2023-003336.
Extended European Search Report dated Jun. 28, 2024 issued in European patent application No. 24164935.9.
Decision of Refusal dated Aug. 20, 2024 issued in Japanese Patent Application No. 2023-003336.
Office Action dated Aug. 15, 2024, issued in Canadian Patent Application No. 3067581.
Examination Report dated Sep. 26, 2024 issued in New Zeland patent application No. 751565.
Examination Report dated Oct. 15, 2024 issued in New Zeland patent application No. 792346.

\* cited by examiner

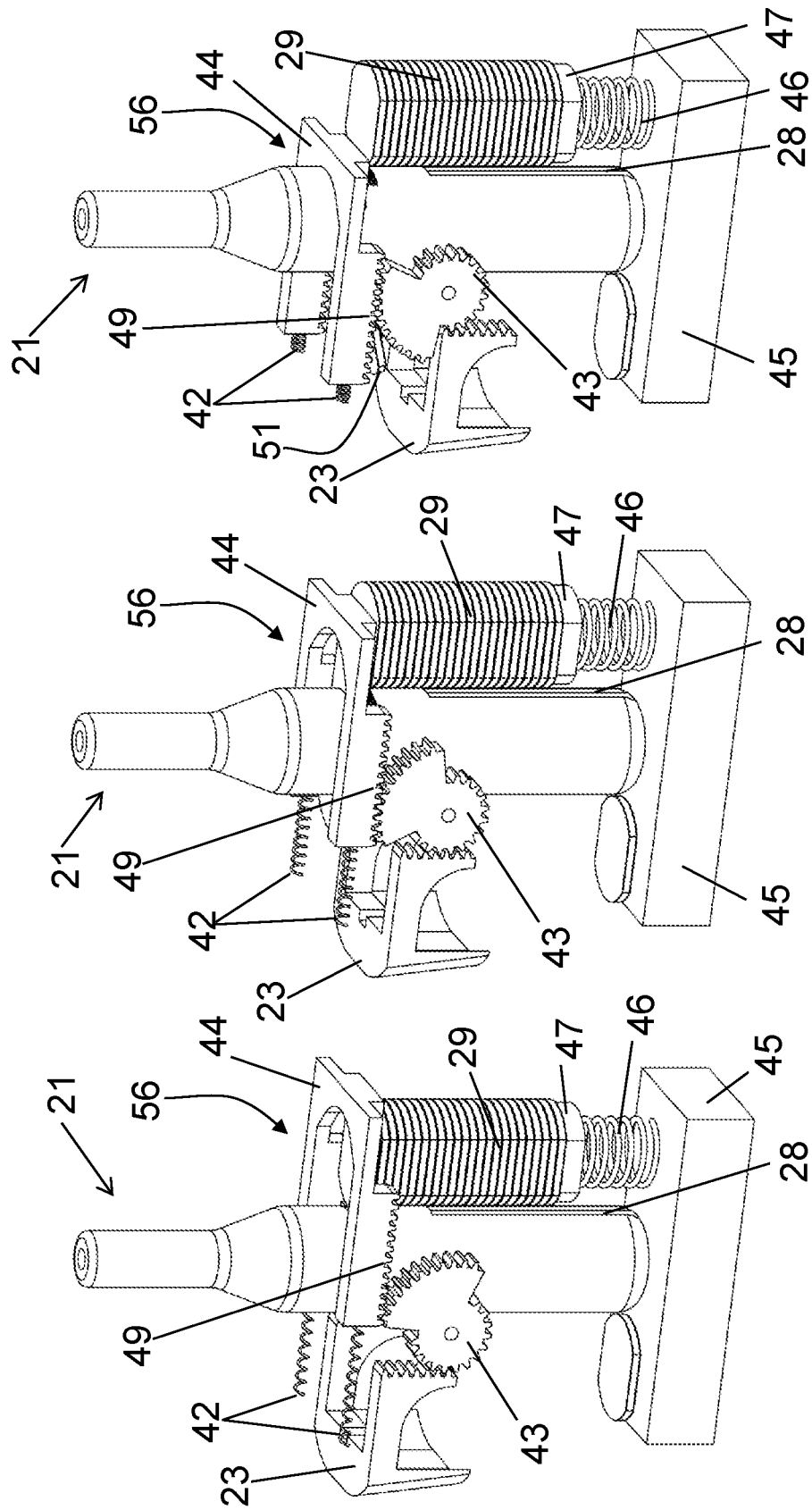

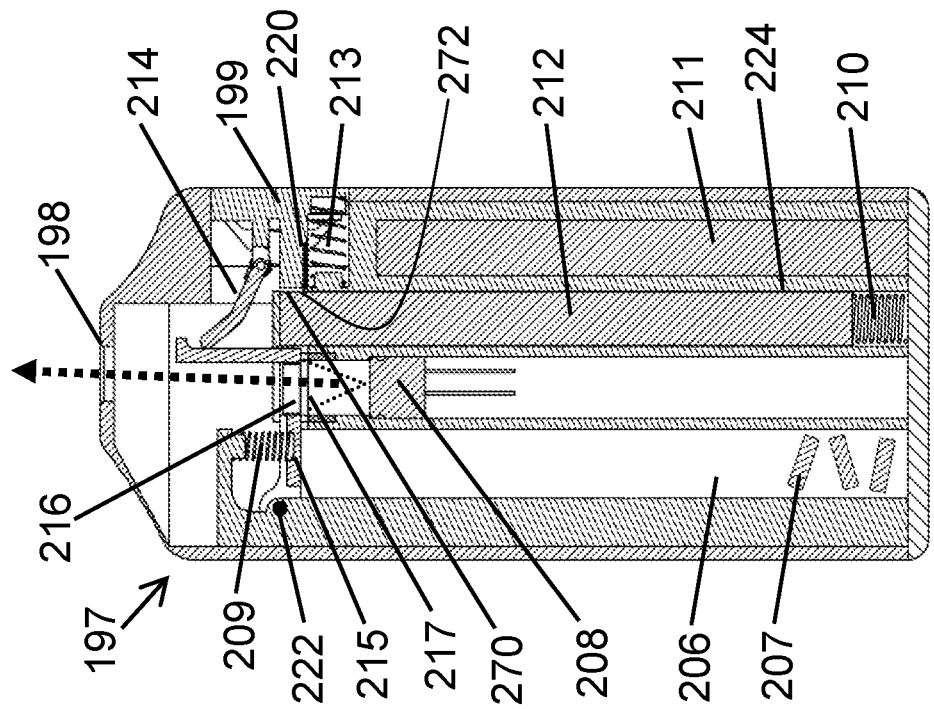
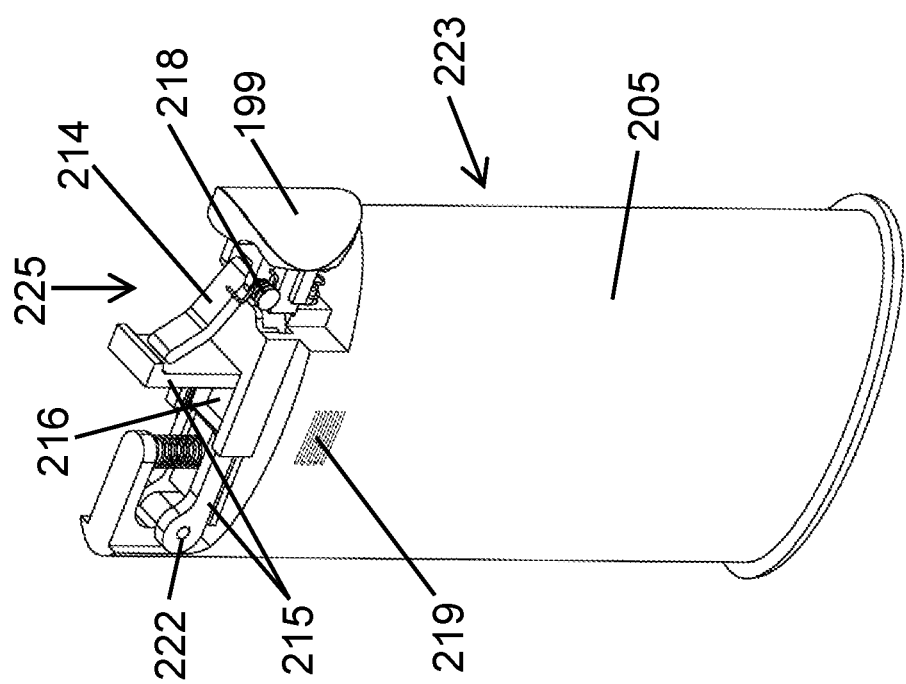
FIG. 16
FIG. 15

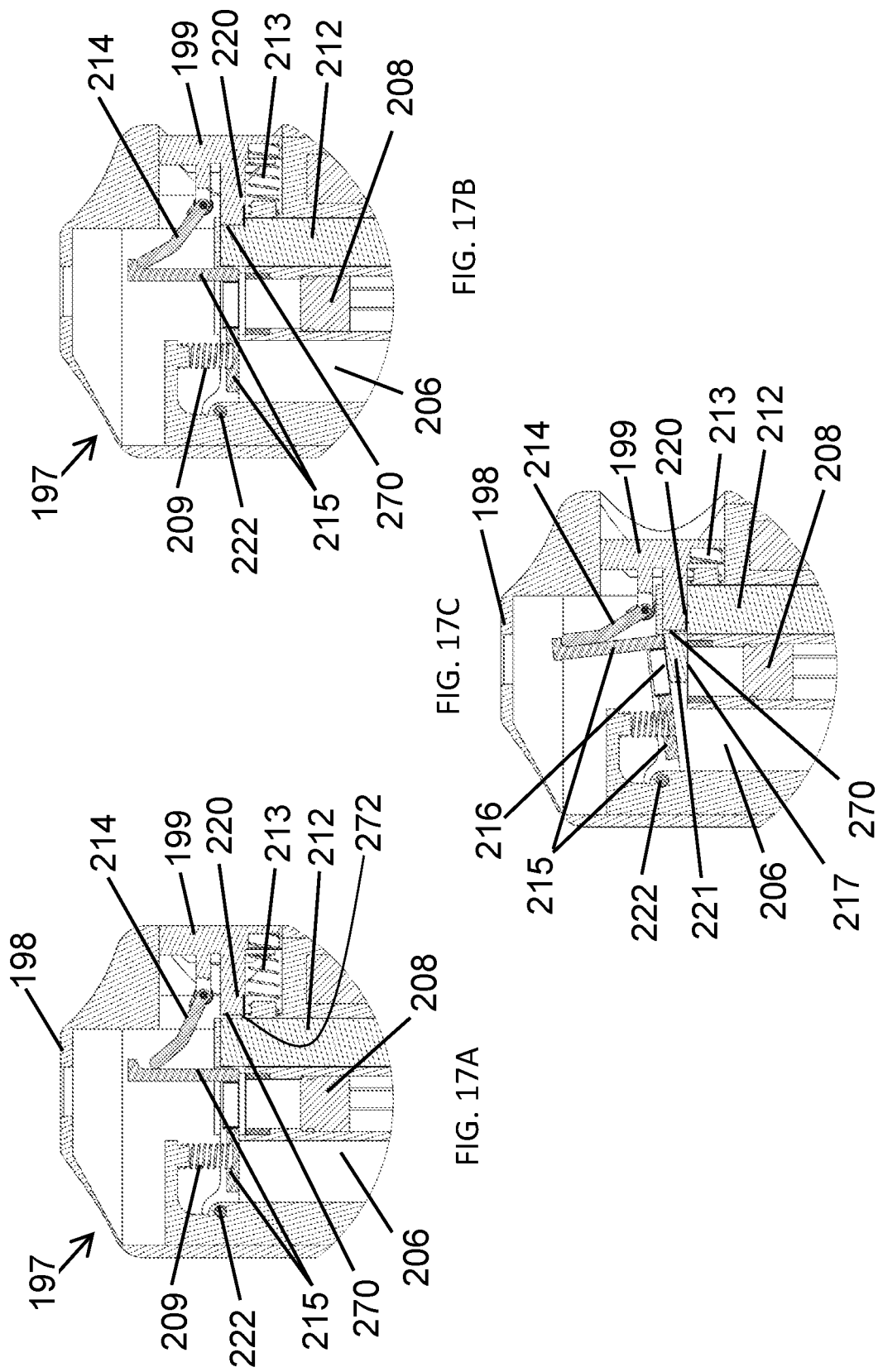

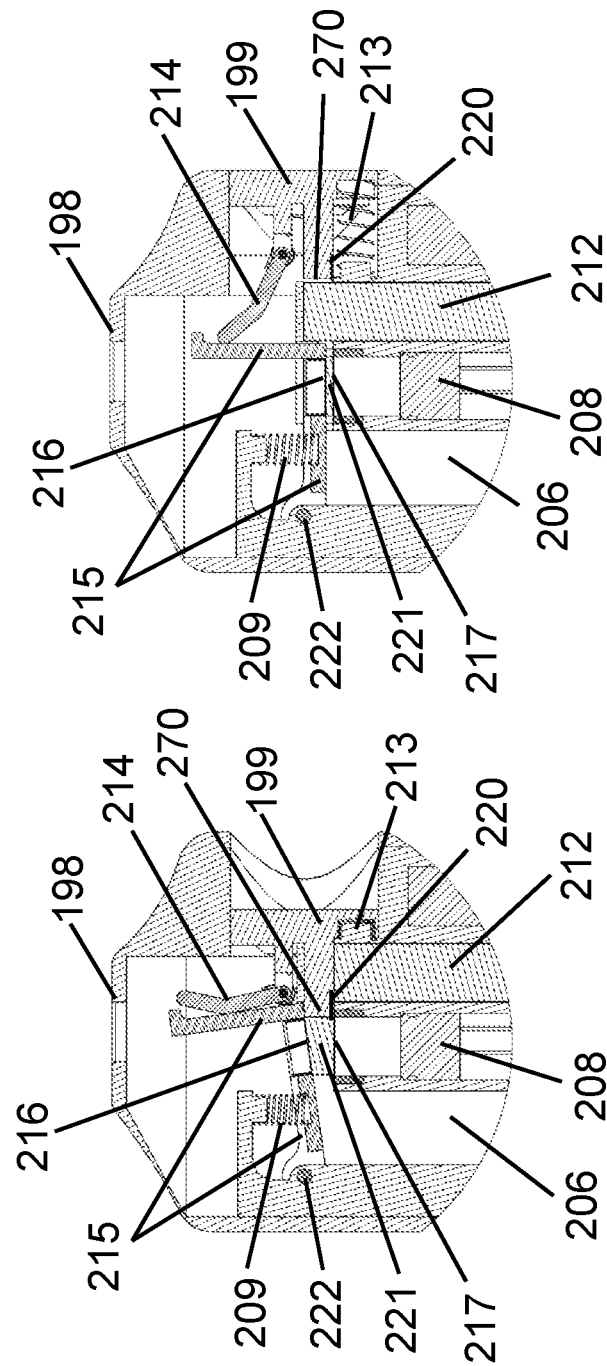

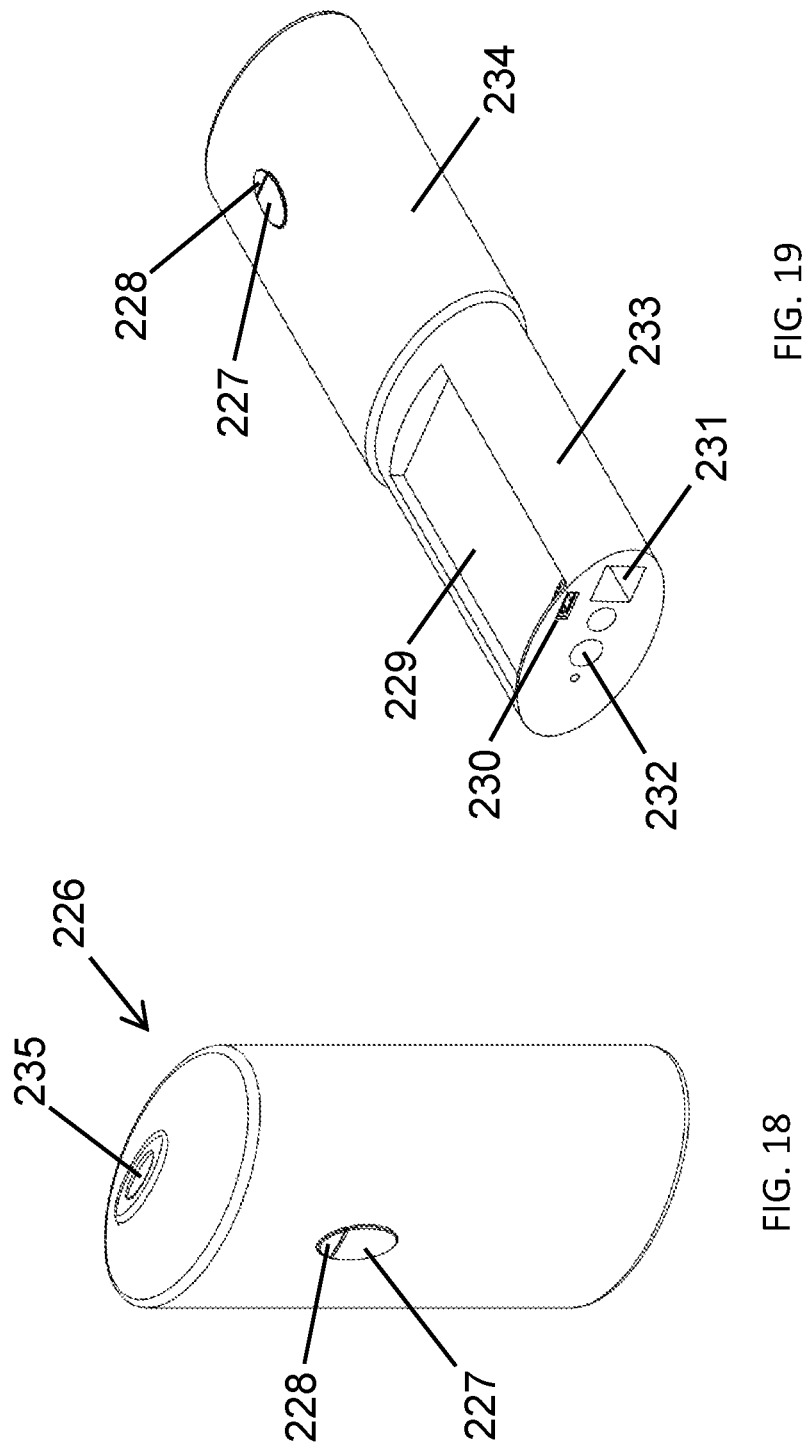

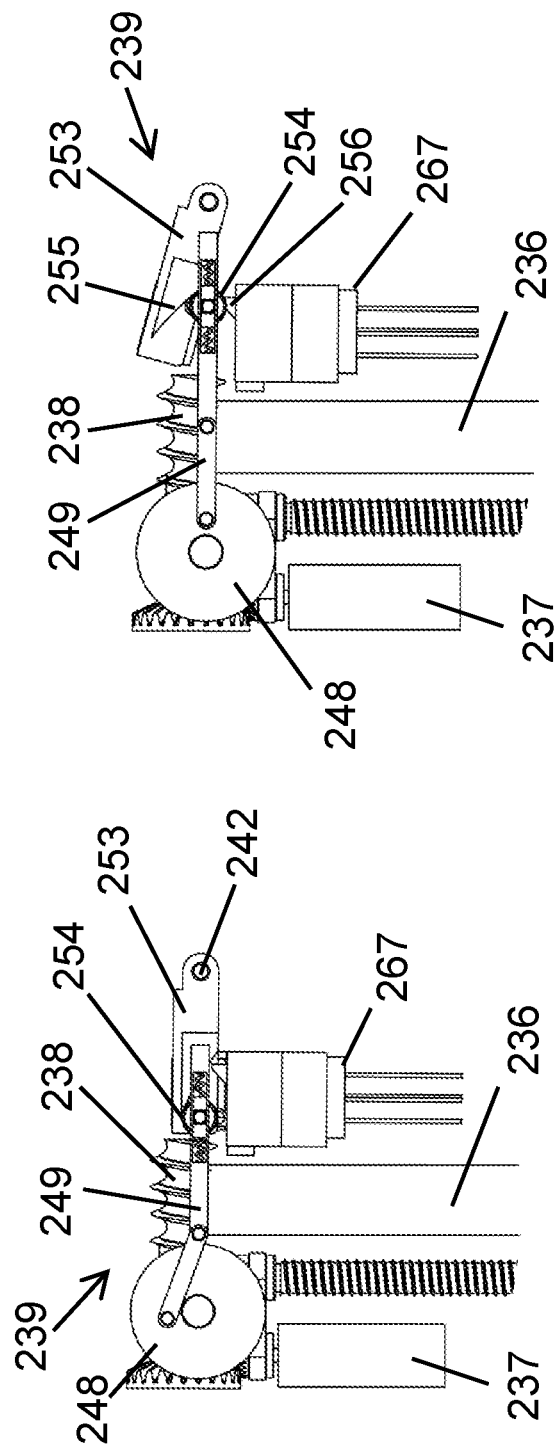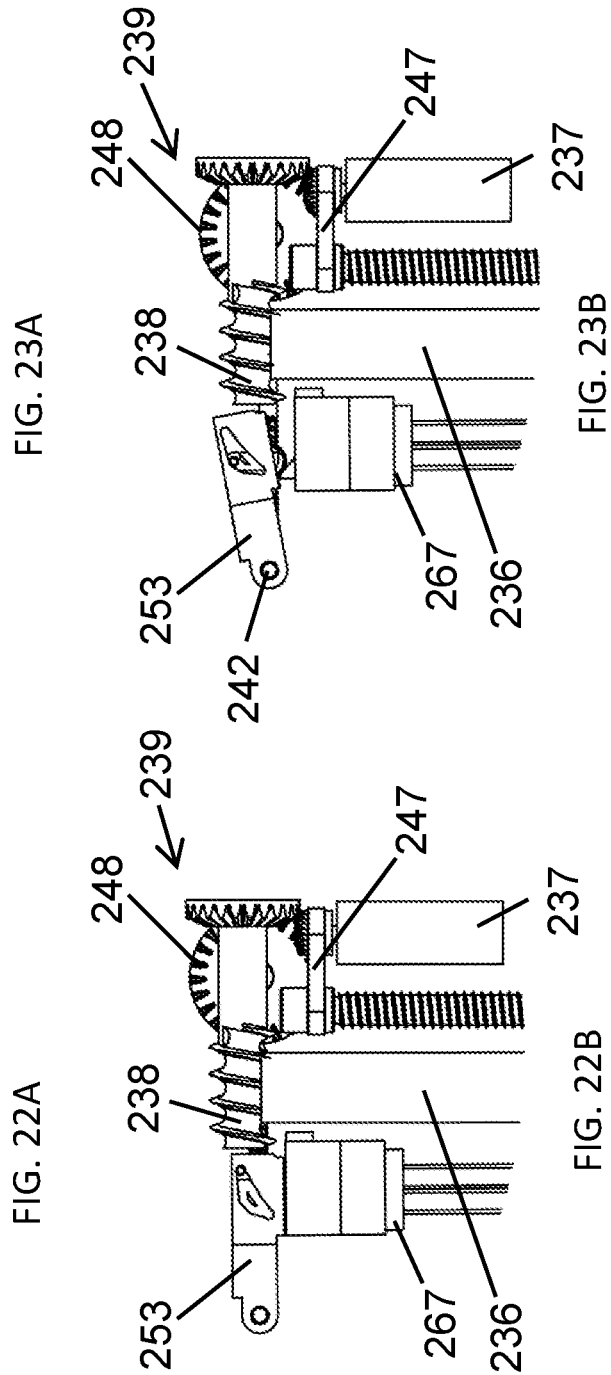
FIG. 22A
FIG. 22B
FIG. 23A
FIG. 23B

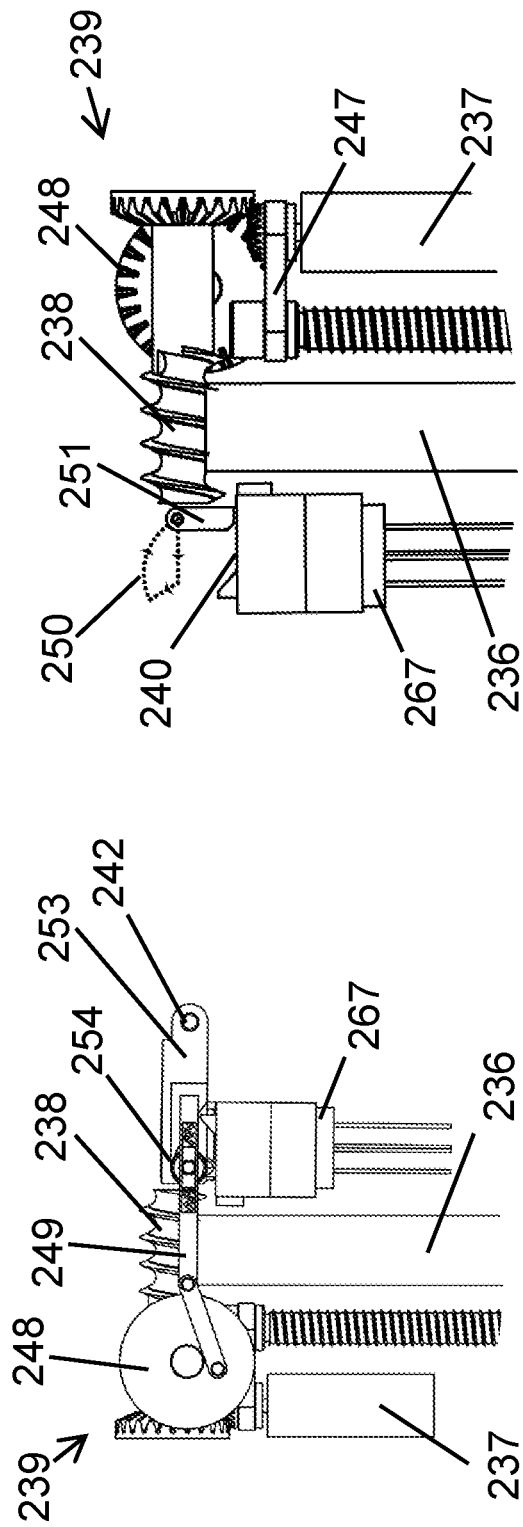
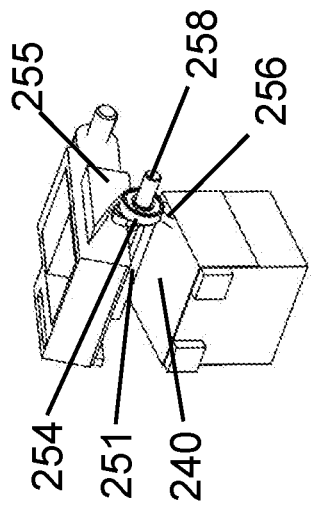
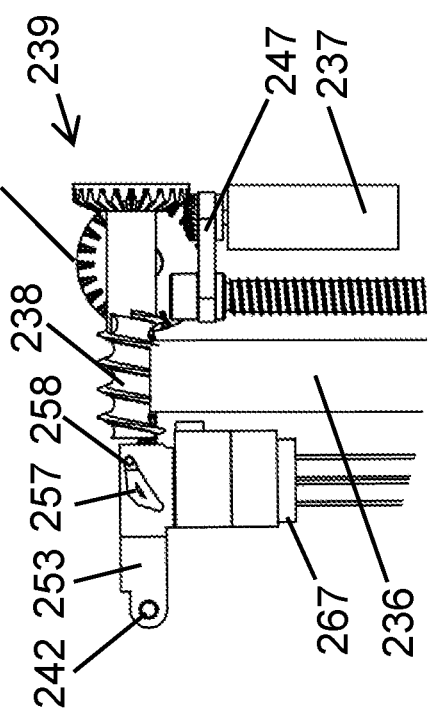
FIG. 25
FIG. 26
FIG. 24A
FIG. 24B

SMOKING DEVICE

CROSS-REFERENCE TO RELATED APPLICATIONS

This application is a national phase under 35 U.S.C. § 371 of PCT International Application No. PCT/IL2017/051041 which has an International filing date of Sep. 14, 2017, which claims priority to U.S. Provisional Application Nos. 62/394,243, filed Sep. 14, 2016, 62/453,544, filed Feb. 2, 2017, 62/500,509, filed May 3, 2017 and 62/525,773, filed Jun. 28, 2017, the entire contents of each of which are hereby incorporated by reference.

FIELD OF EMBODIMENTS OF THE INVENTION

Some applications of the present invention generally relate to a smoking apparatus. Specifically, some applications of the present invention relate to smoking devices for the delivery of an active ingredient to a subject.

BACKGROUND

Mouthfullness is an attribute that smokers refer to that relates to the texture and feel of tobacco smoke in the mouth. In order to reproduce the taste and feel of tobacco smoke, electronic cigarettes typically heat tobacco plant material or other non-liquid materials containing active ingredients (e.g., nicotine). The active ingredients are released due to the application of heat on the material.

Medical use of *cannabis* and its constituent cannabinoids, such as tetrahydrocannabinol (THC) and cannabidiol (CBD), has a long history. In modern times, *cannabis* is used by patients suffering from AIDS, or undergoing chemotherapy treatment, in order to relieve nausea and vomiting associated with their conditions. *Cannabis* is also used in a medicinal manner in order to provide pain relief, to treat muscle spasticity, and to stimulate appetite.

Medicinal *cannabis* can be administered using a variety of methods, including vaporizing or smoking dried buds, eating extracts, taking capsules or using oral sprays. The legality of medical use of *cannabis* varies internationally. However, even in countries in which the medical use of *cannabis* is legal, the provision of *cannabis* to such users is highly regulated, and it is the case that in almost all Western countries, recreational use of *cannabis* is illegal.

SUMMARY OF EMBODIMENTS

In accordance with some applications of the present invention, a smoking device is used to vaporize the active ingredient of a material, such as a plant material, by heating the material. For example, the smoking device may be used to vaporize tobacco, *cannabis*, and/or other plant or chemical substances that contain an active ingredient (such as nicotine, tetrahydrocannabinol (THC) and/or cannabidiol (CBD)) that becomes vaporized upon the substance being heated. In general, the material containing the active ingredient is described herein as being a plant material. However, the scope of the present application includes using a non-plant material, such as synthetic materials that contain active ingredients, as an alternative or in addition to the plant material.

Typically, the smoking device includes a vaporizing unit, and a reloading unit. The reloading unit houses a plurality of capsules, each of the capsules including a given amount of a plant material that contains an active ingredient. For some applications, the reloading unit is shaped to define first and second receptacles, each of which is shaped to house the plurality of capsules in stacked configurations. While each of the capsules is disposed at a vaporization location within the vaporizing unit, a heating element causes the active ingredient of the plant material within the capsule to become at least partially vaporized by individually heating the capsule. For some applications, the heating element includes one or more electrodes that heat the capsule via resistive heating, by driving a current into a portion of the capsule (e.g., into a metallic mesh of the capsule). Alternatively or additionally, a current is driven into an internal heating element that is housed within the vaporizing unit, and the internal heating element heats the capsule via conductive heating. Typically, a capsule-loading mechanism of the reloading unit individually transfers each of the capsules from the first receptacle in the reloading device to the vaporization location in the vaporizing unit and from the vaporization location to the second receptacle within the reloading unit. For some applications, the smoking device includes the vaporizing unit in the absence of the reloading unit. For example, the vaporizing unit may be configured such that a user can insert individual capsules into the vaporizing unit, and can then use the vaporizing unit to vaporize the active ingredient of the plant material.

For some applications, the vaporizing unit of the smoking device is configured such that various different types of capsules can be used with the vaporizing unit. For example, respective types of capsules may contain different quantities of plant material, plant material containing different amount of active ingredients, and/or different types of plant materials. Alternatively or additionally, respective types of capsules may have respective characteristics, e.g., respective flavors, strengths, richnesses, active ingredients, etc. For some applications, control circuitry of the vaporizing unit is configured to adjust a heating profile of the capsules to the capsule type that is currently being heated. For some such applications, the control circuitry implements an automatic capsule classification procedure, in accordance with which the control circuitry automatically classifies the capsule that is currently being heated as a given type of capsule, and designates a capsule heating profile accordingly.

Typically, the vaporizing unit is configured to replicate the responses of a traditional combustible cigarette to the manner in which a smoker smokes the cigarette. For example, when a traditional combustion cigarette is smoked, the cigarette undergoes an increased heating and burning rate in response to the smoker inhaling more strongly, and the resultant increased airflow through the cigarette. For some applications, in order to replicate this effect, the vaporizing unit applies a variable-temperature heating process to the plant material, for example, in the following manner. Typically, in response to receiving a first input at the vaporizing unit, the heating process is initiated and the plant material is heated above ambient temperature. An indication of the airflow rate through the vaporizing unit (e.g., the airflow rate through the capsule is which the plant material is disposed) is then measured. For example, the airflow rate may be measured directly by an airflow or pressure gauge. Alternatively or additionally, an indication of the airflow rate may be measured indirectly, by detecting an indication of the temperature of the plant material, e.g., by measuring the temperature of the capsule using a temperature sensor. For some applications, a temperature sensor is used that is configured to measure the temperature of the capsule without drawing heat from the capsule, as described in further detail hereinbelow. By measuring the temperature of the capsule in this manner, the measured temperature is typically more accurate than is the temperature sensor were to measure the temperature of the capsule in manner that draws heat from the capsule, ceteris paribus. Furthermore, the temperature sensor typically has a "near zero" response time, such that the control circuitry is able to measure changes in temperature due to changes in airflow, and respond to such changes in the manner described hereinbelow, effectively immediately with respect to the perception of the user. For example, the temperature sensor may be configured to detect changes in temperature within 0.01 seconds, e.g., within 1 millisecond, of such changes. For some applications, by virtue of having such a temperature sensor, the control circuitry is configured to respond to airflow-induced changes in temperature within 0.01 seconds, e.g., within 1 millisecond, of such changes.

Since the plant material is heated above ambient temperature, in the absence of heating being applied to the capsule, airflow through the capsule would cool the capsule by inducing forced heat transfer by convection. Thus, the induced heat transfer is indicative of the airflow rate through the capsule. Therefore, for some applications, based on the detected temperature indication, control circuitry of the vaporizing unit drives the heating element to maintain the temperature of the capsule constant, and measures the electrical power needed to maintain the temperature of the capsule constant. The electrical power that is needed to maintain the temperature of the capsule constant indicates the power required to overcome heat loss due to airflow through the capsule, and is therefore indicative of airflow through the capsule. Alternatively, the capsule is not maintained at a constant temperature, and the control circuitry determines the rate of airflow through the capsule based on a measured change in the temperature of the capsule. For example, the control circuitry may continue to heat the capsule at a fixed power, and measure the changes in temperature of the capsule. Typically, such changes in temperature are indicative of the airflow rate through the capsule. Alternatively, the control circuitry may stop heating the capsule when the capsule is at a given temperature, and measure changes in the temperature of the capsule. Typically, such changes in temperature are correlated with the rate of airflow through the capsule.

In response to the measured indication of the airflow rate, the control circuitry typically determines a smoking profile that is desired by the user and heats the plant material according to the determined smoking profile. A target temperature for the capsule is typically determined as a function of the measured indication of airflow rate. Typically, the target temperature increases as a function of an increase in airflow rate. Further typically, a maximal target temperature will be limited to a predefined maximum value in order not to exceed safety limits, and/or in order not to generate a bad taste due to overheating the plant material. In response to detecting an indication that the temperature of the capsule has reached the target temperature, further heating of the capsule is withheld. Subsequently, in response to receiving a further indication of the airflow rate, the control circuitry determines an updated smoking profile that is desired by the user. Typically, a new target vaporization temperature is defined according to the updated smoking profile. Typically, over the course of a smoking session, in response to receiving ongoing airflow measurements, the control circuitry dynamically determines smoking profiles that are desired by the user, and adjusts the heating of the capsule accordingly. For some applications, the target temperature to which the plant material is heated is dynamically updated in order to adjust the vaporization temperature and vaporization rate according to the desired smoking profile of the user. For some applications, the target temperature to which the plant material is heated is dynamically updated in a continuous manner. Alternatively, the target temperature to which the plant material is heated is dynamically updated on a puff-by-puff basis, i.e., with each inhalation of the user, the control circuitry calculates a target temperature to which the capsule should be heated for that inhalation. For some applications, each inhalation of the user is detected automatically by detecting airflow through the capsule, in accordance with the techniques described herein.

Typically, the control circuitry employs various heating profiles in order to simulate the behavior of a standard combustion cigarette, and in order to accommodate the user's indicated desired smoking profile, as well as the type of plant material that is used. For some applications, one or more of the following functionalities are provided by a vaporizing unit that dynamically adjusts the heating of the plant material in response to a measured airflow rate indication, as described hereinabove:

1) When smoking a traditional combustion cigarette, an increase in the user's inhalation rate increases generated smoke due to intensification of cigarette flame. In addition, the temperature of the inhaled smoke is typically greater. Therefore, for some applications, the target temperature to which the capsule is heated is correlated to airflow rate (which is indicative of user inhalation rate), in order to simulate the burning of a traditional cigarette as described above. As described hereinabove, typically the capsule is not heated above a predefined maximal temperature limit. Typically, the predefined maximal temperature limit is set such that the plant material is not heated to a temperature that is greater than the pyrolysis temperature of the plant material, and/or such that the plant material is not heated to a temperature that will produce smoke and/or a bad taste. By dynamically adjusting the target vaporization temperature as described hereinabove, the taste and "mouthfullness" of the generated vapors are adjusted according to user's individual taste and preferences. For example, users that prefer a long and slow inhalation will benefit from receiving a constant slow supply of the vaporized active ingredient, due to the relatively lower vaporization temperature that will be generated by the lower airflow rate of the slow inhalation. On the other end, users that prefer a faster and more intense release of the active ingredient will enjoy the higher rate of active ingredient vaporization rate that will result from the higher vaporization temperature to which the plant material is heated, due to their elevated inhalation airflow rate.

2) Dynamically adjusting the target temperature to which the plant material is heated as described hereinabove, may provide higher efficiency in the consumption rate of the plant material. For example, users that prefer taking several relatively short puffs will not suffer from loss of plant material between the short puffs, since the control circuitry will lower the target temperature to which the capsule is heated between the puffs.

3) Dynamically adjusting the target temperature to which the capsule is heated as described hereinabove, may reduce loss of active ingredient prior to the beginning of user inhalation. The lack of airflow prior to the user's inhalation will result in the target temperature to which the capsule is heated being relatively low, such as to reduce vaporization of active ingredient prior to user inhalation.

4) In some cases, a delivery of a constant dose of the active ingredient is desired on every puff. For a given arrangement of plant material, the mass of the active ingredient that is vaporized is a function of, at least, the temperature of the material and of the airflow rate through the material. For some applications, an airflow-related heating process is used as described hereinabove, and the control circuitry responds to the measured airflow indication, such as to deliver a constant dose of the active ingredient for each puff of the vaporizing unit. For example, a function may be used in accordance with which the vaporization temperature is reduced in response to the airflow increasing.

5) For some applications, the control circuitry additionally accounts for the amount of active ingredient that has already been vaporized from the portion of the plant material that is currently being heated (which may, for example, be a portion of the plant material that is disposed inside a capsule). For example, in some cases, based on the rates of airflow and temperatures that have already been applied to the capsule that is currently being heated, the control circuitry may determine an amount of the active ingredient that has already been vaporized. For some applications, the control circuitry determines the target temperature to which to heat the capsule, in response to the amount of active ingredient that has already been vaporized. For some applications, the control circuitry determines the target temperature to which to heat the capsule, in response to (a) the amount of active ingredient that has already been vaporized, as well as (b) the current measured airflow through the vaporizing unit (e.g., through the plant material that is being heated within the vaporizing unit). For example, for a given airflow rate, the control circuitry may heat the capsule to a greater temperature, the greater the amount of the active ingredient that has already been vaporized. This may be because, once a given amount of the active ingredient has already been vaporized from the plant material, the plant material may need to be heated to a greater temperature in order for the remaining active ingredient to be vaporized. For some applications, in response to determining that a given amount of the active ingredient has already been released from the plant material, the control circuitry may be configured to reduce the temperature of the plant material to a sub-vaporization temperature, such as to withhold additional vaporization of active ingredient.

It is noted that some applications of the present invention are described with reference to tobacco. However, the scope of the present invention includes using any material or substance that contains an active ingredient, mutatis mutandis.

In accordance with some applications of the present invention, a vaporizer is used to vaporize the active ingredient of a material, such as a plant material, by heating the material. For example, the vaporizer may be used to vaporize the constituent cannabinoids of *cannabis* (e.g., tetrahydrocannabinol (THC) and/or cannabidiol (CBD)). Alternatively or additionally, the vaporizer may be used to vaporize tobacco, and/or other plant or chemical substances that contain an active ingredient that becomes vaporized upon the substance being heated.

There is therefore provided, in accordance with some applications of the present invention, apparatus for use with a portion of plant material that includes at least one active ingredient, the apparatus including:
a vaporizing unit comprising:
a heating element configured to heat the plant material;
a sensor configured to detect an indication of airflow rate through the vaporizing unit that is generated by a user; and control circuitry configured:
to receive a first indication of the airflow rate through the vaporizing unit from the sensor;
in response to receiving the first indication of the airflow rate, to determine a first smoking profile that is desired by the user; and
to drive the heating element to vaporize the active ingredient of the plant material by heating the plant material according to the determined smoking profile; and
subsequently:
to receive a further indication of the airflow rate through the vaporizing unit from the sensor; and
in response to receiving the further indication of the airflow rate, to determine an updated smoking profile that is desired by the user; and
to drive the heating element to vaporize the active ingredient of the plant material by heating the plant material according to the determined updated smoking profile.

In some applications, the control circuitry:
is further configured to measure an amount of heating that the portion of the plant material has already undergone, and
is configured to drive the heating element to vaporize the active ingredient of the plant material by heating the plant material according to the determined smoking profile by determining a temperature to which to heat the portion of the plant material at least partially based upon the measured indication of the airflow rate and the amount of heating that the portion of the plant material has already undergone.

In some applications, the control circuitry is configured:
in response to receiving an indication of the airflow rate through the vaporizing unit from the sensor, to determine that the user is not inhaling from the vaporizing unit, and
in response thereto, to drive the heating element to reduce heating of the plant material, such that a temperature of the plant material decreases below a vaporization temperature of the active ingredient.

In some applications, the sensor includes a temperature sensor configured to detect an indication of a temperature of the plant material, and the control circuitry is configured to calculate a rate of airflow through the vaporizing unit, based upon the indication of the temperature of the plant material measured by the temperature sensor. In some applications, the control circuitry is configured to calculate the rate of airflow through the vaporizing unit by detecting an indication of an amount of energy required to maintain the temperature of the plant material constant. In some applications, the control circuitry is configured to calculate the rate of airflow through the vaporizing unit by detecting an indication of a change in the temperature of the plant material that is caused by heat transfer from the plant material to ambient air that passes through the capsule. In some applications, the control circuitry is configured to receive an indication of ambient temperature, and to calculate the rate of airflow through the vaporizing unit, by accounting for a difference between the temperature of the plant material and the ambient temperature.

In some applications, the temperature sensor is configured to detect a change in the temperature of the plant material within 0.01 second of the change occurring. In some applications, the temperature sensor is configured to detect the temperature of the plant material without drawing heat from the plant material. In some applications, the temperature sensor includes an optical temperature sensor. In some applications, the temperature sensor includes an infrared temperature sensor. In some applications, the apparatus further includes a capsule configured to house the portion of plant material, and the temperature sensor is configured to detect the indication of the temperature of the plant material by detecting a temperature of the capsule. In some applications, the temperature sensor is configured to detect the indication of the temperature of the plant material by detecting electrical resistance of at least a portion of the capsule.

In some applications, during a smoking session, the control circuitry is configured to dynamically respond to changes in the user's inhalation by:
receiving indications of the airflow rate through the vaporizing unit from the sensor;
in response to receiving the indications of the airflow rate, determining updated smoking profiles that are desired by the user; and
driving the heating element to vaporize the active ingredient of the plant material by heating the plant material according to the determined updated smoking profiles.

In some applications, during the smoking session, the control circuitry is configured to dynamically respond to changes in the user's inhalation, on a puff-by-puff basis. In some applications, in response to receiving that airflow rate through the vaporizing unit has increased, the control circuitry is configured to drive the heating element to allow a temperature of the plant material to decrease. In some applications, during a smoking session, the control circuitry is configured to dynamically respond to changes in the user's inhalation, on a continuous basis. In some applications, during a smoking session, the control circuitry is configured to dynamically respond to changes in the user's inhalation, within 0.01 seconds of changes in airflow rate through the vaporizing unit that are generated by the user's inhalation.

In some applications, in response to receiving an indication from the sensor that airflow rate through the vaporizing unit has increased, the control circuitry is configured to drive the heating element to increase a temperature of the plant material. In some applications, the control circuitry is configured to withhold the heating element from heating the plant material above a given threshold temperature.

In some applications, the control circuitry is configured to determine a classification of the plant material, and at least partially in response thereto, to determine the first smoking profile and the updated smoking profile. In some applications, based upon the classification of the plant material, the control circuitry is configured to determine a manner in which to vary a temperature to which to drive the heating element to heat the plant material, in response to changes in the airflow through the vaporizing unit. In some applications, the plant material is housed inside a capsule, and the control circuitry is configured to determine the classification of the plant material automatically by measuring a characteristic of the capsule.

There is further provided, in accordance with some applications of the present invention, a method for use with a vaporizing unit that is configured to vaporize at least one active ingredient of a portion of a plant material, the method including:
measuring an indication of airflow rate through the vaporizing unit generated by a user;
in response to the measured indication of the airflow rate, determining a smoking profile that is desired by the user;
vaporizing the at least one active ingredient of the plant material by heating the plant material according to the determined smoking profile;
subsequently:
receiving a further indication of airflow rate through the vaporizing unit generated by the user; and
in response to receiving the further indication of the airflow rate, determining an updated smoking profile that is desired by the user; and
vaporizing the at least one active ingredient of the plant material by heating the plant material according to the determined updated smoking profile.

There is further provided, in accordance with some applications of the present invention, apparatus including:
a vaporizer comprising:
at least one capsule comprising:
a material containing at least one active ingredient; and
covering layers configured to cover the material; and
control circuitry configured to:
vaporize the at least one active ingredient of the material by heating the capsule;
classify the capsule as a given type of capsule; and
configure the heating of the capsule based upon the classification of the capsule.

In some applications, the covering layers of the capsule include meshes. In some applications, the covering layers of the capsule include perforated sheets. In some applications, the material includes a plant material selected from the group consisting of: *cannabis*, and tobacco.

In some applications, the control circuitry is configured:
to measure an indication of airflow rate through the vaporizer, and
based upon the classification of the capsule, to determine a manner in which to vary a temperature to which to heat the material, in response to changes in the airflow through the vaporizer.

In some applications, at least a portion of the capsule is colored, and the control circuitry is configured to classify the capsule as the given type of capsule by detecting the color of the portion of the capsule. In some applications, the capsule is at least partially coated with a coating that includes a material that has a predefined thermal emissivity, and the control circuitry is configured to classify the capsule as the given capsule type, by determining the thermal emissivity of the coating. In some applications, at least a portion of the capsule has a predefined electrical resistance, and the control circuitry is configured to categorize the capsule as the given capsule type, by measuring the electrical resistance of the portion of the capsule.

In some applications, the capsule is thermally coupled to at least one phase-change material and the control circuitry is configured to classify the capsule as the given type of capsule by detecting a phase-change temperature of the phase-change material. In some applications, the capsule is thermally coupled to a plurality of phase-change materials, and the control circuitry is configured to classify the capsule as the given type of capsule by detecting respective phase-change temperatures of the plurality of phase-change materials. In some applications, the control circuitry is further configured to detect whether the capsule was previously used by detecting the phase-change material.

There is further provided, in accordance with some applications of the present invention, a method including:
placing into a vaporizer at least one capsule, the capsule including covering layers, and material housed within the capsule, the material containing at least one active ingredient; and
activating control circuitry configured to:
vaporize the at least one active ingredient of the material by heating the capsule;

classify the capsule as a given type of capsule; and
configure the heating of the capsule based upon the
classification of the capsule.

The present invention will be more fully understood from the following detailed description of embodiments thereof, taken together with the drawings, in which:

BRIEF DESCRIPTION OF THE DRAWINGS

FIGS. 8A, 8B, and 8C are schematic illustrations of respective cut-away views of a smoking device that includes a vaporizing unit placed in a reloading unit, at respective stages of the operation of a capsule-loading mechanism, in accordance with some applications of the present invention;

FIG. 15 is a schematic illustration showing a three-dimensional view of a rear side of the vaporizer of FIG. 13, in accordance with some applications of the present invention;

FIG. 16 is a schematic illustration showing a cross-sectional view of the vaporizer of FIG. 13, in accordance with some applications of the present invention;

FIGS. 17A, 17B, 17C, 17D, and 17E are schematic illustrations showing cross-sectional views of an extraction mechanism of the vaporizer of FIG. 13, at respective stages of the operation of the extraction mechanism, in accordance with some applications of the present invention;

FIG. 18 is a schematic illustration of a vaporizer that is configured to automatically extract a given volumetric dose of a plant material from a mass of the plant material that is disposed in a receptacle of the vaporizer, in accordance with some applications of the present invention;

FIG. 19 is a schematic illustration showing an exploded view of the vaporizer of FIG. 18, in accordance with some applications of the present invention;

FIGS. 22A and 22B are schematic illustrations of front and rear views of the extraction mechanism of the vaporizer of FIG. 18, during a first stage of the operation of the extraction mechanism, in accordance with some applications of the present invention;

FIGS. 23A and 23B are schematic illustrations of front and rear views of the extraction mechanism of the vaporizer of FIG. 18, during a second stage of the operation of the extraction mechanism, in accordance with some applications of the present invention;

FIGS. 24A and 24B are schematic illustrations of front and rear views of the extraction mechanism of the vaporizer of FIG. 18, during a third stage of the operation of the extraction mechanism, in accordance with some applications of the present invention;

FIGS. 25 and 26 are schematic illustrations of a wiping element of the vaporizer of FIG. 18, in accordance with some applications of the present invention.

DETAILED DESCRIPTION OF EMBODIMENTS

Figure 3:
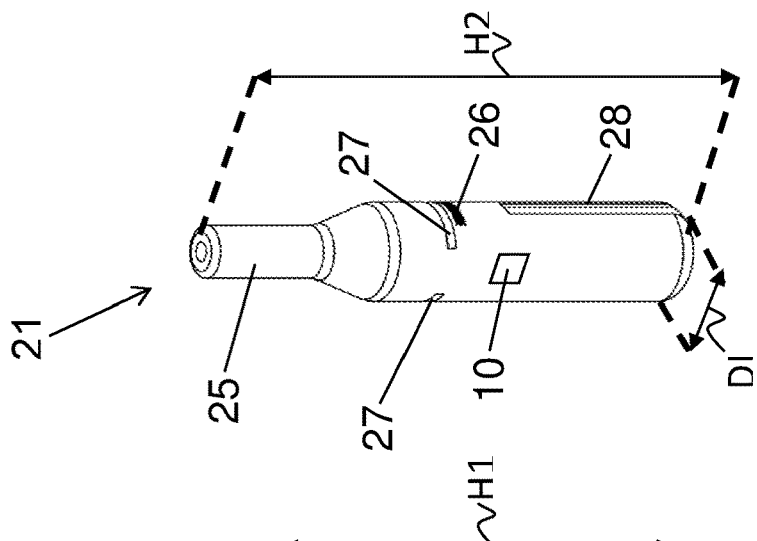
FIG. 3 is a schematic illustration of the exterior of a vaporizing unit of the smoking device of FIG. 1, in accordance with some applications of the present invention.
Figure 2:
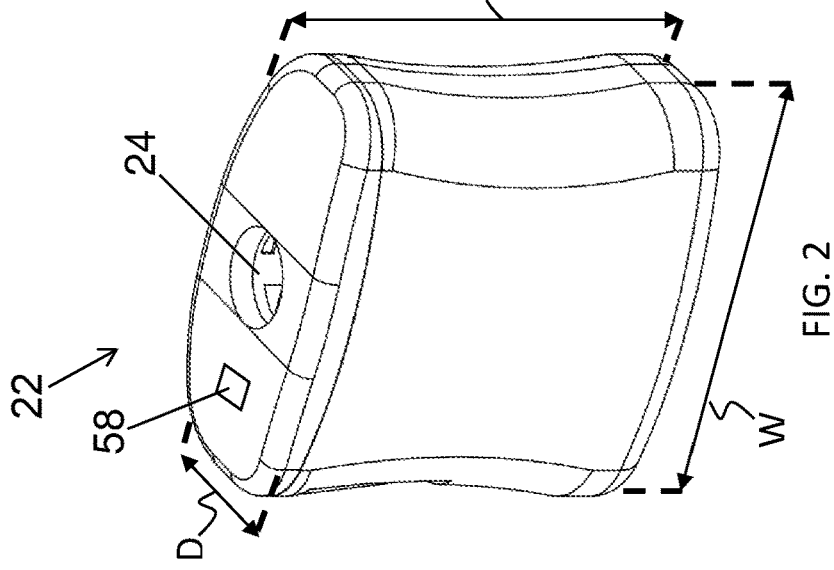
FIG. 2 is a schematic illustration of the exterior of a reloading unit of the smoking device of FIG. 1, in accordance with some applications of the present invention.
Figure 1:
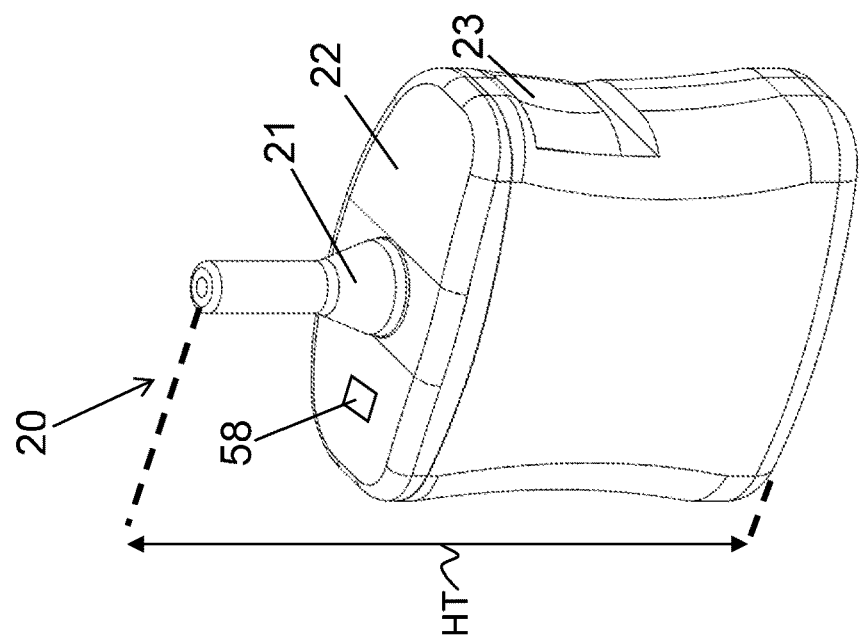
FIG. 1 is a schematic illustration of the exterior of a smoking device, in accordance with some applications of the present invention.

Reference is now made to FIGS. 1-3, which are schematic illustrations of the exterior of a smoking device 20, the smoking device including a reloading unit 22 and a vaporizing unit 21, in accordance with some applications of the present invention. Typically, smoking device 20 is used to vaporize the active ingredient of a material, such as plant material. For example, smoking device 20 may be used to vaporize the constituent cannabinoids of *cannabis* (e.g., tetrahydrocannabinol (THC) and/or cannabidiol (CBD)). Alternatively or additionally, the vaporizer is used to vaporize an active ingredient from tobacco (e.g., nicotine), and/or other plant or chemical substances that contain an active ingredient that becomes vaporized upon the substance being heated. It is noted that some applications of the present invention are described with reference to a plant material that contains an active ingredient. However, the scope of the present invention includes using any substance that contains an active ingredient (e.g., a synthetic substance that contains an active ingredient), mutatis mutandis. Smoking device 20 may alternatively be referred to as a "smoking device" and/or as an "electronic cigarette," and in the context of the present application, these terms should be interpreted as being interchangeable with one another. Similarly, in the context of the present application, the terms "vaporizing unit," "vaporizer," "electronic cigarette," and "smoking piece" should be interpreted as being interchangeable with one another.

For some applications, smoking device 20 includes a reloading unit 22 and a vaporizing unit 21. For some applications, the reloading unit houses capsules 29, a capsule-loading mechanism 56, and a power supply 45, as described in further detail herein below. For some applications, the vaporizing unit houses a vaporization location 54, an internal power supply 33 and control circuitry 34. The control circuitry is configured to act as a control unit, which controls the functioning of the vaporizing unit. Typically, the reloading unit and the vaporizing unit are reversibly couplable to each other. The smoking device is configured, such that in order to load a capsule into the vaporizing unit, and/or to discard a used capsule from the vaporizing unit, the user couples the vaporizing unit to the reloading unit, before activating the capsule-reloading mechanism, as described in further detail hereinbelow. Subsequently, in order to smoke from the vaporizing unit, the user may, if desired, detach the vaporizing unit from the reloading unit. Typically, the vaporizing unit includes a mouthpiece 25. During a smoking session, the vaporizing unit typically vaporizes the active ingredient of plant material that is disposed inside a capsule, by heating the capsule, while the capsule is disposed at the vaporization location. The user typically inhales the vaporized active ingredient via the mouthpiece.

Typically, smoking device 20 is configured to be portable and, during use, vaporizing unit 21 is configured to be held in a single hand of a user. The dimensions of the vaporizing unit are typically as follows:

A height H1 of reloading unit 22 is typically more than 5 cm (e.g., more than 6 cm), and/or less than 15 cm (e.g., less than 12 cm), e.g., between 5 cm and 15 cm, or between 10 and 12 cm.

A height H2 of vaporizing unit 21, is typically more than 6 cm (e.g., more than 8.3 cm), and/or less than 12 cm (e.g., less than 10 cm), e.g., between 7 cm and 9 cm, or between 8 and 8.5 cm.

Typically, the total height HT of smoking device 20, including the vaporizing unit inserted into the reloading unit is less than 20 cm, e.g., less than 11 cm.

A width W of reloading unit 22 is typically more than 4 cm (e.g., more than 6 cm), and/or less than 9 cm (e.g., less than 7), e.g., between 4 cm and 9 cm, or between 6 cm and 7 cm.

A depth D of reloading unit 22 is typically more than 2 cm (e.g., more than 3 cm), and/or less than 6 cm (e.g., less than 4 cm), e.g., between 2 cm and 6 cm, or between 3 cm and 4 cm.

For applications in which vaporizing unit 21 has a circular cross-section (as shown in FIG. 3), a diameter DI of the vaporizing unit is typically more than 5 mm (e.g., more than 6 mm), and/or less than 35 mm (e.g., less than 20 mm), e.g., between 5 mm and 35 mm, or between 6 mm and 20 mm. For applications in which the vaporizing unit has a non-circular cross-section, the cross-sectional area of the vaporizing unit is typically the equivalent of a circle having a diameter as described in the previous sentence.

For some applications, a capsule-loading button 23 is disposed on the outside of reloading unit 22. The capsule-loading button controls capsule-loading mechanism 56 (FIGS. 8A-C). As described in further detail hereinbelow, the capsule-loading mechanism is configured to (a) individually transfer unused capsules from a first receptacle 53 (FIG. 9C) within the body of the reloading unit to a vaporization location 54 (FIG. 6) within the body of vaporizing unit 21, at which the capsule is heated such as to vaporize the active ingredient, and (b) to individually transfer used capsules from the vaporization location within the vaporizing unit to a second receptacle 52 (FIG. 9C) within the body of the reloading unit. Alternatively or additionally, capsule-loading mechanism 56 (or any other capsule-loading mechanism described herein) is controlled by an electric motor (not shown).

Figure 4D:
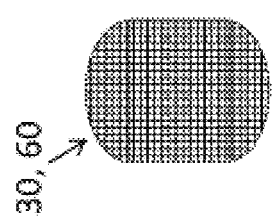
FIGS. 4D and 4E are schematic illustrations of meshes or perforated sheets of a capsule, in accordance with some applications of the present invention.
Figure 4E:
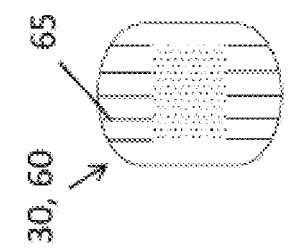
Figure 4C:
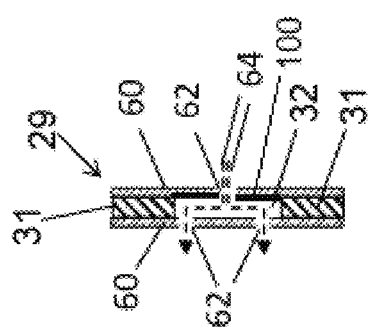
FIG. 4C is a schematic illustration of a capsule that includes perforated sheets, in accordance with some applications of the present invention.
Figure 4F:
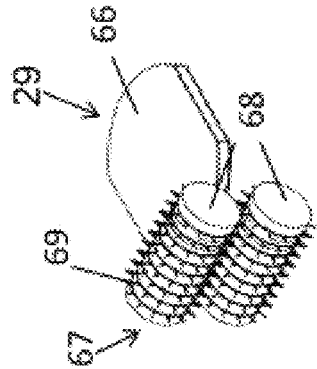
FIG. 4F is a schematic illustration of a capsule that is provided to a user with plant material within the capsule covered by non-perforated sheets, in accordance with some applications of the present invention.
Figure 4B:
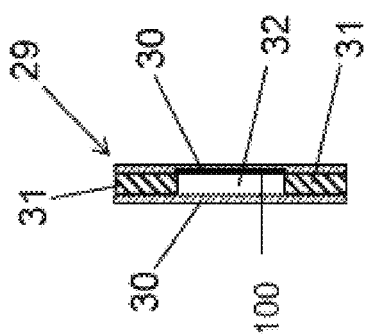
FIG. 4B is a cross-sectional view of the capsule of FIG. 4A, in accordance with some applications of the present invention.
Figure 4A:
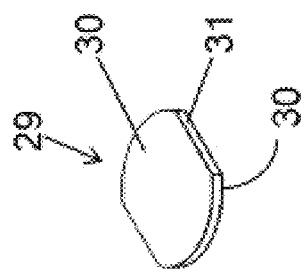
FIG. 4A is a schematic illustration of the exterior of a capsule that contains an active ingredient, in accordance with some applications of the present invention.

Reference is now made to FIGS. 4A-B, which are schematic illustrations of respective views of a capsule 29, the capsule containing material 32, e.g., a plant material, that includes an active ingredient, in accordance with some applications of the present invention. As described hereinabove, for some applications, the plant material is *cannabis*, and the active ingredient is the constituent cannabinoids of *cannabis* (e.g., tetrahydrocannabinol (THC) and/or cannabidiol (CBD)). Alternatively or additionally, the plant material includes tobacco (and the active ingredient includes nicotine), and/or other plant or chemical substances that contain an active ingredient that becomes vaporized upon the substance being heated.

Typically, capsule 29 is generally similar to capsules described in WO 16/147188, which is incorporated herein by reference. For some applications, material 32 (which contains an active ingredient, and which is typically a plant material) is housed between plant material covering layers, which is typically include upper and lower meshes (e.g., metallic meshes) 30. For some applications, each of the meshes has openings of more than 15 micron (e.g., more than 20 micron), and/or less than 80 micron (e.g., less than 50 micron), e.g., 15-60 micron, or 20-50 micron. Typically, the meshes are coupled to a central portion 31 of the capsule (e.g., a central disc, as shown), the central portion defining a hole. For example, the meshes may be coupled to the central portion via an adhesive, such as a high-temperature-resistant glue, or double-sided adhesive or ultrasonically welded to central portion or heat pressed onto central portion. Typically, the adhesive is configured such that the adhesive does not emit fumes, even when the adhesive is subjected to a high temperature, such as a temperature of greater than 200 degrees Celsius. Typically, the material is housed between the meshes and within the hole defined by the central portion of the capsule.

Typically, plant material 32 is ground, such that (a) the material is in sufficiently small pieces that the material fits within the capsule, and a large surface area of the material is exposed to air flow through the vaporizing unit (b) the pieces of the material are sufficiently large that they do not pass through the meshes, and (c) the active ingredient within the material retains its potency. For some applications, the material is cryogenically ground and/or powderized.

For some applications, central portion 31 of capsule 29 is made of a material that has a high heat capacity and/or low heat conductivity so that it reduces heat loss from the capsule to the surrounding area and reduces heating of the surrounding area during the vaporization process. For some applications, at least one of the wires of meshes 30 is hollow, and a phase-change material is disposed inside the hollow wire. Alternatively or additionally, a phase-change material is coupled to the capsule is a different manner, e.g., by coating the capsule with the phase-change material. For some applications, the phase-change material is configured to reduce heat loss from the capsule, by causing the capsule to preferentially absorb heat relative to the areas surrounding the capsule. Alternatively or additionally, the phase-change material is selected such as to maintain the capsule below the pyrolysis temperature of the plant material, and to thereby prevent the plant material from being pyrolyzed. For example, the phase-change material may undergo a phase-change at a temperature that is between the vaporization temperature and the pyrolysis temperature of the plant material, such that the phase-change material absorbs heat as latent heat of fusion at this temperature. For some applications, a phase-change material is coupled to the capsule in order to facilitate the automatic identification of the capsule type, by the control circuitry of the vaporizing unit, as described in further detail hereinbelow.

Reference is now made to FIG. 4C, which is a schematic illustration of capsule 29, the capsule including perforated sheets 60, in accordance with some applications of the present invention. For some applications, plant material 32 is housed inside the central portion of the capsule between first and second perforated sheets. Typically, for applications as shown in FIG. 4C, upper and lower perforated sheets are used as covering layers for covering the plant material, instead of the upper and lower meshes 30 as shown in FIG. 4B, for example. For some applications, each of the perforated sheets defines one or more perforations 62 that are configured to guide airflow through the plant material along a given airflow path, during the vaporization process. For example, FIG. 4C shows airflow arrows 64, which illustrate an airflow path that is generated by perforations 62. Typically, the perforations are configured to guide airflow through the plant material along an airflow path that increases contact area between the flowing air and the plant material within the capsule). For some applications, the perforated sheets are configured to be heated in a similar manner to that described herein with reference to meshes 30, mutatis mutandis. For example, the perforated sheets may be made of an electrical conductive material that is configured to be heated via resistive heating. In general, techniques that are described herein with reference to capsule that include meshes 30 as the covering layers for covering the plant material, may be performed with respect to capsules that include perforated sheets 60 as the covering layers for covering the plant material, mutatis mutandis.

Reference is now made to FIGS. 4D and 4E, which are schematic illustrations of meshes 30 or perforated sheets 60, in accordance with some applications of the present invention. For some applications, the perforation pattern of the perforated sheets, or the pattern of holes in the meshes, is uniform across the surface of each of the perforated sheets, or each of the meshes, as shown in FIG. 4D, for example. Alternatively, the perforation pattern of the perforated sheets, or the pattern of holes in the meshes, is non-uniform across the surface of each of the perforated sheets, or each of the meshes, as shown in FIG. 4E, for example. For some applications, the perforation pattern of the perforated sheets, or the pattern of holes in the meshes, is varied across the surface of each of the perforated sheets, or each of the meshes, in order control the resistance and/or the resistivity pattern of the sheet. For example, use of selective perforation may implemented in order to limit resistive heating to the contact area between the perforated sheet or the mesh and the plant material, and/or to focus the resistive heating upon that area. Alternatively or additionally, non-uniform perforation spacing may be used, for example, to control the current density at different locations across the surface of the perforated sheets, or the meshes. An example of this is shown in FIG. 4E, which shows slits 65 on mesh 30 or perforated sheet 60, the slit being configured to prevent electrical current from flowing across the mesh or the sheet at regions at which the plant material is not housed. As described hereinabove, for some applications, perforations 62 are disposed upon sheets 60 such as to guide airflow through the plant material along a given airflow path, during the vaporization process.

Reference is now made to FIG. 4F, which is a schematic illustration of capsule 29, in accordance with some applications of the present invention. For some applications, capsule 29 is configured to be provided to a user with plant material 32 within the capsule covered by non-perforated sheets 66, the non-perforated sheets acting as the covering layers for covering the plant material. For example, the capsules may be provided to the user in this state, such that the non-perforated sheets preserve the plant material within the capsule, and/or maintain the potency of the active ingredient within the plant material. Typically, prior to the plant material being heated inside the vaporizer, sheets 66 are perforated, in order to allow airflow through the capsule. For some applications, the user perforates the sheets prior to placing the capsule inside the vaporizer. Alternatively, the vaporizer includes a perforating mechanism 67 that is configured to perforate sheets 66 prior to the plant material being heated inside the vaporizer. For example, as shown in FIG. 4F (which shows the perforating mechanism in the absence of the other component of the vaporizer, for illustrative purposes), the perforating mechanism may include one or more rollers 68 with pins 69 disposed thereon. For some applications, the perforation mechanism is configured to perforate sheets 66, such that the perforation pattern that is formed is uniform across the surface of each of the sheets, for example, as shown in FIG. 4D. Alternatively, the perforation mechanism is configured to perforate sheets 66, such that the perforation pattern that is formed is non-uniform across the surface of each of the sheets, for example, as shown in FIGS. 4C and 4E. For some applications, sheets 66 are configured to be heated in a similar manner to that described herein with reference to meshes 30, mutatis mutandis. For example, the sheets may be made of an electrical conductive material that is configured to be heated via resistive heating. In general, techniques that are described herein with reference to capsules that include meshes 30 as the covering layers for covering the plant material, may be performed with respect to capsules that include sheets 66 as the covering layers for covering the plant material, mutatis mutandis.

For some applications, capsule 29 is configured to keep the plant material fully encapsulated such that there is substantially no emission of active ingredient prior to the vaporization of the active ingredient inside the vaporizer. For example, the capsule may be configured in this manner by the use of non-perforated sheets 66, as described with reference to FIG. 4F.

Figure 5:
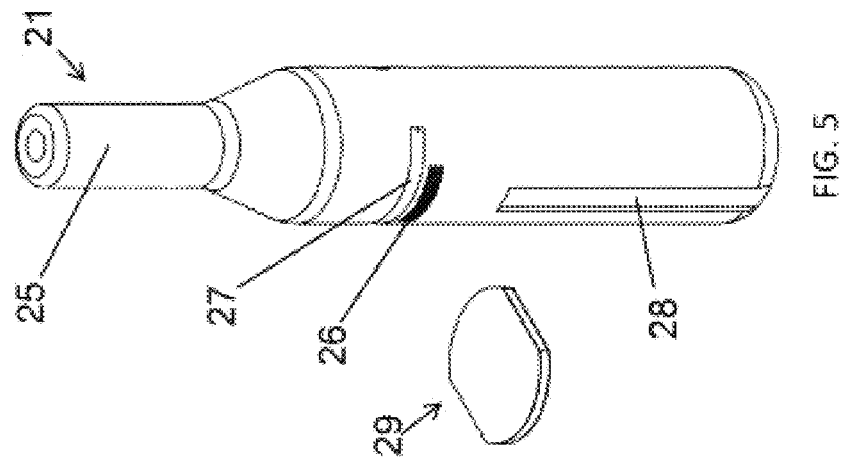
FIG. 5 is a schematic illustration of the exterior of a vaporizing unit and a capsule aligned for insertion into the vaporizing unit, in accordance with some applications of the present invention.
Figure 7:
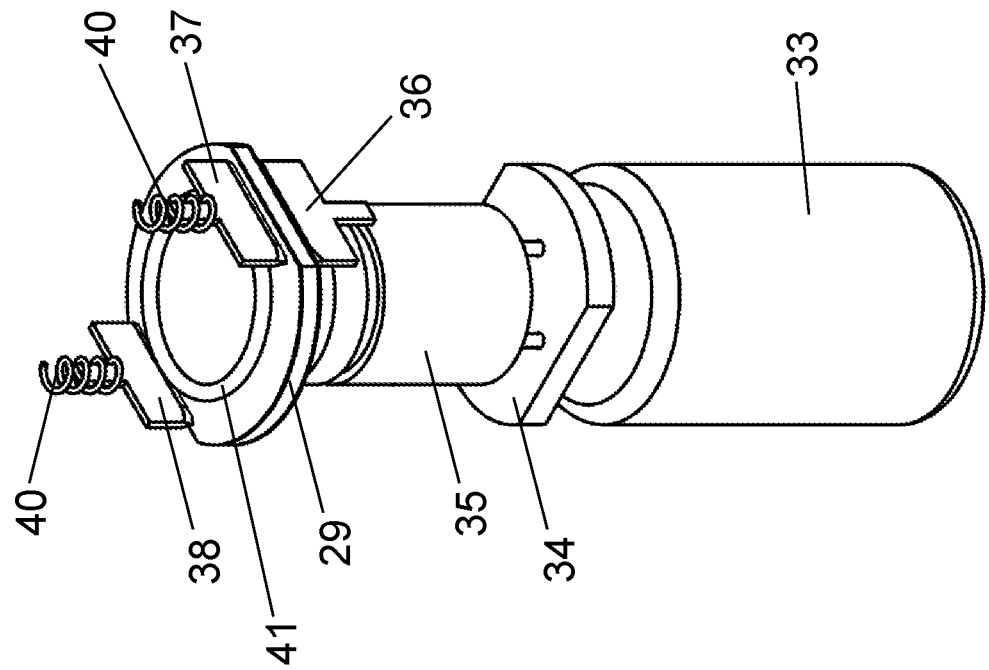
FIG. 7 is a schematic illustration of a portion of a vaporizing unit of FIG. 3 with a capsule disposed at a vaporization location within the vaporizing unit, in accordance with some applications of the present invention.
Figure 6:
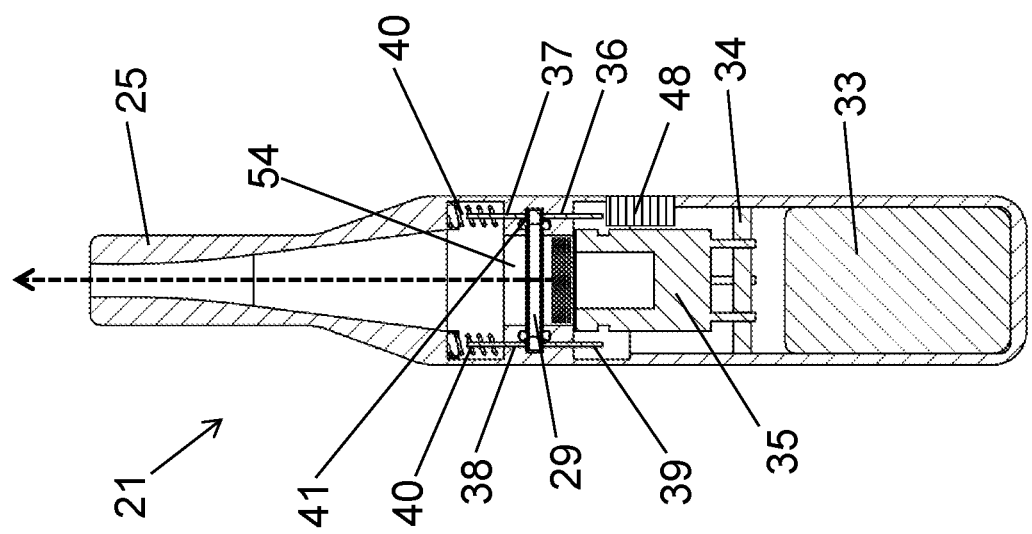
FIG. 6 is a cross-sectional view of the vaporizing unit of FIG. 3, in accordance with some applications of the present invention.

Reference is now made to FIGS. 5-7, which are schematic illustrations of respective views of vaporizing unit 21, in accordance with some applications of the present invention. For some applications, the vaporizing unit receives capsules by the vaporizing unit being coupled to reloading unit 22, and capsule-loading mechanism 56 being used to load capsules into the vaporizing unit. Alternatively or additionally, the vaporizing unit is used in the absence of the reloading unit, and, for example, a user may insert individual capsules into the vaporizing unit. For some such applications, after the user has smoked the individual capsule, the individual capsule needs to be removed from the vaporizing unit before another capsule can be inserted. Alternatively, the vaporizing unit is configured such that a used capsule is automatically pushed out of the vaporization location, by a new capsule beg inserted into the vaporization location. Further alternatively, the vaporizing unit is configured to hold a plurality of used capsule, such that the used capsules only need to be removed from the vaporizing unit periodically, and not after each capsule is smoked.

For some applications, the vaporizing unit of the smoking device is configured to be used with a plurality of different types of capsules. For example, respective types of capsules may contain different quantities of plant material, plant material containing different amount of active ingredients, and/or different types of plant materials. Alternatively or additionally, respective types of capsules may have respective characteristics, e.g., respective flavors, strengths, richnesses, active ingredients, etc. For some applications, the reloading unit is configured such that the user may select which capsule type to place in the reloading unit, and the reloading unit may then be used to load the vaporizing unit with that type of capsule. Alternatively, a reloading unit may come preloaded with a given type of capsules. Further alternatively, as described hereinabove, the vaporizing unit may be configured such that the user can insert capsules directly into the vaporizing unit. For such applications, the user is able to select which type of capsule he/she wishes to smoke at any given time, and to insert that type of capsule into the vaporizing unit.

For some applications, control circuitry 34 of the vaporizing unit is configured to adjust a heating profile of the capsules to the capsule type that is currently being heated. For some such applications, the control circuitry implements an automatic capsule classification procedure in accordance with which the control circuitry automatically classifies the capsule that is currently being heated as a given type of capsule (i.e., the control circuitry identifies the capsule type), and designates a capsule heating profile accordingly.

For some applications, color coded capsules are used for identification of different capsules by the user and/or for automatic classification of the capsule by the control circuitry of the vaporizing unit, for example, by use of a color sensor. For some applications, the thermal emissivity of the capsules is used for classification of different capsules by the control circuitry, for example, by coating one or more of the metallic meshes of each of the capsules with coatings having respective thermal emissivity constants. For some applications, the identification of the above-mentioned thermal emissivity constant of the capsule is measured by the vaporizing unit, while the coating of the capsule is at a known temperature. For example, the control circuitry may measure the thermal emissivity of the capsule coating while the capsule is in an unused state, and can therefore be assumed to be approximately at ambient temperature. For some applications, a standard temperature sensor is used to measure the temperature of the capsule coating. For some applications, a temperature sensor as described hereinbelow is used to measure the temperature of the capsule coating.

For some applications, the control circuitry is configured to perform the classification of the capsule type by phase-change materials having respective phase-change temperatures being used with each capsule type. Typically, the phase-change material is at least partially disposed within the capsules and is thermally coupled to one or more of the metallic meshes of the capsules. Further typically, the phase-change temperature of the phase-change material is below the vaporization temperature of the active ingredient. During the heating of a capsule, the phase-change material reaches its phase-change temperature and accumulates latent heat, while it is in the process of undergoing the phase change. In accordance with respective applications, within the temperature range to which the capsule is heated, the phase-change material may be configured to undergo a phase change from solid to liquid, from liquid to gas, from gel to gas, and/or from solid to gas. Typically, while the phase-change material undergoes the phase change, the measured temperature of the phase-change material, and of the capsule, remains constant. The constant temperature is typically maintained for a short duration of time, followed by a continued increase in the temperature of the capsule after the phase change transition of the phase-change material has been completed. For some applications, the control circuitry is configured to detect the temperature at which the capsule's temperature remains constant for a given period of time, during the heating of the capsule. Since this temperature is indicative of the phase-change temperature, the control circuitry is configured to classify the capsule type in response to detecting this temperature. For example, different types of capsules can be classified by using phase-change materials with pre-defined phase-change temperatures. Purely by way of example, phase-change materials having phase-change temperature levels of approximately 60 degrees Celsius, approximately 65 degrees Celsius, approximately 70 degrees Celsius, approximately 75 degrees Celsius, and approximately 80 degrees Celsius can be used to classify five different types of capsules. As described hereinabove, typically, in response to detecting a given capsule type, a capsule heating profile that is suited to that capsule type is applied.

For some applications, in cases in which it is desired to prohibit the re-use of already vaporized capsules, the control circuitry is configured to detect a presence of a phase-change material within the capsule. For some applications, the phase-change material is configured to be vaporized, to dissipate, and/or to lose its phase changing properties, in response to the capsule being used, due to its temperature having been increased above its phase-change temperature. The control circuitry is configured to interpret the presence of the phase-change material within the capsule, and/or a characteristic of the phase-change material within the capsule, as indicating that the capsule was not previously vaporized, and to allow the capsule to be heated, only in response thereto. For example, in cases in which re-use of capsules might cause an increased emission of harmful materials or might cause pyrolysis of the dry, used active ingredient, the control circuitry may be configured as described.

For some applications, a phase-change material is mixed with the plant material within the capsule. Alternatively or additionally, the phase-change material is shaped as a thin plate and is disposed within the capsule such that the phase-change material encapsulates the plant material. In this manner, in addition to the thermal phase-change properties of the phase-change material described hereinabove, the phase-change material facilitates the preservation of and/or reduces the degradation of the plant material, prior to the plant material being heated.

For some applications, respective capsule types are provided with meshes having respective resistance levels. The control circuitry is configured, by measuring the resistance of the mesh, to identify the capsule type that is currently being heated. As described hereinabove, typically, in response to classifying the capsule as a given capsule type, a heating profile that is suited to that capsule type is applied. For some applications, constructing meshes having respective resistances is performed by using materials with respective resistances, and/or by modifying the mechanical properties of the meshes, such as length, width, cross section, and/or any other property that might influence the resistance. For some applications, a generally similar technique is performed, but the capsules are identified via the electrical resistance of a different portion of the capsules, for example, the main body of the capsules, a resistor embedded in the capsule, and/or resistance of a material within the capsule.

For some applications, capsules types are identified by use of other types of coding. For example, barcode, unique mechanical features (for example: holes or grooves), switches, electro-optical switches, RFID, or any other applicable coding mechanism.

For some applications, vaporizing unit 21 includes a grill 26, which is configured to allow airflow into the body of the vaporizing unit, as described in further detail hereinbelow. For some applications, a capsule loading and unloading opening 27 is configured to allow the manual and or mechanized loading and unloading of capsules into and out of the vaporization location within the vaporizing unit, as described in further detail hereinbelow.

For some applications vaporizing unit 21 defines a groove 28, which is configured to facilitate insertion of the vaporizing unit into reloading unit 22 in a given alignment. For example, the groove may be configured to facilitate insertion of the vaporizing unit into the reloading unit such that capsule loading and unloading opening 27 is correctly aligned such as to receive capsule from receptacle 53 of the reloading unit, and to deposit capsules into receptacle 52 of the reloading unit.

For some applications, the inner surface of mouthpiece 25 (and/or other portions of the vaporizer) includes a lipophobic or hydrophobic coating that is configured to prevent products of the vaporization of the active ingredient from sticking to the inner surface of the mouthpiece. Alternatively or additionally, a filter is used to filter at least a part of the vapors that pass through the mouthpiece. For some applications, a filter that is similar to that of a traditional combustion cigarette is used, for example, in order to provide the user with a look and feel that is similar to that of a cigarette during the use of the vaporizing unit of the smoking device.

Typically, vaporizing unit 21 is inserted into reloading unit 22 for the purpose of loading a new capsule into the vaporizing unit (e.g., to the vaporization location of the vaporizing unit), as described hereinabove. Alternatively or additionally, the reloading unit contains a power supply 45 (FIGS. 8A-C and 9A-C), and an internal power supply 33 of the vaporizing unit is configured to become charged by the power supply of the reloading unit, by the vaporizing unit being coupled to reloading unit. For some applications, power supply 45 of the reloading unit, and/or power supply 33 of the vaporizing unit is configured to receive power from an external power source, such as mains electricity. Typically, the vaporizing unit is decoupled from the reloading unit prior to the user using the vaporizing unit to vaporize the active ingredient of the plant material, to thereby smoke from the vaporizing unit. During a smoking session, the vaporizing unit, which typically has a shape that is generally similar to that of a cigarette, is held by the user, and functions as an electronic cigarette.

Reference is again made to FIG. 6, which is a schematic cross-sectional illustration of vaporizing unit 21, in accordance with some applications of the present invention. Reference is also made to FIG. 7, which is a schematic illustration of components vaporizing unit 21, in accordance with some applications of the present invention. Typically, vaporizing unit 21 includes one or more heating elements, which are configured to heat the plant material within capsule 29 (such as to vaporize the active ingredient within the plant material). For some applications, electrodes 36, 37, 38, and 39 are configured to act as heating elements, by heating the plant material within the capsule, by driving an electrical current into capsule 29. As described hereinabove, for some applications, capsule 29 includes one or more metallic meshes 30 (FIG. 4A-B). The electrodes heat the material inside the capsule by heating the one or more meshes via resistive heating, by driving a current into the one or more meshes. Alternatively or additionally, the electrodes heat an internal heating element 100 that is housed within the capsule, by driving a current into the internal heating element 100. Typically, the electric current that is driven is controlled, such that, for example, the heating of the capsules is not affected by variations in the degree of contact between the electrodes and the meshes of the capsules.

For some applications, upper mesh of capsule 29 is electrically connected to the lower mesh, and at least two electrodes are used to drive an electrical current into capsule 29. For example, referring to the view shown in FIG. 7, electrodes 36 and 37 may be used, and the upper and lower meshes may be electrically connected to one another on the far side of capsule 29. For some applications, the lower mesh and/or the upper mesh is heated by the mesh being used to complete a circuit between a pair of electrodes. For example, the plant material contained within the capsule may heated by driving a current from first electrode 36 to second electrode 39 via the lower mesh of capsule 29. Alternatively or additionally, the plant material contained within the capsule may be heated by driving a current from third electrode 37 to fourth electrode 38 via the upper mesh of capsule 29. For some applications, by heating the plant material in the aforementioned manner, the plant material within the capsule is heated more uniformly than if, for example, a monopolar electrode were to drive a current into a location on the upper or lower mesh. For some applications, capsule 29 includes the internal heating element 100 (e.g., an internal mesh), as an alternative or in addition to the upper and lower meshes. The internal heating element is configured to be heated in a similar manner to that described with reference to the upper and lower meshes, and is configured to heat the capsule via conductive heating.

For some applications, springs 40 are coupled to at least some the electrodes, e.g., electrodes 37 and 38 as shown in FIG. 7. The springs are configured to push the electrodes towards the capsule 29, in order to improve electrical coupling between the electrodes and the capsule. For some applications, the electrodes include a bladed tip that acts as the electrical contact to the capsule. Typically, the tips of the electrodes have a thickness of more than 0.05 mm (e.g., more than 0.1 mm), and/or less than 0.4 mm (e.g., less than 0.3 mm), e.g., between 0.05 mm and 0.4 mm, or between 0.1 mm and 0.3 mm.

For some applications, an electrode-movement mechanism (not shown) is configured to move at least a portion of the electrodes with respect to a mesh of capsule 29. For example, an electrode-movement mechanism as described in WO 16/147188 to Raichman, which is incorporated herein by reference, may be used. For example, the electrode-movement mechanism may move the electrodes closer to the mesh, and/or may move the electrodes with respect to the mesh (e.g., by sliding the electrodes across the surface of the mesh), while the electrodes are in contact with the mesh. In this manner, the electrodes typically remove at least a portion of a coating that has developed on the surface of the mesh, and/or penetrate the coating. For some applications, the electrode-movement mechanism is configured to move the electrodes away from the mesh, for example, in order to facilitate insertion of a capsule into the vaporization location or removal of a capsule from the vaporization location, in a manner that friction between the capsule and the electrodes is reduced or eliminated.

Although vaporizing unit 21 has been described as using resistive heating of electrode(s) 36, 37, 38, and/or 39 to heat capsule 29, for some applications, alternative or additional heating elements and heating techniques are used to heat the capsule. For example, a laser emitter may act as a heating element by directing a laser beam at the capsule, in order to heat the capsule. For some applications, a separate heating element that is housed inside the vaporizing unit is heated in proximity to the vaporization location, in order to provide conduction, convection, and/or radiation heating to the capsule.

During use of the vaporizing unit, the user typically inhales via mouthpiece 25. This causes air to flow through grill 26 (FIG. 5) to the mouthpiece via the capsule, as indicated by the dashed airflow arrow in FIG. 6. Typically, the capsule is configured to be placed at the vaporization location within the vaporizing unit, such that planes defined by the upper and lower meshes are perpendicular to a direction of the air flow through the vaporizer at the vaporization location. For some applications, a sealing gasket 41 is used to prevent air from outside the vaporizing unit from flowing into mouthpiece 25 without passing through capsule 29.

Typically, a power supply 33 (e.g., a battery) and control circuitry 34 are housed inside the body of vaporizing unit 21. Typically, the power supply and/or the control circuitry are coupled to the body of the vaporizing unit by a coupling element, such as an adhesive, a screw, a clip, and/or a pin. For some applications, the control circuitry is configured to drive a current into the capsule via electrodes 36, 37, 38, and/or 39, using power supplied by the power supply.

Typically, the control circuitry comprises electronic components, such as resistors, transistors, capacitors, inductors and diodes. For some applications, the control circuitry includes a computer processor, which typically acts as a special purpose vaporization-controlling computer processor. Typically, the operations described herein that are performed by such a computer processor transform the physical state of a memory, which is a real physical article, to have a different magnetic polarity, electrical charge, or the like depending on the technology of the memory that is used.

For some applications, vaporizing unit 21 includes a temperature sensor 35 that is configured to measure an indication of the temperature of the material that is being heated, e.g., by measuring the temperature of the capsule that is being heated. For example, the temperature sensor may be an optical temperature sensor, such as an infrared temperature sensor, that is configured to measure the temperature of the capsule without contacting the capsule. FIGS. 6-7 shows sensor 35 aligned to receive beams of optical light from capsule 29, the capsule having been heated. Sensor 35 is configured to measure the temperature of capsule 29, based upon the received light. In this manner, the optical temperature sensor measures the temperature of the capsule, without affecting the temperature of the capsule by drawing heat from the capsule. For some applications, the temperature sensor is covered with a lipophobic or hydrophobic coating that protects the temperature sensor from products of the vaporization being deposited upon the temperature sensor. The temperature sensor typically has a "near zero" response time, such that the control circuitry is able to measure changes in temperature due to changes in airflow, and respond to such changes in the manner described hereinbelow, effectively immediately with respect to the perception of the user. For example, the temperature sensor may be configured to detect changes in temperature within 0.01 seconds, e.g., within 1 millisecond, of such changes. For some applications, by virtue of having such a temperature sensor, the control circuitry is configured to respond to airflow-induced changes in temperature within 0.01 seconds, e.g., within 1 millisecond, of such changes.

For some applications, vaporizing unit 21 includes a fan 48 (FIG. 6) that is configured to vent out vapors during the heating process, by ventilating a space between temperature sensor 35 and the capsule. Typically, during heating of the plant material, vapors are emitted. In some cases, in the absence of fan 48, the vapors may mask the capsule and/or the plant material from temperature sensor 35. In turn, this may cause errors in the temperature that is measured by the temperature sensor (and particularly if sensor 35 is an infrared temperature sensor). For example, the sensor may measure the temperature of the plant material as being lower than it actually is, which could lead to the plant material being overheated, causing damage, pyrolysis, and/or or ignition of the plant material. Therefore, for some applications, fan 48 vents vapors from the vaporizing unit during at least a portion of the heating process, by driving air into and/or out of the vaporizing unit. Alternatively or additionally, unwanted vapor accumulation within the device is reduced by designing internal passages of the device with dimensions that are such to allow air flow between the temperature sensor and the plant material that is sufficient to prevent vapor accumulation.

For some applications, a different temperature sensor is used. For example, the control circuitry may detect the temperature of the capsule by detecting changes in the resistance of components of the capsule (e.g., mesh 30 of the capsule) using electrodes 36, 37, 38, and/or 39.

For some applications, smoking device 20 includes a port (not shown) via which the smoking device is connected to an external source of power and/or data input. For example, power supply 45 of reloading unit 22 may be configured to be recharged by connecting the smoking device to an external power supply (e.g., mains electricity) via the abovementioned port. Alternatively or additionally, control circuitry 34 may receive data, e.g., programming instructions, via above mentioned port.

For some applications, a user may input instructions into the control circuitry that control the amount of heat that is applied for a given rate of airflow through the capsule. For example, the user may input the instructions via a user interface 10 (such as a touchscreen display, or buttons), shown in FIG. 3, that is coupled to the control circuitry. Alternatively or additionally, the user may input the instructions via a computer, a tablet device, a phone, and/or a different telecommunications device that communicates with the control circuitry via a wired or a wireless communications protocol. For example, the user may indicate a type of smoking that he/she desires (e.g., intense, slow-burn, etc.), and the control circuitry may control the amount of heat that is applied for a given rate of airflow through the capsule, in response thereto. For some applications, the control circuitry is configured to automatically determine a desired smoking profile, based upon the rate of airflow through the vaporizing unit (e.g., through the capsule), as described in further detail hereinbelow. By controlling the amount of heat that is applied for a given rate of airflow through the capsule, the amount of the active ingredient that is vaporized per unit airflow rate through the vaporizer may be controlled. For some applications, vaporizing unit 21 includes an airflow sensor, (not shown). For some applications, the control circuitry is configured to automatically determine the rate of airflow through the vaporizer, by detecting the temperature of the capsule, as described in further detail hereinbelow.

For some applications (not shown), vaporizing unit 21 is shaped to define a supplementary airflow channel, which provides airflow out of mouthpiece 25, but not via the capsule that is being vaporized (not shown). In this manner, in response to a large inhalation by the user, the vaporizer is able to provide air to the user, without increasing the dosage of the active ingredient that is provided to the user.

For some applications, control circuitry 34 of the vaporizing unit or control circuitry of the reloading unit (not shown) includes one or more indicators for generating alerts to the user. For example, the control circuitry may illuminate an indicator light, may cause the vaporizing unit to vibrate, and/or may emit an audio signal (e.g., a beep). Alternatively, the vaporizing unit may include user interface 10, which may include a display (e.g., an LED or LCD display), and the control circuitry may generate an alert on the display. For some applications, the control circuitry is configured to generate an alert to the user in response to sensing that, during inhalation from the vaporizer by the user, the temperature of the plant material is less than a given threshold temperature. Alternatively or additionally, the control circuitry is configured to generate an indication to the user in response to sensing that the temperature of the plant material is greater than a given threshold temperature (e.g., a temperature of more than between 300 degrees Celsius and 350 degrees Celsius), which may cause the material to become pyrolyzed or ignite. For some applications, the threshold is measured with respect to an expected target temperature. For example, an alert may be generated in response to sensing a temperature that is 50 degrees Celsius less than an expected target temperature. Further alternatively or additionally, the control circuitry is configured to generate an indication to the user that a capsule is faulty, is incorrectly placed, and/or is missing, in response to measuring a temperature that is less than a given threshold, during the heating process.

Figure 9A:
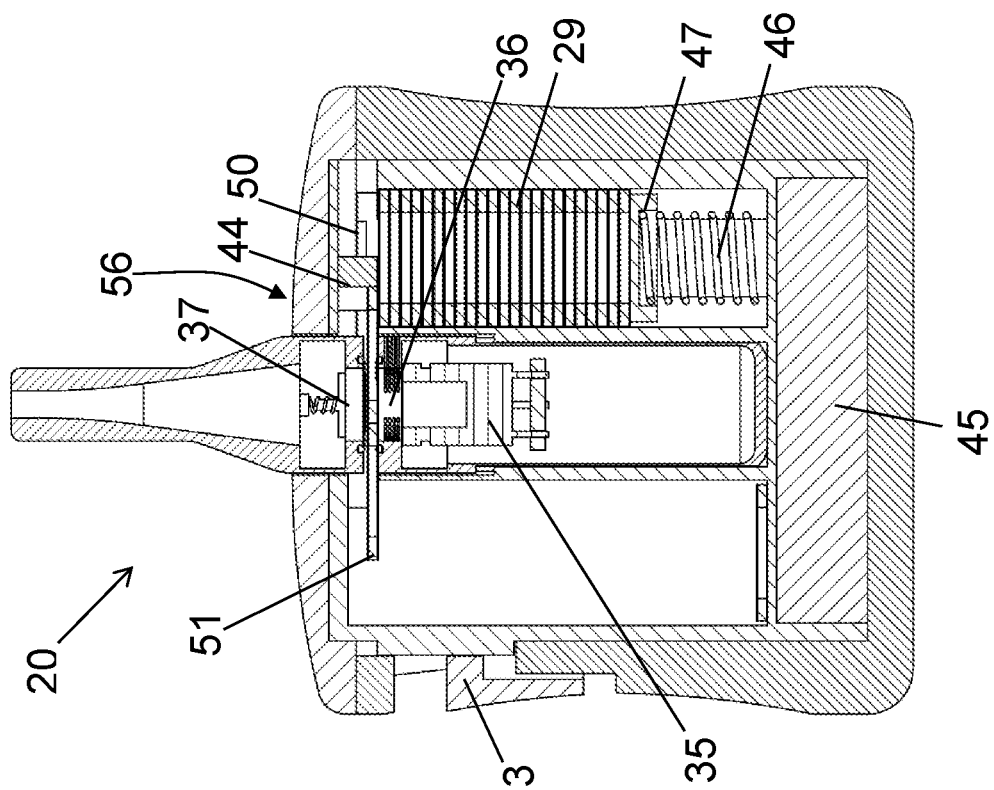
FIGS. 9A, 9B, and 9C are respective cross-sectional views of a smoking device that includes a vaporizing unit placed in a reloading unit, at respective stages of the operation of a capsule-loading mechanism, in accordance with some applications of the present invention.
Figure 9B:
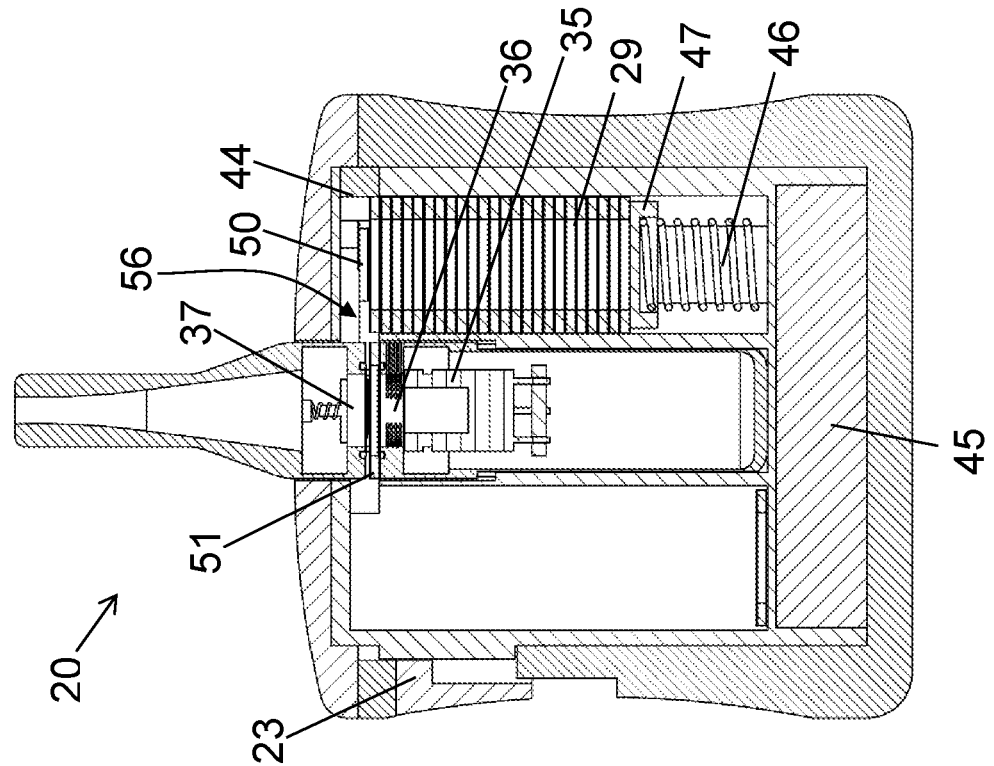
Figure 9C:
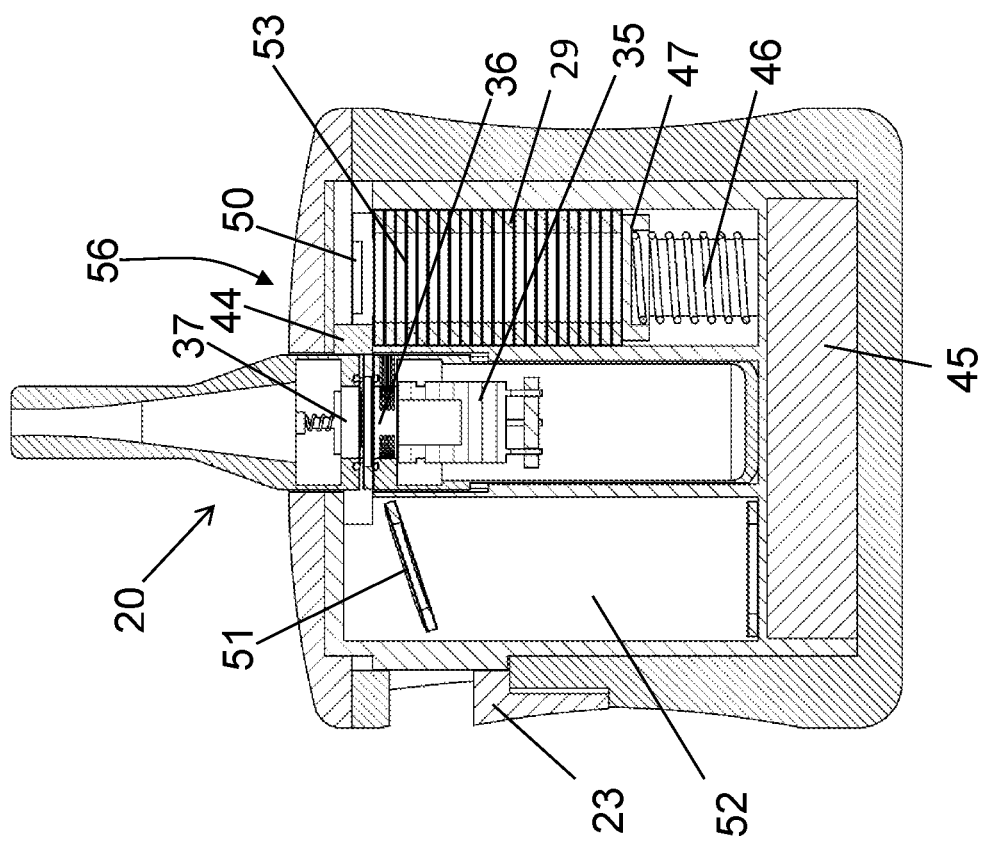

Reference is now made to FIGS. 8A-C, which are schematic illustrations of smoking device 20, showing vaporizing unit 21 placed in a portion of reloading unit 22, at respective stages of the operation of capsule-loading mechanism 56, in accordance with some applications of the present invention. Reference is also made to FIGS. 9A-C, which are schematic cross-sectional views of smoking device 20, showing vaporizing unit 21 placed in a portion of reloading unit 22, at respective stages of the operation of capsule-loading mechanism 56, in accordance with some applications of the present invention.

Typically, reloading unit 22 of smoking device 20 includes first and second receptacles 53 and 52 (shown in FIG. 9C), which are configured to house capsules 29. Unused capsules are typically housed in a stacked configuration (i.e., such that when the smoking device is in an upright orientation, the capsules are arranged one above the other) inside first receptacle 53, and used capsules are housed in a stacked configuration inside second receptacle 52. Typically, a spring 46 and a pushing element 47 are coupled to a bottom of first receptacle 53. The spring and pushing element are configured to maintain the stacked configuration of the capsules inside the first receptacle by pushing the capsules toward the top of the first receptacle within the reloading unit. For some applications, by storing the capsules in stacked configurations, dimensions of the width and depth of smoking device 20 may be such that the smoking device can be comfortably held by a user (e.g., within a single hand of the user) or carried in the user's pocket.

For some applications, capsules 29 have circular cross-sections, and receptacles 52 and 53 define cylindrical tubes that house the capsules. Alternatively, capsules 29 may have a different shape, and receptacles 52 and 53 may define hollow spaces that are shaped so as to conform with the shapes of the capsules. For example, as shown in FIG. 4A, the capsules may have a racetrack-shaped cross section.

Typically, the capsule-loading mechanism 56 is configured to (a) individually transfer unused capsules from first receptacle 53 inside reloading unit 22 to vaporization location 54 (FIG. 6) inside vaporizing unit 21, at which location the capsule is heated such as to vaporize the active ingredient of the plant material, and (b) to individually transfer used capsules from the vaporization location to second receptacle 52 located inside reloading unit 22.

For some applications, vaporizing unit 21 is configured to become coupled to reloading unit 22, such that the top of receptacle 53 and the top of receptacle 52 inside reloading unit 22, and vaporization location 54 (FIG. 6) inside vaporizing unit 21, are linearly aligned with each other (for example, across the width of the smoking device, as shown in FIGS. 9A-C). For some such applications, capsule-loading mechanism 56 is a linear capsule-loading mechanism, configured to move each of the capsules by moving linearly. The capsule-loading mechanism is configured to push unused capsules from receptacle 53 to vaporization location 54 (FIG. 6) at which location the capsule is heated, and from the vaporization location to second receptacle 52 inside reloading unit 22.

As described hereinabove, for some applications, receptacle 53 of reloading unit 22 houses pushing element 47 and spring 46, which is coupled to the pushing element. For some applications, an upper capsule stopper 50 is used in the upper part of receptacle 53. The upper capsule stopper 50 is configured to limit the upmost position of the upper capsule of the stack within receptacle 53, such that the upper capsule is prevented from blocking or disturbing the movement of capsule-loading mechanism 56.

For some applications, a capsule-loading button 23 is used in order to linearly move capsule-loading mechanism 56. Alternatively or additionally, capsule-loading mechanism 56 is configured to be moved by an electrical motor (not shown) that is controlled by control circuitry inside reloading unit 22.

Reference is now made to FIGS. 8A and 9A, which schematically illustrate capsule-loading mechanism 56 in its initial rest stage, in accordance with some applications of the present invention. At this stage, springs 42 apply force to a capsule-engagement plate 44 of capsule-loading mechanism 56, causing plate 44 to be located at the beginning of its linear travel path (at the right-most position, as shown in FIGS. 8A and 9A). At this position, the capsule-engagement plate is configured to engage the upper-most capsule of the stack of capsules in receptacle 53, ready for the beginning of a new capsule loading cycle.

Reference is now made to FIGS. 8B and 9B, which schematically illustrate capsule-loading mechanism 56 in a second stage of its operation, during the loading of an unused capsule from the top of receptacle 53 inside reloading unit 22, into the vaporization location 54 (FIG. 6) inside vaporizing unit 21. For some applications, in order to reload a new unused capsule into the vaporizing unit 21, button 23 is pressed downwards by the user. For some such applications, button 23 is coupled to a pinion circular gear 43, and the button is configured such that, when button 23 is pressed by the user, its linear downwards motion turns the pinion circular gear 43. For some such applications, a rack linear gear 49 is disposed on capsule-engagement plate 44, and is configured to engage pinion circular gear 43, such that circular movement of pinion circular gear 43 is transformed into a linear motion of capsule-engagement plate 44 from its initial position towards the vaporization location 54 (FIG. 6) inside vaporizing unit 21. The above-mentioned movement of capsule-engagement plate 44 pushes the upper-most unused capsule within receptacle 53 into the vaporization location 54 (FIG. 6) inside vaporizing unit 21. In some cases, a used capsule 51 from a previous vaporization is positioned in the vaporization location prior to the reloading of a new unused capsule. Typically, the capsule-loading mechanism is configured such that insertion of the unused capsule into the vaporization location by the capsule-loading mechanism, pushes used capsule 51 out of the vaporization location toward receptacle 52.

For some applications, as shown, pinion circular gear 43 includes a combination of two circular gears with different radii, such as to create a transformation ratio that reduces the downwards distance through which button 23 must be moved, in order to move capsule-engagement plate 44 from its initial position to its end position, relative to if a single circular gear were to be used.

Reference is now made to FIGS. 8C and 9C, which schematically illustrate capsule-loading mechanism 56 in a final stage of its operation. At this stage, as shown, button 23 is typically fully pressed, capsule-engagement plate 44 has fully placed a new, unused capsule into vaporization location 54 (FIG. 6), ready for heating. Previously used capsule 51 is fully emitted out of vaporizing unit 21 into receptacle 52 and springs 42 are fully compressed. For some applications, as button 23 is released, springs 42 push capsule-engagement plate 44 back to its initial rest point (as shown in FIGS. 8A and 9A). Button 23, which is coupled to capsule-engagement plate 44 by the abovementioned rack and pinion gears, is typically automatically pushed back its initial position by the rack and pinion gears, ready for a new capsule loading cycle.

For some applications, reloading unit 22 includes an indicator 58 (FIG. 1) that indicates to the user how many unused capsules are housed within the reloading unit 22. For some applications, rather than the reloading unit being configured to be refilled, some of the components of smoking device 20 are recyclable and are transferable to an unused reloading unit. For example, a single vaporizing unit 21 could be used with a plurality of reloading units, each of which is configured for single use. For some applications (e.g., applications in which the device is used with *cannabis* that is administered for medicinal purposes), the size of the capsules and/or the amount of plant material in each capsule that is to be provided to a given user may be determined by a healthcare professional. In addition, as described hereinabove, the smoking device is typically programmable, such that, for example, only a certain dosage of the active ingredient may be released per use, per puff, or within a given time period. In this manner, if the plant material that is used inside the smoking device is a regulated substance (e.g., *cannabis*), control over the use of the substance may be maintained. For some applications, the smoking device, the reloading unit, the vaporizing unit, and/or the capsules include identifying marks or tags (e.g., an RFID or a barcode), such as to facilitate regulation and control of the use of the smoking device and the capsule.

For some applications, reloading unit 22 does not include receptacle 52, and previously used capsules are ejected from the vaporization location out of the vaporizing unit without being stored inside the reloading unit. For some applications, button 23 and circular gear 43 are not used and an electrical motor is coupled to capsule-engagement plate 44, such as to generate the linear movement for capsule loading. For some applications, a different type of capsule-loading mechanism is used, mutatis mutandis. For example, a capsule-loading mechanism may be used that is generally similar to any one of the capsule-transfer mechanisms as described in WO 16/147188 to Raichman, which is incorporated herein by reference.

Figure 10:
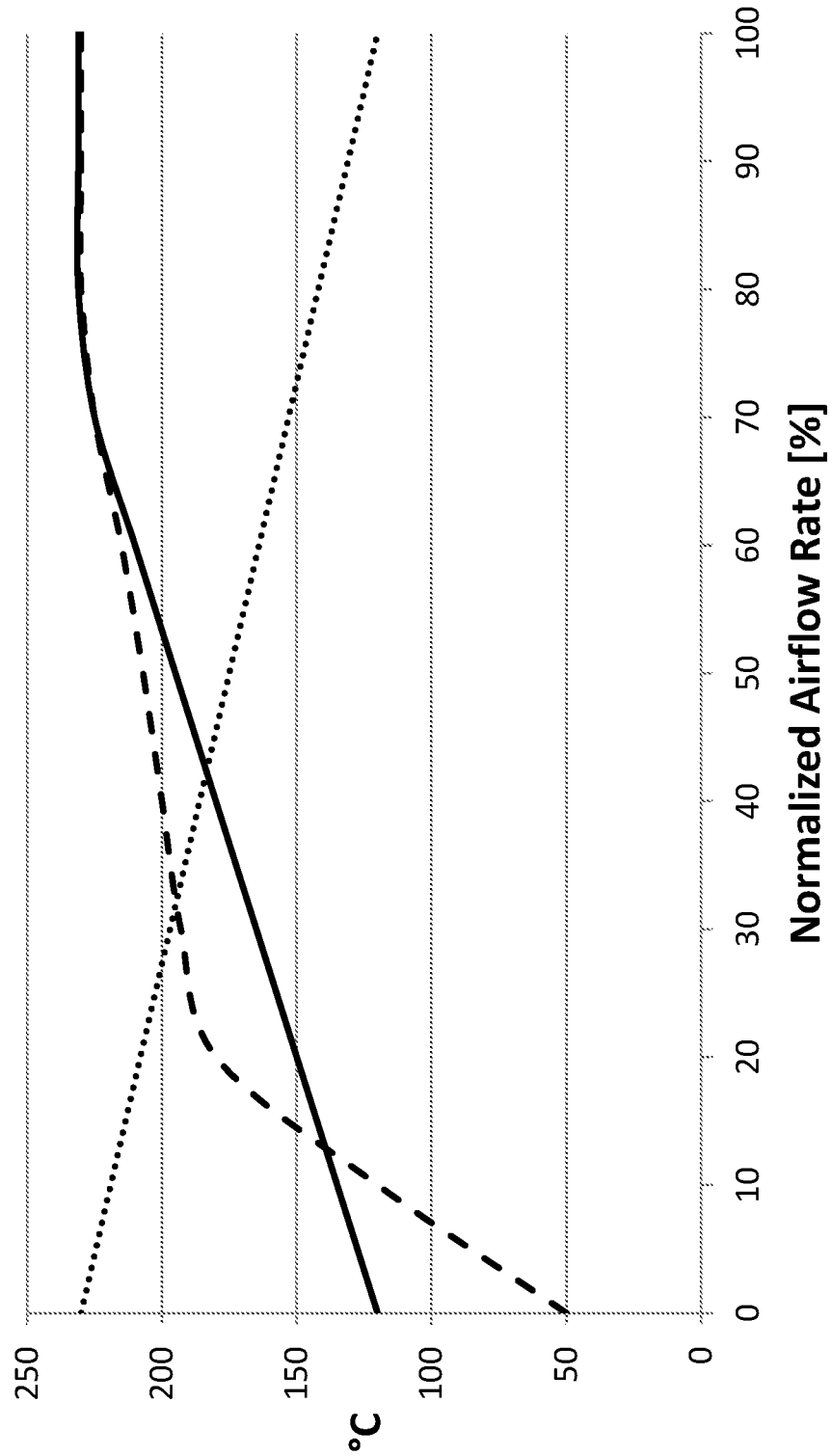
FIG. 10 is a graph illustrating a technique for heating a capsule that contains plant material containing an active ingredient, in accordance with some applications of the present invention.

Reference is now made to FIG. 10, which is a graph with respective curves illustrating respective techniques for heating plant material using a vaporizer, such as vaporizing unit 21, in accordance with some applications of the present invention. The x-axis of the graph indicates normalized airflow rate (measured as a percentage), and the y-axis indicates the temperature (measured in degrees Celsius) to which a capsule that contains a plant material is heated at a given airflow rate. Typically, the airflow rate percentage is measured with reference to a maximal airflow rate that a typical user would generate by inhaling from the vaporizer. By way of example, the airflow rate may be measured as a percentage of an airflow rate of between 0.8 and 1.2 liters per minute.

As described hereinabove, for some applications, vaporizing unit 21 is used to vaporize active ingredients within tobacco. Tobacco typically has a vaporization temperature of 150 to 230 degrees Celsius, and begins to become pyrolyzed at 250 degrees Celsius. Therefore, it is typically desirable to heat the tobacco to a temperature of between 150 degrees Celsius and 230 degrees Celsius. Further typically, it is desirable not to heat the tobacco to a temperature that is greater than 230 degrees Celsius, in order to prevent pyrolysis of the tobacco. Typically, when the vaporizer is used with materials other than tobacco, similar considerations are applicable, although the desired temperature to which the material should be heated will vary depending on the characteristics of the material that is being used with the vaporizing unit.

Mouthfullness is an attribute that smokers refer to that relates to the texture and feel of tobacco smoke in the mouth. While smoking a combustible cigarette, the combustion speed, and therefore the amount and density of the generated smoke are directly related to airflow rate through the cigarette. By controlling of inhalation rate, cigarette smokers can adjust the mouthfullness according to their personal taste and preferences.

For some applications, the feeling of mouthfullness is at least partially replicated when using a vaporizer (for example, vaporizing unit 21) by heating the plant material within the capsule as a function of airflow rate through the vaporizer (for example, air flow through capsule 29 shown in FIG. 6), which is indicative of the inhalation rate of the user. Typically, this enables the user to have control over at least some of the properties of the generated active ingredient vapors.

For some materials (for example, tobacco and *cannabis*), increasing the temperature of the capsule causes an increase in the vaporization rate of the active ingredient, with more vapors being emitted as temperature is set higher. For some materials, increase of vaporization temperature influences the taste of the generated vapors. Some materials (for example, various types of tobacco), when heated to the lower end of their vaporization temperature range, emit light tasted vapors, and when heated to higher temperatures within their vaporization temperature range, generate vapors having a different taste, e.g., more heavy, rich, woody, or smoked.

For some applications, the plant material is initially heated to a temperature point at the lower end of the vaporization temperature range of the plant material. The temperature is then increased within the vaporization temperature range according to a function of the detected inhalation air flow through the vaporizer (e.g., through the capsule of the vaporizer), with the maximum temperature to which the capsule is heated typically being limited, in order not to exceed plant material's pyrolysis temperature. For some applications, the plant material is heated to a lower temperature when lower airflow rate is detected and to a higher temperature when a high airflow rate is detected. For example, the temperature to which the capsule is heated may be increased in direct proportion to increases in the normalized airflow through the vaporizer, as denoted by the solid curve in FIG. 10. Also, as shown by the solid curve of FIG. 10, for some applications, when the capsule is heated to a pre-defined maximal temperature (of approximately 230 degrees Celsius, as shown in FIG. 10), additional heating is withheld, e.g., to avoid reaching the pyrolysis temperature of the plant material.

For some applications, the capsule containing the plant material is initially heated to a temperature point below the lower end of the vaporization temperature range of the plant material. When little to no air flows through the capsule, the sub-vaporization temperature of the plant material will prevent the vaporization of the active ingredient. Upon detection of an increase in airflow rate, the control circuitry rapidly increases the temperature of the plant material to a point within the vaporization temperature range of the plant material. On detection of an additional increase in inhalation air flow, the capsule temperature is adjusted according to the detected airflow rate.

For some applications, in response to receiving a first input at the vaporizer (e.g., in response to the user pressing an ON switch on the vaporizer), the control circuitry of the vaporizer initiates a pre-heating step. Typically, the pre-heating step is a rapid heating step (e.g., a heating step in which the capsule that contains the plant material is heated at a rate of more than 50 degrees Celsius per second, or more than 100 degrees Celsius per second). Further typically, the control circuitry of the vaporizer is configured to terminate the first heating step, by withholding causing further temperature increase of the capsule, in response to detecting that the temperature of the capsule (which is indicative of the temperature of the plant material) has reached a pre-defined first temperature. Typically, the first temperature is more than 80 percent and less than 120 percent of the low end of the plant material vaporization range, e.g., more than 90 percent and less than 110 percent, or more than 85 percent and less than 95 percent, or more than 105 percent and less than 115 percent of the low end of the used active ingredient vaporization temperature range. For example, when the vaporizer is used to vaporize tobacco, the control circuitry of the vaporizer may be configured to withhold causing further temperature increase of the capsule, in response to detecting that the temperature of the capsule has reached a pre-determined temperature that is less than 170 degrees Celsius (e.g., less than 150 degrees Celsius), e.g., a temperature that is between 120 and 130 degrees Celsius, or between 130 and 140 degrees Celsius. For some applications, in response to the detection of airflow through the plant material, the plant material's temperature is increased at a rate of between 0.5 to 10 degrees Celsius per percent of airflow rate increase, e.g., a temperature increase of 0.5 to 2 degrees Celsius, 2 to 8 degrees Celsius, or 5 to 10 degrees Celsius per percent of airflow rate increase.

For some applications, to enable the performing of airflow rate related heating of the plant material, the vaporizer (for example vaporizing unit 21) is configured to enable fast heating of the plant material in order to rapidly adjust the temperature of the plant material to changes in the airflow rate during the inhalation, for example, to enable a temperature increase of more than 20 degrees Celsius per second (e.g., more than 50 or more than 100 degrees Celsius per second). For some applications, the target temperature to which the plant material is heated is dynamically updated in order to adjust the vaporization temperature and vaporization rate according to the desired smoking profile of the user. For some applications, the target temperature to which the plant material is heated is dynamically updated in a continuous manner. For some applications, the capsule is heated to a target a temperature that is derived as a continuous function of the detected airflow rate. For example, the continuous function may be a polynomial function, a monotonically increasing function, a monotonically decreasing function. Alternatively, the target temperature to which the plant material is heated is dynamically updated on a puff-by-puff basis, i.e., with each inhalation of the user, the control circuitry calculates a target temperature to which the capsule should be heated for that inhalation. For some applications, the control circuitry detects that the user is starting to inhale from the vaporizing unit by receiving an input via a user interface located on the reloading unit or the vaporizing unit. Alternatively or additionally, the control circuitry detects that the user is starting to inhale from the vaporizing unit by detecting the temperature of the capsule, and/or by detecting an indication of an amount of energy required to maintain the temperature of the capsule constant.

For some applications, the control circuitry of the vaporizer calculates the airflow rate through the capsule by measuring the electrical power needed to maintain the capsule that houses the plant material at a desired temperature. In order to enable the use of this technique for airflow measurement, the plant material is typically initially heated to a temperature that is above the ambient air temperature, for example to 50 degrees Celsius or more (as shown by the dashed curve in FIG. 10), or to 120 degrees Celsius or more (as shown by the solid curve in FIG. 10). Typically, once the capsule has been heated above the ambient temperature and ambient air is then made to flow through the capsule by the user inhaling, the electrical power needed to maintain the capsule at a given temperature is related to airflow rate and the temperature gradient between the capsule and the flowing ambient air. Therefore, the control circuitry is configured to determine the airflow rate based upon the current temperature of the capsule, and the electrical power needed to maintain the capsule at the temperature. For example, the control circuitry may measure the electrical power needed to maintain the capsule at the temperature by detecting variations in the duty cycle that is used to heat the capsule. For some applications, the temperature of the capsule is not held constant, and the control circuitry determines the airflow rate through the capsule at least partially based upon measured changes in temperature of the capsule resulting from changes in airflow rate through the capsule. For example, the control circuitry may continue to heat the capsule at a fixed power, and measure the changes in temperature of the capsule. Typically, such changes in temperature are indicative of the airflow rate through the capsule. Alternatively, the control circuitry may stop heating the capsule when the capsule is at a given temperature, and measure changes in the temperature of the capsule. Typically, such changes in temperature are correlated with the rate of airflow through the capsule, since the measured change in temperature is indicative of induced heat transfer from the heated capsule to the ambient air, by convection, which, in turn, is indicative of the rate of airflow through the capsule. For some applications, the control circuitry is configured to measure ambient temperature and/or humidity in order to calculate airflow rate in accordance with the technique described herein. Typically, in order to calculate the airflow rate, the control circuitry accounts for the difference between the temperature of the capsule (and therefore the plant material), and the ambient temperature.

For some applications, functions are used to determine the target temperature to which the capsule is heated, based upon the detected airflow rate indication, according to the material in use, the desired user experience or any other relevant factor. For some applications, in addition to airflow rate measurement, inputs are received by the control circuitry from additional sources, in order to determine the target temperature to which to heat the capsule. For example, as described hereinabove, the control circuitry may be configured to classify a capsule as a given capsule type, and to control the heating of the capsule based upon a heating profile that is specifically suited to that capsule type. For example, different types of capsules may have different airflow-rate-to-target-capsule-temperature profiles applied to them. For example, one type of capsule may follow a profile as indicated by the solid curve of FIG. 10, another capsule type may follow a profile as indicated by the dashed curve of FIG. 10, and yet another capsule type may follow a profile as indicated by the dotted curve of FIG. 10. For some applications, a user inputs a desired heating profile, for example, using user interface 10 (shown in FIG. 3).

For some applications, by performing the heating of the capsule in the airflow related process described hereinabove, one or more of the following results are achieved:

1) When smoking a traditional combustion cigarette, an increase in the user's inhalation rate increases generated smoke due to intensification of cigarette flame. In addition, the temperature of the inhaled smoke is typically greater. Therefore, for some applications, the target temperature to which the capsule is heated is correlated to airflow rate (which is indicative of user inhalation rate), in order to simulate the burning of a traditional cigarette as described above. As described hereinabove, typically the capsule is not heated above a predefined maximal temperature limit (which is typically less than 90 percent of the pylorization temperature of the plant material). Typically, the predefined maximal temperature limit is set such that the plant material is not heated to a temperature that is greater than the pyrolysis temperature of the plant material, and/or such that the plant material is not heated to a temperature that will produce smoke and/or a bad taste. By dynamically adjusting the target vaporization temperature as described hereinabove, the taste and "mouthfullness" of the generated vapors are adjusted according to user's individual taste and preferences. For example, users that prefer a long and slow inhalation will benefit from receiving a constant slow supply of the vaporized active ingredient, due to the relatively lower vaporization temperature that will be generated by the lower airflow rate of the slow inhalation. On the other end, users that prefer a faster and more intense release of the active ingredient will enjoy the higher rate of active ingredient vaporization rate that will result from the higher vaporization temperature to which the plant material is heated, due to their elevated inhalation airflow rate.

2) Dynamically adjusting the target temperature to which the plant material is heated as described hereinabove, may provide higher efficiency in the consumption rate of the plant material. For example, users that prefer taking several relatively short puffs will not suffer from loss of plant material between the short puffs, since the control circuitry will lower the target temperature to which the capsule is heated between the puffs.

3) Dynamically adjusting the target temperature to which the capsule is heated as described hereinabove, may reduce loss of active ingredient prior to the beginning of user inhalation. The lack of airflow prior to the user's inhalation will result in the target temperature to which the capsule is heated being relatively low, such as to reduce vaporization of active ingredient prior to user inhalation.

4) In some cases, a delivery of a constant dose of the active ingredient is desired on every puff. For a given arrangement of plant material, the mass of the active ingredient that is vaporized is a function of, at least, the temperature of the material and of the airflow rate through the material. For some applications, an airflow-related heating process is used as described hereinabove, and the control circuitry responds to the measured airflow indication, such as to deliver a constant dose of the active ingredient for each puff of the vaporizing unit. For example, a function may be used in accordance with which the vaporization temperature is reduced in response to the airflow increasing.

5) For some applications, the control circuitry additionally accounts for the amount of active ingredient that has already been vaporized from the portion of the plant material that is currently being heated (which may, for example, be a portion of the plant material that is disposed inside a capsule). For example, in some cases, based on the rates of airflow and temperatures that have already been applied to the capsule that is currently being heated, the control circuitry may determine an amount of the active ingredient that has already been vaporized. For some applications, the control circuitry determines the target temperature to which to heat the capsule, in response to the amount of active ingredient that has already been vaporized. For some applications, the control circuitry determines the target temperature to which to heat the capsule, in response to (a) the amount of active ingredient that has already been vaporized, as well as (b) the current measured airflow through the vaporizing unit (e.g., through the plant material that is being heated within the vaporizing unit). For example, for a given airflow rate, the control circuitry may heat the capsule to a greater temperature, the greater the amount of the active ingredient that has already been vaporized. This may be because, once a given amount of the active ingredient has already been vaporized from the plant material, the plant material may need to be heated to a greater temperature in order for the remaining active ingredient to be vaporized. For some applications, in response to determining that a given amount of the active ingredient has already been released from the plant material, the control circuitry may be configured to reduce the temperature of the plant material to a sub-vaporization temperature, such as to withhold additional vaporization of active ingredient.

For some applications, in response to the detected rate of air flow through the vaporizer, the control circuitry calculates the dosage of the active substance that has been provided to the user. For some applications (e.g., when the vaporizer is used with *cannabis* for medicinal purposes), a healthcare professional inputs instructions into the control circuitry that control the amount of airflow through the vaporizer that is permitted during each use of the vaporizer, and/or the amount of airflow through the vaporizer that is permitted within a given time period (e.g., per hour, or per day, or per puff). Alternatively or additionally, the control circuitry may control the heating rate per unit airflow rate, as described hereinabove. For example, in order to deliver a constant dose of active ingredient to the user, the control circuitry may be configured to decrease the temperature to which the capsule is heated, in response to detecting an increase in the airflow, as indicated by the dotted curve in FIG. 10. For some applications, the decrease in temperature is configured to keep a constant active ingredient vaporization rate. For some applications, the control circuitry combines the aforementioned temperature control functionality with setting a time limit for the heating that is applied in response to each puff of the vaporizer. In this manner, a constant dose is delivered to the user on each puff, regardless of the airflow rate of the puff.

For some applications, in response to detecting that no inhalation has occurred over a given time period (e.g., a time period of between 0.5 seconds and 3 seconds), the temperature of the capsule is reduced to below the vaporization temperature of the plant material. For example, during use of the vaporizer, the user may stop inhaling for a given time period, due to coughing, and/or due to irritation caused by the active ingredient. By reducing the temperature to below the vaporization temperature, wastage of the plant ingredient during this period is reduced.

Referring again to FIG. 10, for some applications a heating profile is applied as indicated by the solid curve. For example, between approximately 0 airflow rate percentage units and 70 airflow rate percentage units the control circuitry causes the temperature of the capsule to be modified along a temperature range of 120 to 230 degrees Celsius. This is performed by detecting the current inhalation airflow rate and adjusting the temperature according to the curve. From approximately 70 airflow rate percentage units to 100 airflow rate percentage units, the capsule maintains a maximal temperature of 230 degrees Celsius. More generally between 0 airflow and a given airflow rate, the control circuitry may control the temperature of the capsule in proportion to the airflow rate, up to a maximum temperature. For some applications, the maximal temperature is between 200 degrees Celsius and 230 degrees Celsius. Beyond the given airflow rate, the control circuitry typically maintains the capsule at the maximum temperature even if the airflow rate increases.

For some applications, a heating profile is applied as indicated by dashed curve in FIG. 10. For example, between 0 airflow rate percentage units and a first given airflow rate (e.g., 20 airflow rate percentage units, as shown in FIG. 10) the control circuitry may increase the temperature of the capsule in response to the increases in airflow rate, at a first rate. Between the first given airflow rate and a second given airflow rate (e.g., 70 airflow rate percentage units, as shown in FIG. 10), the control circuitry may increase the temperature of the capsule in response to the increases in airflow rate, at a second rate. For some applications, the second rate is lower than the first rate, i.e., at the second rate, the temperature increase in response to a given rise in airflow rate is less than the temperature increase that is applied in response to the same airflow rate rise, at the first rate. For some applications, beyond the second given airflow rate, the capsule is maintained at a given maximum temperature (e.g., a temperature of 230 degrees Celsius), even if the airflow rate increases.

As described hereinabove, for some applications, a heating profile is applied as indicated by dotted curve in FIG. 10. For such applications, in response to an increase in the airflow rate, the temperature to which the capsule is heated by the control circuitry is reduced.

Figure 11:
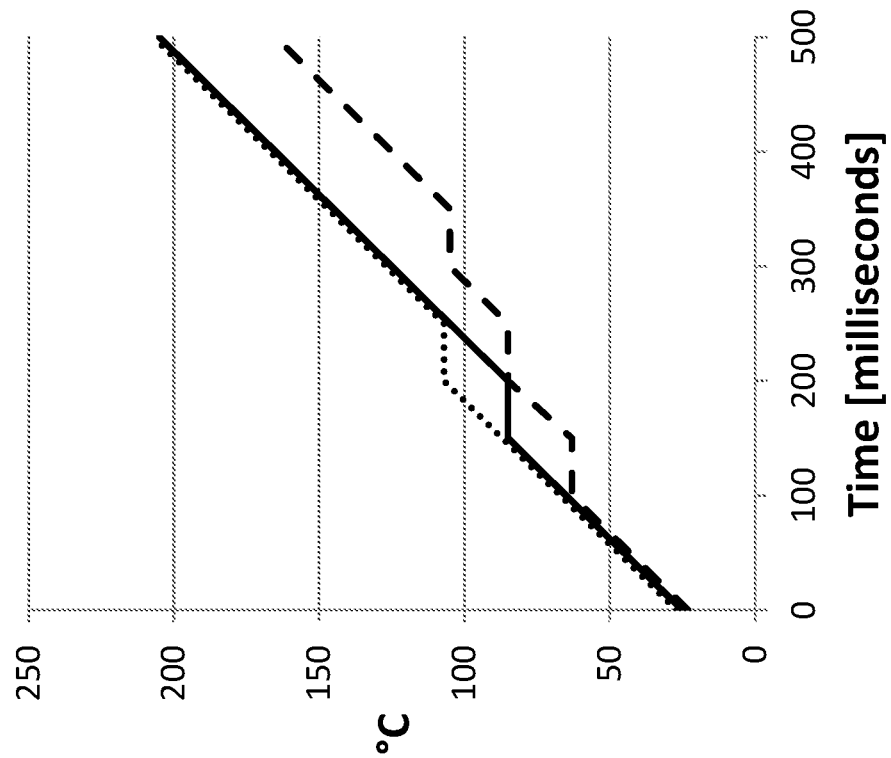
FIG. 11 is a graph illustrating heating curves of capsules containing phase-change materials with different phase-change temperatures, in accordance with some applications of the present invention.

Reference is now made to FIG. 11, which is a graph illustrating the heating curves of capsules that include phase-change materials, in accordance with some applications of the present invention. As described hereinabove, for some applications, in order to enable the identification of the capsule type, use is made of the vaporizing unit's built-in temperature sensor, in combination with phase-change materials that are configured to have respective phase-change temperatures being included within respective capsule types.

The solid curve in FIG. 11 represents the heating curve of a capsule that includes or is thermally coupled to a phase-change material with a phase-change temperature of 85 degrees Celsius. As shown, when applying heat at a constant predefined power to the capsule, the temperature of the capsule rises in proportion with the heating power that is applied. When reaching the phase-change material's phase-change temperature of 85 degrees Celsius (at 150 milliseconds), a large amount of energy in the form of latent heat is accumulated by the phase-change material at a relatively constant temperature, resulting in a detectable pause in the temperature increase of the capsule. For some applications, by detecting the temperature level at which the temporary pause in the temperature increase occurs, the control circuitry classifies the capsule as being a given type of capsule and adjusts the heating profile and/or other relevant functions accordingly. At a certain point in time, when the phase-change material has undergone its phase change, the temperature of the capsule continues to rise due to the applied heat energy, as seen on the solid curve of FIG. 11 after 200 milliseconds.

The dotted curve in FIG. 11 represents the heating curve of a capsule that includes or is thermally coupled to a phase-change material with a phase-change transition temperature of 105 degrees Celsius. The heating curve of the capsule is generally similar to that described with reference to the solid curve, but the temperature level at which the temporary pause in the temperature increase occurs is at a higher temperature of 105 degrees Celsius.

The dashed curve in FIG. 11 represents the heating curve of a capsule that includes or is thermally coupled to a combination of a plurality of different phase-change materials, in accordance with some applications of the present invention. For some applications, the phase-change materials are mixed with each other, or are thermally coupled to each other without being mixed. The dashed curve of FIG. 11 shows an example in which three phase-change materials are used, the materials having phase-change transition temperatures of 65, 85 and 105 degrees Celsius. The heating curve of the capsule is generally similar to that described with reference to the solid curve, but due to the use of phase-change materials with three different phase-change transition temperatures, the heating curve will include three pauses in the temperature increase, each one due to its respective phase-change material reaching its phase changing temperature. By detecting the presence of a pause in temperature increase at pre-defined temperatures, information regarding the type of capsule is coded into the capsule and read by the control circuitry without necessarily requiring the use of a dedicated sensor within vaporizing unit 21, in addition to temperature sensor 35. In this manner, the use of a combination of phase-change materials, each with a different phase changing transition temperature, facilitates a coding method, which is used by the control circuitry for identification of the heated substance.

For some applications, the capsules are used with a phase-change temperature of the phase-change material is higher than 50 degrees Celsius and/or lower than 150 degrees Celsius, e.g., 50 to 150 degrees Celsius, or 80 to 120 degrees Celsius. For some applications, the phase-change material is thermally coupled to the plant material. For example, the phase-change material may be mixed with the plant material. For some applications, sheets of the phase-change material partially or fully cover the plant material.

Figure 12A:
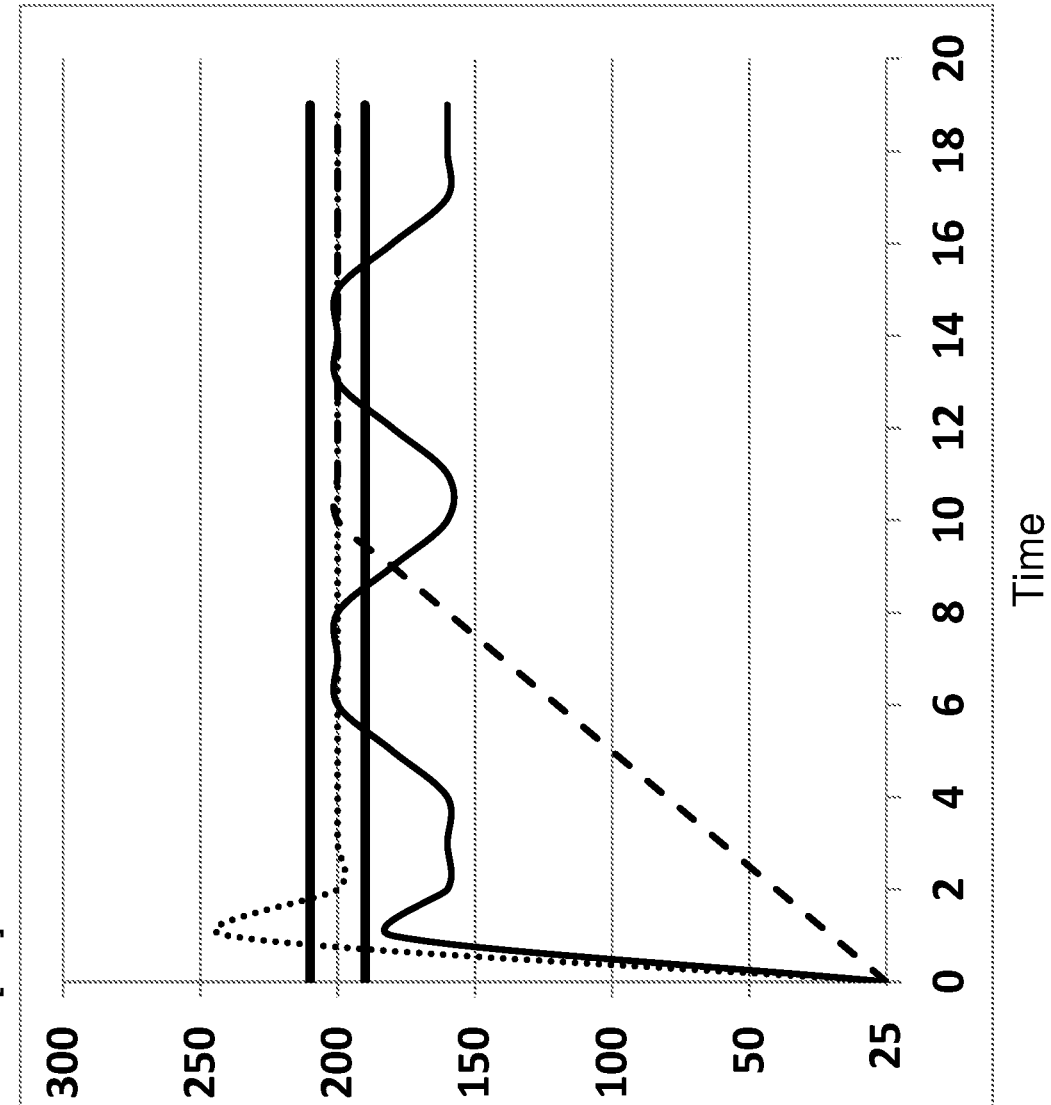
FIG. 12A is a graph illustrating a technique for heating plant material using a vaporizer, in accordance with some applications of the present invention.

Reference is now made to FIG. 12A, which is a graph illustrating respective techniques for heating plant material using a vaporizer, such as vaporizing unit 21, in accordance with some applications of the present invention. The x-axis of the graph indicates time (measured in arbitrary time units), and the y-axis indicates the temperature (measured in degrees Celsius) of a capsule that contains a plant material (and therefore indicates the temperature of the plant material within the capsule), as described herein.

As described hereinabove, for some applications, a vaporizer (such as vaporizing unit 21) is used to vaporize active ingredients within *cannabis*. Cannabis typically has a vaporization temperature of 180 degrees Celsius, and begins to become pyrolyzed at 220 degrees Celsius. Therefore, it is typically desirable to heat the *cannabis* to a temperature of between 190 degrees Celsius and 210 degrees Celsius. The upper and lower boundaries of the desired temperature range to which to heat *cannabis* are denoted on the graph of FIG. 12A, by the two solid horizontal lines at 190 degrees Celsius and 210 degrees Celsius. Further typically, it is desirable not to heat the *cannabis* to a temperature that is greater than the described temperature, in order to prevent pyrolysis of the *cannabis*. Typically, when the vaporizer is used with plant materials other than *cannabis* (e.g., tobacco), similar considerations are applicable, although the desired temperature to which the plant material should be heated will vary depending on the characteristics of the plant material that is being used with the vaporizer.

One possible way of heating the plant material to the desired temperature is via gradual heating, as denoted by the dashed diagonal line, which shows the plant material being heated to the desired temperature over a period of more than 8 time units. Another possible way to heat the plant material is via rapid heating, as denoted by the dotted curve in FIG. 12A. Typically, if the plant material is heated rapidly, then initially there is an overshoot in the temperature to which the plant material is heated. For example, this may be because there is a time lag between when the plant material reaches the desired temperature and when the control circuitry detects that the desired temperature has been reached and withholds causing further temperature increase of the plant material in response to the detected temperature. This is indicated in FIG. 12A, which shows that the dotted curve initially rises above 220 degrees Celsius, before plateauing within the desired temperature range. Due to the overshooting, some of the plant material may become pyrolyzed.

In accordance with some applications of the present invention, a two-stage heating process is applied to plant material within a vaporizer, e.g., as indicated by the solid curve shown in FIG. 12A. Typically, in response to receiving a first input at the vaporizer (e.g., in response to the user pressing an ON switch on the vaporizer), the control circuitry of the vaporizer initiates a first heating step. Typically, the first heating step is a rapid heating step (e.g., a heating step in which the capsule that contains the plant material is heated at a rate of more than 50 degrees Celsius per second, or more than 100 degrees Celsius per second). Further typically, the control circuitry of the vaporizer is configured to terminate the first heating step, by withholding causing further temperature increase of the capsule, in response to detecting that the temperature of the capsule (which is indicative of the temperature of the plant material) has reached a first temperature. Typically, the first temperature is less than 95 percent, e.g., less than 90 percent, or less than 80 percent, of the vaporization temperature of the plant material. For example, when the vaporizer is used to vaporize *cannabis*, the control circuitry of the vaporizer may be configured to withhold causing further temperature increase of the capsule, in response to detecting that the temperature of the capsule has reached a first temperature that is less than 170 degrees Celsius (e.g., less than 160 degrees Celsius), e.g., a temperature that is between 140 and 170 degrees Celsius, or between 150 and 160 degrees Celsius.

By configuring the control circuitry to terminate the first, rapid heating stage as described above, even if there is overshoot, and the temperature of the capsule rises above the temperature at which the first heating stage was programmed to be terminated, the temperature of the capsule will typically still not rise above the pyrolysis temperature of the plant material. For example, as shown in FIG. 12A, the control circuitry has been configured to withhold causing further temperature increase of the capsule in response to detecting that the temperature of the capsule has reached approximately 160 degrees Celsius. Initially (at approximately 1 time unit), there is an overshoot, and the temperature of the capsule reaches approximately 180 degrees Celsius. However, the temperature of the capsule then reaches a plateau of approximately 160 degrees Celsius, at about 2 time units. For some applications, the control circuitry of the vaporizer generates an output to the user to indicate that the first stage of the heating has terminated. For example, the control circuitry may illuminate an indicator light, may cause the vaporizer to vibrate, and/or may emit an audio signal (e.g., a beep).

Subsequently, in response to a second input to the vaporizer, the control circuitry of the vaporizer initiates a second heating step (shown, on the solid curve in FIG. 12A, to begin at approximately 4 time units). Typically, between the end of the first stage of the heating process, and the initiation of the second stage of the heating process, the control circuitry maintains the temperature of the capsule at the first temperature. For some applications, the second stage of the heating is initiated automatically in response to inhalation of air from the vaporizer by a user. Alternatively, the second stage of the heating process may be initiated in response to a different input by the user (e.g., the user pressing the ON button a second time). Further alternatively, the second stage of the heating process may be initiated automatically after the first stage of heating is complete, and an indication (such as an indicator light, a vibration, and/or an audio signal (e.g., a beep)) may be generated to indicate to the user to start inhalation when the target temperature for the second heating stage has been reached.

During the second heating step, the control circuitry typically heats the capsule at a slower rate than during the first stage of the heating process. For example, during the second stage of the heating process, the meshes of the capsules of the vaporizer may be heated at a rate of less than 50 degrees Celsius per second, e.g., less than 40 degrees Celsius per second. As shown in FIG. 12A, during the second stage of the heating process (from 4 time units to 6 time units) the capsule is heated from approximately 160 degrees Celsius to 200 degrees Celsius.

In the second stage of the heating process, the control circuitry is configured to withhold causing further temperature increase of the capsule in response to detecting that the temperature of the capsule is between the vaporization temperature of the plant material and the pyrolysis temperature of the plant material. For example, when the vaporizer is used to vaporize *cannabis*, the control circuitry of the vaporizer is configured to withhold causing further temperature increase of the capsule, in response to detecting that the temperature of the capsule has reached a second temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius.

For some applications, by performing the heating in the two-stage process described hereinabove, one or more of the following results are achieved:

1) By terminating the first (rapid) stage of the heating in response to the temperature of the capsule reaching less than 95 percent of the vaporization temperature, even if the heating overshoots, the plant material is not pyrolyzed, since the plant material is not heated to a temperature that is greater than the pyrolysis temperature.

2) Since the second stage of the heating is performed slowly, there is negligible overshooting in the second stage of the heating process, and therefore the plant material does not get pyrolyzed in the second stage of the heating process.

3) Since, during the first stage of the heating, the plant material has already been heated to a temperature that is relatively close the vaporization temperature, even though the second stage of the heating is slow, the time that is required to heat the plant material to the vaporization temperature, from the initiation of the second heating stage, is relatively short (e.g., less than two seconds).

4) Due to low heat conduction of the plant material, if the plant material is heated rapidly, this can give rise to non-uniform heating of the plant material. This can cause portions of the plant material that are near to the heating element(s) (e.g., the electrode(s)) to be pyrolyzed, and/or portions of the plant material that are further from the heating element(s) not to be vaporized. By withholding further heating of the plant material after the first temperature has been reached, and until the second input is received, heat is able to dissipate through the plant material (during the interim period between the first and second heating stages) before any portion of the plant material has been heated to the vaporization temperature. Furthermore, since the temperature increase during the second stage is relatively small, the temperature increase is able to dissipate through the plant material relatively quickly. Thus, relatively uniform heating of the plant material is achieved, such that most of the active ingredient within the plant material is vaporized, while there is substantially no pyrolysis of the plant material.

For some applications, inhalation from the vaporizer by the user is automatically detected by the control circuitry. After the first stage of the heating, there is typically a large difference between the ambient temperature and the temperature of the capsule that contains the plant material. As described hereinabove, between the end of the first stage of the heating process, and the initiation of the second stage of the heating process, the control circuitry maintains the temperature of the capsule at the first temperature. Since there is a large difference between the ambient temperature and the temperature of the capsule, the energy that is required to maintain the capsule (and the plant material therein) at a constant temperature is greater when the user is inhaling from the vaporizer than when the user is not inhaling. Therefore, for some applications, the control circuitry detects that the user is inhaling from the vaporizer by detecting an indication of an amount of energy that is required to maintain the temperature of the capsule (and the plant material therein) constant. For example, the control circuitry may detect variations in the duty cycle that is used to heat the capsule (and the plant material therein). Alternatively or additionally, the control circuitry may automatically detect that the user is inhaling from the vaporizer by directly detecting the temperature of the capsule. Since, after the first stage of the heating, there is a large difference between the ambient temperature and the temperature of the capsule, airflow through the capsule may cause a measurable change in the temperature of the capsule. As described hereinabove, for some applications, the second stage of the heating process is initiated automatically in response to detecting inhalation from the vaporizer by the user.

For some applications, in response to detecting that no inhalation has occurred over a given time period (e.g., a time period of between 0.5 seconds and 3 seconds), the temperature of the capsule is reduced to below the vaporization temperature of the plant material. For example, during use of the vaporizer, the user may stop inhaling for a given time period, due to coughing, and/or due to irritation caused by the plant material. By reducing the temperature to below the vaporization temperature, wastage of the active ingredient during this period is reduced, such that the user is able to receive the prescribed dosage of the active ingredient.

As indicated by the solid curve in FIG. 12A, between approximately 8 time units and 10 time units the control circuitry causes the temperature of the capsule to be lowered to below the vaporization temperature. This may be performed in response to detecting that no inhalation has occurred over a given time period (as described hereinabove), and/or in response to a user input (e.g., in response to the user pressing a button). From approximately 10 time units to 13 time units, the capsule is heated back to the vaporization temperature. This may be performed in response to detecting that inhalation has resumed and/or in response to a user input (e.g., in response to the user pressing a button). Between approximately 15 time units and 17 time units the control circuitry again causes the temperature of the capsule to be lowered to below the vaporization temperature. This may be performed in response to detecting that no inhalation has occurred over a given time period, and/or in response to a user input (e.g., in response to the user pressing a button).

Figure 12B:
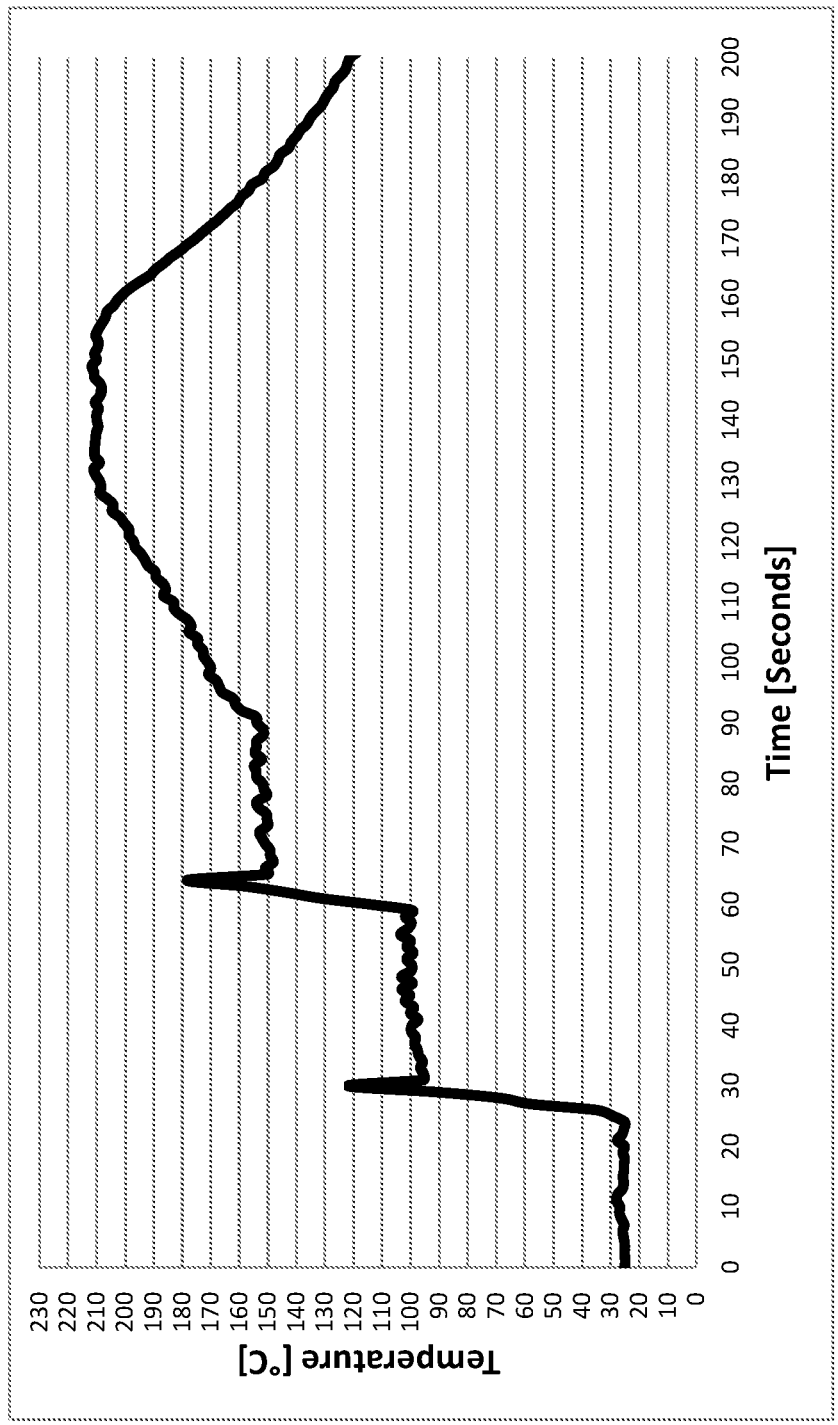
FIG. 12B is a graph illustrating a technique for heating plant material using a vaporizer, in accordance with some applications of the present invention.

Reference is now made to FIG. 12B, which is a graph illustrating a technique for heating plant material using a vaporizer, in accordance with some applications of the present invention. For some applications, a three-stage (or three-step) heating process is applied to plant material within a vaporizer. The second two stages of the heating process are generally similar to those described with reference to the solid curve shown in FIG. 12A. (With respect to FIG. 12B, these stages are referred to, respectively, as the second and third heating stages.) For some applications, an additional, initial stage of heating is applied, in order to remove humidity from the plant material, as shown in FIG. 12B. For example, when the vaporizer is being used with *cannabis*, the vaporizer may apply the following three heating stages to the *cannabis:*

1) Heating to a first temperature that is typically more than 90 degrees Celsius (e.g., more than 100 degrees Celsius) and/or less than 120 degrees Celsius (e.g., less than 110 degrees Celsius, e.g., between 90 degrees Celsius and 120 degrees Celsius (or between 100 and 110 degrees Celsius). For some applications, the plant material is maintained at approximately the first temperature (e.g., the first temperature plus/minus 5 degrees Celsius) for a given time period, for example, in order to remove humidity from the plant material. In FIG. 12B, the first heating stage is shown as being initiated at approximately 28 seconds. Initially, the temperature overshoots, but then is shown to plateau at between approximately 95 degrees Celsius and 105 degrees Celsius. For some applications, the plant material is maintained at approximately the first temperature for a time period of more than 5 seconds, e.g., between 5 and 60 seconds (e.g., approximately 25 seconds, as shown in FIG. 12B). Typically, the first heating step is a rapid heating step (e.g., a heating step in which the capsule that contains the plant material is heated at a rate of more than 50 degrees Celsius per second, or more than 100 degrees Celsius per second). Further typically, the control circuitry of the vaporizer is configured to withhold causing further temperature increase of the capsule, in response to detecting that the temperature of the capsule (which is indicative of the temperature of the plant material) has reached the first temperature.

2) Heating to a second temperature that is typically more than 140 degrees Celsius (e.g., more than 150 degrees Celsius), and/or less than 170 degrees Celsius (e.g., less than 160 degrees Celsius), e.g., between 140 and 170 degrees Celsius (or between 150 and 160 degrees Celsius). This corresponds to the first heating stage shown by the solid curve in FIG. 12A. In FIG. 12B, this stage is shown as being initiated at approximately 63 seconds. Initially, the temperature overshoots, but then is shown to plateau at between approximately 145 degrees Celsius and 155 degrees Celsius. For some applications, the plant material is maintained at approximately the second temperature (e.g., the second temperature plus/minus 5 degrees Celsius) for a given time period. For example, the plant material may be maintained at the second temperature for a time period of more than 5 seconds, e.g., between 5 seconds and 7 minutes.

For some applications, the plant material is maintained at approximately the second temperature for a time period that is sufficient to cause decarboxylation of the *cannabis*, i.e., to convert Tetrahydrocannabinolic Acid (THCA) that is present in the *cannabis* to Tetrahydrocannabinol (THC), and/or to convert Cannabidiolic Acid (CBDa) to Cannabidiol (CBD). For some applications, maintaining the plant material at the second temperature causes the decarboxylation of the *cannabis* in accordance with an article by Dussy et al., entitled "Isolation of Delta9-THCA-A from hemp and analytical aspects concerning the determination of Delta9-THC in *cannabis* products (Forensic Sci Int. 2005 Apr. 20; 149(1): 3-10), which is incorporated herein by reference, and/or an article by Veress et al., entitled "Determination of cannabinoid acids by high-performance liquid chromatography of their neutral derivatives formed by thermal decarboxylation: I. Study of the decarboxylation process in open reactors" (Journal of Chromatography A 520:339-347, November 1990), which is incorporated herein by reference. For example, FIG. 12B shows the plant material being maintained at approximately the second temperature for approximately 25 seconds.

Typically, the second heating step is a rapid heating step (e.g., a heating step in which the capsule that contains the plant material is heated at a rate of more than 50 degrees Celsius per second, or more than 100 degrees Celsius per second). Further typically, the control circuitry of the vaporizer is configured to withhold causing further temperature increase of the capsule, in response to detecting that the temperature of the capsule (which is indicative of the temperature of the plant material) has reached the second temperature.

3) Heating to a third temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius. As shown in FIG. 12B, the third stage of heating is initiated at approximately 90 seconds and continues until approximately 155 seconds.

As described hereinabove, for some applications, the third stage of the heating (which corresponds to the second heating stage shown by the solid curve in FIG. 12A) is initiated automatically in response to inhalation of air from the vaporizer by a user. Alternatively, the third stage of the heating process may be initiated in response to a different input by the user (e.g., the user pressing the ON button a second time). Further alternatively, the third stage of the heating process may be initiated automatically after the second stage of heating is complete, and an indication (such as an indicator light, a vibration, and/or an audio signal (e.g., a beep)) may be generated to indicate to the user to start inhalation when the target temperature for the third heating stage has been reached. During the third heating stage, the control circuitry typically heats the capsule at a slower rate than during the first and second stages of the heating process. For example, during the third stage of the heating process, the meshes of the capsules of the vaporizer may be heated at a rate of less than 50 degrees Celsius per second, e.g., less than 40 degrees Celsius per second. In the third stage of the heating process, the control circuitry is configured to withhold causing further temperature increase of the capsule in response to detecting that the temperature of the capsule is between the vaporization temperature of the plant material and the pyrolysis temperature of the plant material. For example, when the vaporizer is used to vaporize *cannabis*, the control circuitry of the vaporizer is configured to withhold causing further temperature increase of the capsule, in response to detecting that the temperature of the capsule has reached a third temperature that is more than 180 degrees Celsius (e.g., more than 190 degrees Celsius), and/or less than 220 degrees Celsius (e.g., less than 210 degrees Celsius), e.g., a temperature that is between 180 and 220 degrees Celsius, or between 190 and 210 degrees Celsius.

It is noted that, although the three-stage heating process has been described primarily with respect to using *cannabis* as the plant material, the scope of the present invention includes applying a three-stage heating process to other plant materials (e.g., tobacco), mutatis mutandis. The temperatures and time periods that are used in the three-stage heating process when applied to plant materials other than *cannabis* will vary, in accordance with the characteristic vaporization temperatures, pylorization temperatures, and other chemical characteristics of the plant materials.

Figure 14:
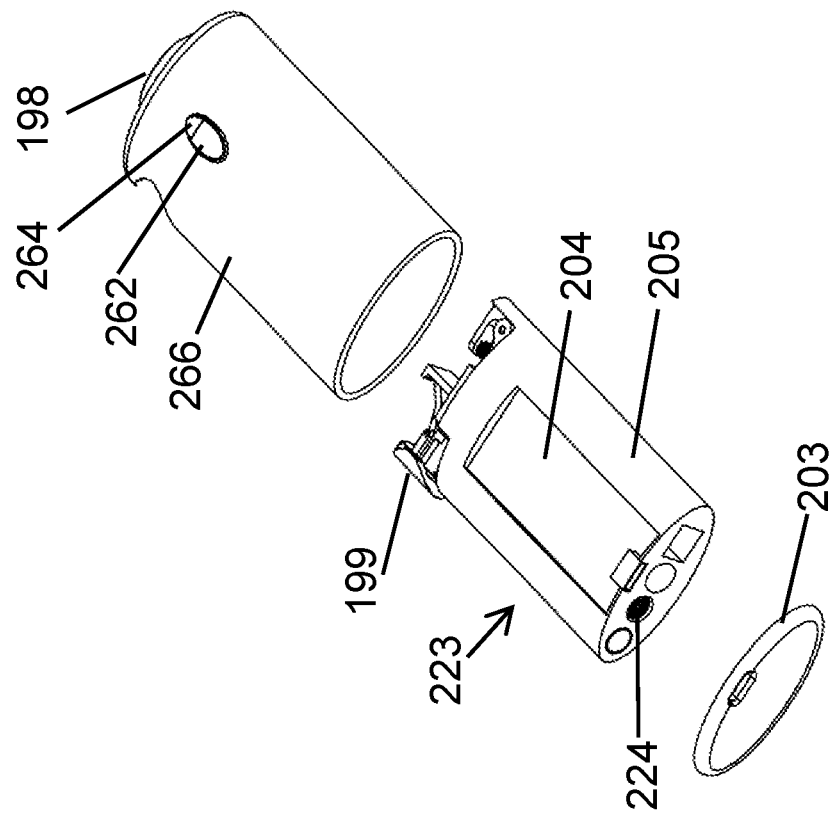
FIG. 14 is a schematic illustration showing an exploded view of the vaporizer of FIG. 13, in accordance with some applications of the present invention.
Figure 13:
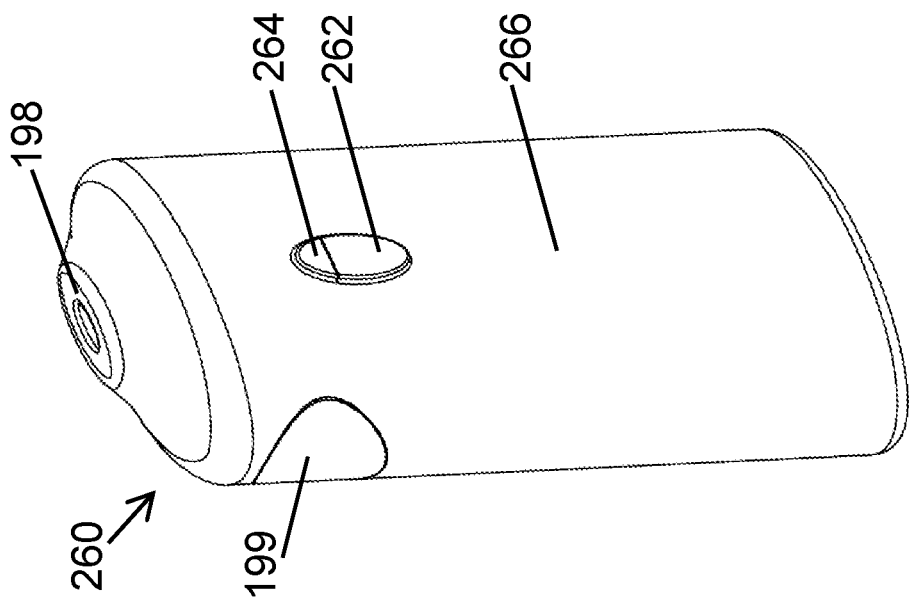
FIG. 13 is a schematic illustration of a vaporizer that is configured to automatically extract a given volumetric dose of a plant material from a mass of the plant material that is disposed in a receptacle of the vaporizer, in accordance with some applications of the present invention.

Reference is now made to FIGS. 13, 14, 15, 16, and 17A-17E, which are schematic illustrations of a vaporizer 260 that is configured to automatically extract a given volumetric dose of a plant material (which, as described hereinabove, contains an active ingredient) from a mass 212 of the plant material that is disposed in the vaporizer (e.g., in a receptacle 224 of the vaporizer), in accordance with some applications of the present invention. FIG. 13 shows a three-dimensional view of a front side the vaporizer. FIG. 14 shows a three-dimensional exploded view of the front side of the vaporizer. FIG. 15 shows a three-dimensional view of a rear side the vaporizer, a mouthpiece 198 of the vaporizer having been removed. FIG. 16 shows a cross-sectional view of the vaporizer. FIGS. 17A-E show cross-sectional views of an extraction mechanism 225 of the vaporizer, at respective stages of the operation of the extraction mechanism.

Typically, vaporizer 260 includes a mouthpiece 198, control circuitry 204, a battery 211, a user interface (e.g. activation button 262, and/or indication LED 264) and a cover 266, 203. Typically, the mass of plant material contains a plurality of volumetric doses of the plant material disposed in a single body, and is not separated into volumetric doses (e.g., by volumetric doses being disposed inside respective, individual capsules, as described hereinabove). For example, as shown in FIG. 18, which shows a cross-sectional view of receptacle 224, a cigarette 212 containing the plant material may be placed inside the receptacle.

Vaporizer 260 typically includes an extraction mechanism 225. In response to a user activating the extraction mechanism, the extraction mechanism is configured to extract a given volumetric dose of the plant material from the mass of plant material. For example, as shown in FIGS. 16 and 17A-E, the extraction mechanism may include a button 199 that is coupled to (or integrally formed with) a pushing surface 270, a blade tip 272 being disposed at a bottom edge of the pushing surface. For example, a blade 220 may be coupled to the underside of an element that defines the pushing surface. When the button is pushed by the user (or the extraction mechanism is activated in a different manner), this causes the extraction mechanism to advance the pushing surface in a single direction (toward the left of the page, as shown in FIG. 16), such that during advancement of the pushing surface, the blade tip cuts off a given volumetric dose of the material from the mass of material and the pushing surface pushes the volumetric dose to a surface 217 (which is typically a mesh), which acts as a vaporization location, as described hereinabove.

As stated hereinabove, FIGS. 17A-E show cross-sectional views of an extraction mechanism 225 of the vaporizer, at respective stages of the operation of the extraction mechanism. For some applications, pushing of button 199 advances hinged wedge 214. As shown in the transition from FIG. 17A to FIG. 17C, the advancement of the hinged wedge causes a hinged mechanism 215 to rotate about its hinge 222, which, in turn, pushes and lifts an upper surface 216 (which is typically a mesh). Typically, upper surface 216 and lower surface 217 are both configured to act as heating surfaces, which are configured to apply heat to a volumetric dose of the plant material, as described hereinbelow. The lifting of the upper surface causes upper surface 216 and lower surface 217 to move apart from one another, thereby creating (or increasing) a gap between the upper and lower surface. The opening of the gap enables pushing surface 270 to advance a volumetric dose to above the lower surface, such that the volumetric dose is disposed between the upper and lower surfaces. Typically, advancement of a volumetric dose into the gap between the upper and lower surfaces causes a used volumetric dose of the plant material to be pushed out from above the lower surface and into a waste receptacle 206.

Referring now to FIG. 17D, for some applications, further pushing of button 199, causes wedge 214 to snap off hinged mechanism 215. Subsequently, button 199 is released by user and retracted (typically, automatically by return spring 213), which in turn retracts pushing surface 270 to its starting position, as shown in FIG. 17E. Retraction of the pushing surface causes spring 209 to push hinged mechanism 215 toward its starting position. In turn, this causes the upper and lower surfaces to clamp the volumetric dose between the surfaces by allowing the upper and lower surfaces to move toward one another.

Referring again to FIG. 16, retraction of the pushing surface to its starting position, allows a spring 210 to push the next volumetric dose of the plant material into position to be cut by blade tip 272. For some applications, spring 210 pushes a pushing element (not shown) against the underside of cigarette 212, which contains the plant material. As described hereinabove, typically, the next time that the vaporizer is used, a used volumetric dose is removed from surface 217, by the next volumetric dose pushing the used volumetric dose off the surface, and into waste receptacle 206.

A heating element is configured to vaporize the at least one active ingredient of the volumetric dose of the plant material by heating the upper and lower surfaces while the volumetric dose is disposed between the surfaces. Typically, surfaces 216 and 217 are meshes, which are heated using control circuitry which drives a current into the meshes, as described hereinabove. (It is noted that control circuitry 204 such as that shown in FIG. 14 is typically housed inside the housing of vaporizer 260.) For some applications, other techniques for heating the plant material (e.g., as described hereinabove) are used. For some applications, a sensor is used to monitor the temperature of the plant material. For example, an optical temperature sensor 208 (shown in FIG. 16), e.g., an infrared temperature sensor as described hereinabove, may be used. For some applications, a two-step process and/or a three-step process is used for heating the plant material, as described hereinabove. For some applications, the temperature to which the plant material is heated is dynamically modified in response to a measured indication of the airflow rate through the plant material that is currently being heated, in accordance with the techniques described hereinabove. For some applications, the airflow rate may be detected by detecting the temperature of mesh 216 and/or mesh 217, in accordance with the techniques described hereinabove, mutatis mutandis.

While the active ingredient is being vaporized, a user typically inhales air via a mouthpiece 198. Air enters the vaporizer 260 through an opening 219 (FIG. 15) and passes through the plant material as illustrated schematically by the dotted arrow in FIG. 16. Vapor from the vaporized plant material is introduced into the air flow.

For some applications, button 199 is additionally configured to cause the vaporizer to operate by being pushed. For example, button 199 may be configured to push against an operating switch (not shown), by being pushed, which may cause the control circuitry to heat the meshes using techniques as described herein.

Figures 20, 21:
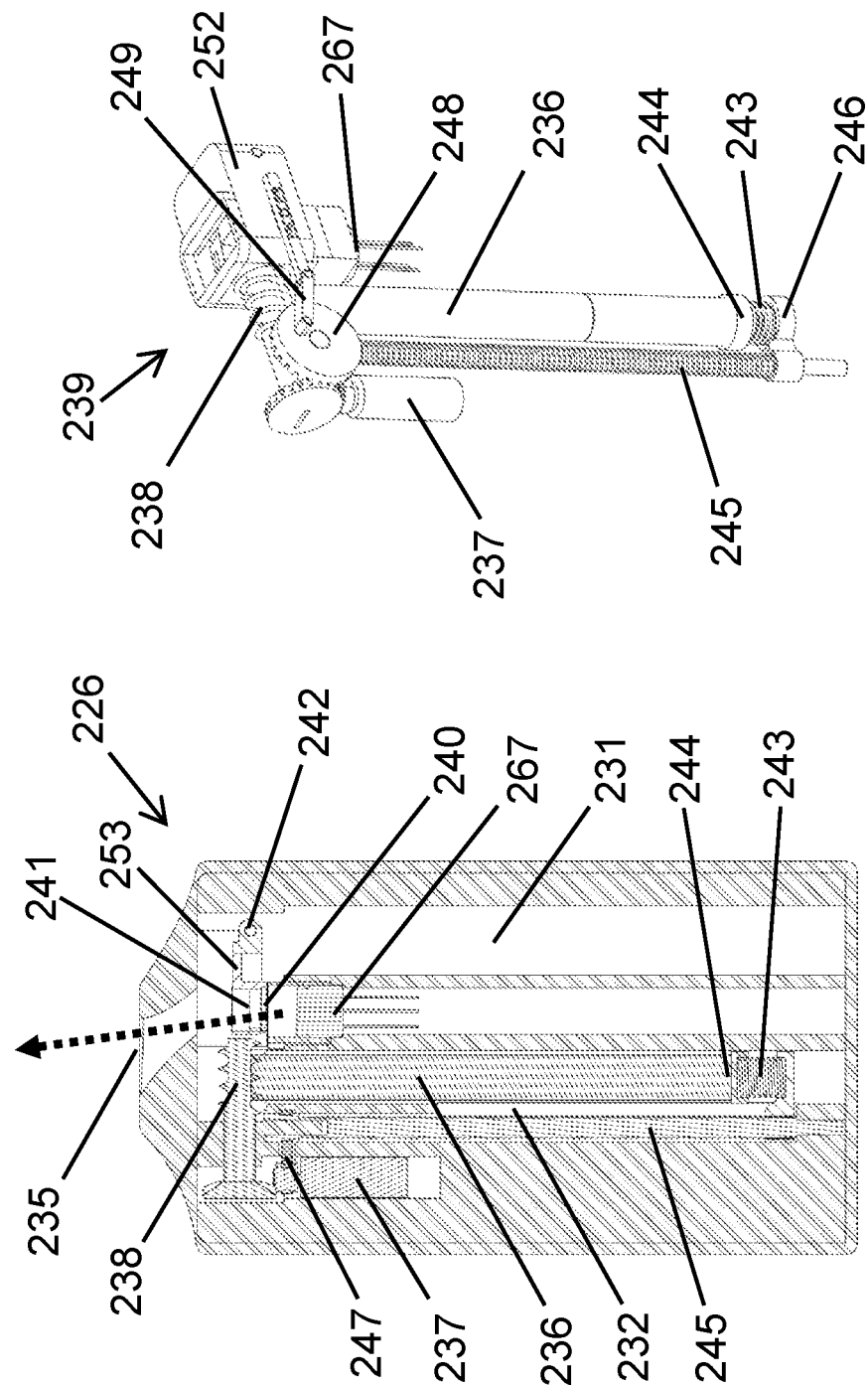
FIG. 20 is a schematic illustration showing a cross-sectional view of the vaporizer of FIG. 18, in accordance with some applications of the present invention.
FIG. 21 is a schematic illustration of an extraction mechanism of the vaporizer of shown in FIG. 18, in accordance with some applications of the present invention.

Reference is now made to FIGS. 18, 19, 20, 21, 22A-B, 23A-B, 24A-B, 25, and 26, which are schematic illustrations of a vaporizer 226 that is configured to automatically extract a given volumetric dose of plant material (which, as described hereinabove, contains an active ingredient) from a mass of the plant material that is disposed in the vaporizer (e.g., in a receptacle 232 of the vaporizer), in accordance with some applications of the present invention. FIG. 18 shows a three-dimensional front view of the vaporizer. FIG. 19 shows an exploded three-dimensional front view of the vaporizer. FIG. 20 shows a cross-sectional view of the vaporizer. FIG. 21 shows a three-dimensional view of an extraction mechanism 239 of the vaporizer. FIGS. 22A and 22B show front and rear views of the extraction mechanism of the vaporizer, during a first stage of the operation of the extraction mechanism. FIGS. 23A and 23B show front and rear views of the extraction mechanism of the vaporizer, during a second stage of the operation of the extraction mechanism. FIGS. 24A and 24B show front and rear views of the extraction mechanism of the vaporizer, during a third stage of the operation of the vaporizer. FIGS. 25 and 26 are schematic illustrations of a wiping element 251 of the extraction mechanism.

Typically, vaporizer 226 includes a mouthpiece 235, control circuitry 229, a battery (not shown), a user interface (e.g. activation button 227, and/or indication LED 228), a body 233 and a cover 234. Typically, the mass of plant material contains a plurality of volumetric doses of the plant material disposed in a single body, and is not separated into volumetric doses (e.g., by volumetric doses being disposed inside respective, individual capsules, as described hereinabove). For example, as shown in FIG. 20, which shows a cross-sectional view of receptacle 232, a cigarette 236 containing the plant material may be placed inside the receptacle.

Vaporizer 226 typically includes an extraction mechanism 239, a three-dimensional view of which is shown in FIG. 21. In response to a user activating the extraction mechanism (e.g., by pushing button 227), the extraction mechanism is configured to extract a given volumetric dose of the plant material from the mass of plant material. For some applications, the extraction mechanism is configured to extract the given volumetric dose of the plant material from the mass of plant material in an automated manner, in response to a user input (e.g., in response to the user pushing button 227). For example, as shown in FIG. 21, the extraction mechanism may include a motor 237 and a grinding element 238. For some applications, the grinding element is a gear driven feed screw, which is driven, by the motor, to advance while rotating. The feed screw is typically configured to work in a similar manner to an Archimedes screw or a transfer screw, whereby due to the geometry of the screw, as the screw advances over a mass of plant material that is pressed on to the screw, the screw grinds off plant material from the mass of plant material. In response to the extraction mechanism being activated by the user, motor 237 is activated, causing the feed screw to turn and to grind off a volumetric dose from the mass of plant material 82 and to push the volumetric dose towards surface 240, which is configured to act as a vaporization location, as described hereinabove.

Extraction mechanism 239 is typically configured to advance the grinding element along an advancement axis, in order for the grinding element to grind the plant material. Referring to FIG. 21, for some applications, a material advancement mechanism is configured to advance the mass of material (e.g., cigarette 236) toward the advancement axis of the grinding element, and the extraction mechanism is configured to synchronize the advancements of the grinding element and the mass of material with one another. For example, motor 237 may be configured, via a transmission belt to turn threaded rod 245, in synchronization with advancing and rotating grinding element 238. Turning the threaded rod lifts platform 246, thereby applying a force to spring 243, cigarette holder 244 and cigarette 236. The application of force to cigarette 236 advances the cigarette toward the axis of advancement of the grinding element with a predetermined force, thereby enabling the grinding element to grind off a volumetric dose from the mass of material.

For some applications, the vaporizer includes a lower heating surface 240 (e.g., a mesh), and an upper heating surface 241 (e.g., a mesh), e.g., as shown in FIG. 20. For some applications, the extraction mechanism is configured to move the upper and lower heating surfaces apart from one another, thereby creating (or increasing) a gap between the upper and lower surfaces. The opening of the gap enables grinding element 238 to advance a volumetric dose onto the lower surface, such that the volumetric dose is disposed between the upper and lower surfaces.

With reference to FIGS. 22A-B, 23A-B, and 24A-B, for some applications the extraction mechanism creates (or increases) the gap between the upper and lower surfaces in the following manner. Activation of motor 237 turns bevel gear 248, which in turn advances a pushrod 249, which is attached, off center, to bevel gear 248. Upper surface 241 (FIG. 20) is defined by the underside of an element 253 that is hinged. As shown in FIGS. 22A-B, in an initial stage of the operation of the extraction mechanism, the upper surface is disposed closely above lower surface 240 (FIG. 20). As shown in FIGS. 23A-B, in a second stage of the operation of the extraction mechanism, hinged element 253, which defines the upper surface, is pushed up by a ball bearing or wheel 254 being pushed between a first ramp 255 (which is coupled to hinged element 253), and a second ramp 256, which is coupled to the lower surface. This creates (or increases) a gap between the upper and lower surfaces. As shown in FIGS. 24A-B, in a third stage of the operation of the extraction mechanism, bevel gear 248 retracts pushrod 249 and ball bearing or wheel 254, which causes hinged element 253 to rotate, such as to cause the upper and lower surfaces to clamp the volumetric dose between the surfaces by the upper and lower surfaces moving to move toward each other. For some applications, a spring (not shown) is configured to cause the hinged element to rotate in the above-described manner.

Referring now to FIG. 25 and FIG. 26, for some applications, extraction mechanism 239 of vaporizer 226 includes a wiping element 251 configured to wipe a used volumetric dose of plant material (i.e., a dose that has already been heated such as to vaporize the active ingredient) that is disposed on surface 240 and to place it in a waste receptacle 231 (shown in FIG. 22). As described hereinabove, for some applications, activation of motor 237 turns bevel gear 248, which in turn advances pushrod 249. For some applications, the pushrod is connected to wiping element 251, and the advancement of the pushrod causes the wiping element to advance over surface 240, such as to wipe the surface in the above-described manner. For some applications, the wiping element is disposed on an axle 258, which passes through wheel or ball bearing or wheel 254, as shown in FIG. 26. The axle is guided by a rail 257 (shown in FIG. 24B), which is disposed above the rear side of surface 240. The rail guides the axle, and thereby guides the wiping element, along the path illustrated by the dashed arrows in FIG. 25. In a first stage of the motion of the wiping element, as the wiping element is advanced over surface 240, the axle is guided along the lower part of rail 257. Prior to the return of the wiping element, after completion of the wiping action and when a new volumetric dose of the plant material is disposed on surface 240, axle 258 is guided into the upper part of rail 257, by ramp 256 pushing wheel or ball bearing or wheel 254 upward. This causes the axle to move in the return direction along the upper part of rail 257. In turn, this causes the wiping element to follow the upper part of the path marked by dashed arrow 250 (FIG. 25). The return of the wiping element along the upper part of path marked by dashed arrow 250, enables the wiping element to be returned to its starting position by being moved above the newly inserted volumetric dose (which was pushed on to the surface 240 by grinding element 238) without disturbing, or pushing back toward the grinding element, the newly inserted volumetric dose.

As described hereinabove, typically, a heating element is configured to vaporize the at least one active ingredient of the volumetric dose of the plant material by heating surface 240 and surface 241. The surfaces are typically meshes, which are heated using control circuitry 229, which drives an electrical current into the meshes, as described hereinabove. (It is noted that control circuitry 229 and a battery charging connector 230 such as that shown in FIG. 19 is typically housed inside the housing of vaporizer 226.) For some applications, other techniques for heating the plant material (e.g., as described hereinabove) are used. For some applications, a sensor is used to monitor the temperature of the plant material. For example, an optical temperature sensor 267 (shown in FIG. 20), e.g., an infrared temperature sensor as described hereinabove, may be used. For some applications, a two-step process and/or a three-step process is used for heating the plant material, as described hereinabove. For some applications, the temperature to which the plant material is heated is dynamically modified in response to a measured indication of the airflow rate through the plant material that is currently being heated, in accordance with the techniques described hereinabove. For some applications, the airflow rate is detected by detecting the temperature of mesh 240 and/or mesh 241, in accordance with the techniques described hereinabove, mutatis mutandis.

While the active ingredient is being vaporized, a user typically inhales air via a mouthpiece 235. Air enters the vaporizer 226 through an opening (not shown) and passes through the plant material as illustrated by dotted arrow on FIG. 20. Vapor from the vaporized plant material is introduced into the air flow.

It is noted that the applications described with reference to FIGS. 13-26, in accordance with which a volumetric dose of the plant material is extracted from a mass of the plant material, may be combined with any of the applications described hereinabove with reference to any one of the other figures, mutatis mutandis. For example, optical temperature sensing (e.g., infrared temperature sensing), a ventilation fan (such as fan 76), a two-step heating process, and/or a three-step heating process as described hereinabove, may be used with the vaporizers shown in FIGS. 13-26. In addition, for some applications, the temperature to which the plant material is heated is dynamically modified in response to a measured indication of the airflow rate through the plant material that is currently being heated, in accordance with the techniques described hereinabove. For some applications, the airflow rate is detected by detecting the temperature of heated meshes, in accordance with the techniques described hereinabove, mutatis mutandis.

For some applications, the vaporizers described herein include one or more of the following elements:

For some applications, the mass of plant material is cut or partially cut to predefined volumetric doses, in order to facilitate the extraction of volumetric doses from the mass of material. For example, the mass of material may be in the form of a cigarette, and the rolling paper of the cigarette may be perforated at predefined intervals. The predefined intervals at which the rolling paper of the cigarette is perforated may be configured to correspond to the height of a portion of the extraction mechanism that is configured to extract the volumetric dose, e.g. the height of surface 270 (shown in FIG. 16).

For some applications, an air pump is configured to drive air through the plant material at a pre-determined rate and/or volume, during the heating process, For some applications, a high thermal mass inert material (e.g. glass, metal beads or other) is placed inside the plant material (e.g., a mass of plant material, such as a cigarette), in order to facilitate heating of the plant material.

For some applications, the vaporizer includes a thermistor.

For some applications, the meshes described herein (e.g., meshes of heating surfaces, and or meshes of capsules) are coupled to other components using ultrasonic welding or heat pressing of the mesh to the other components. For some applications, electrical conductors are coupled to meshes that are used as heating surfaces, using ultrasonic welding or heat pressing. For some applications, this facilitates electrical coupling between the electrical conductors and the meshes.

Figure 27A:
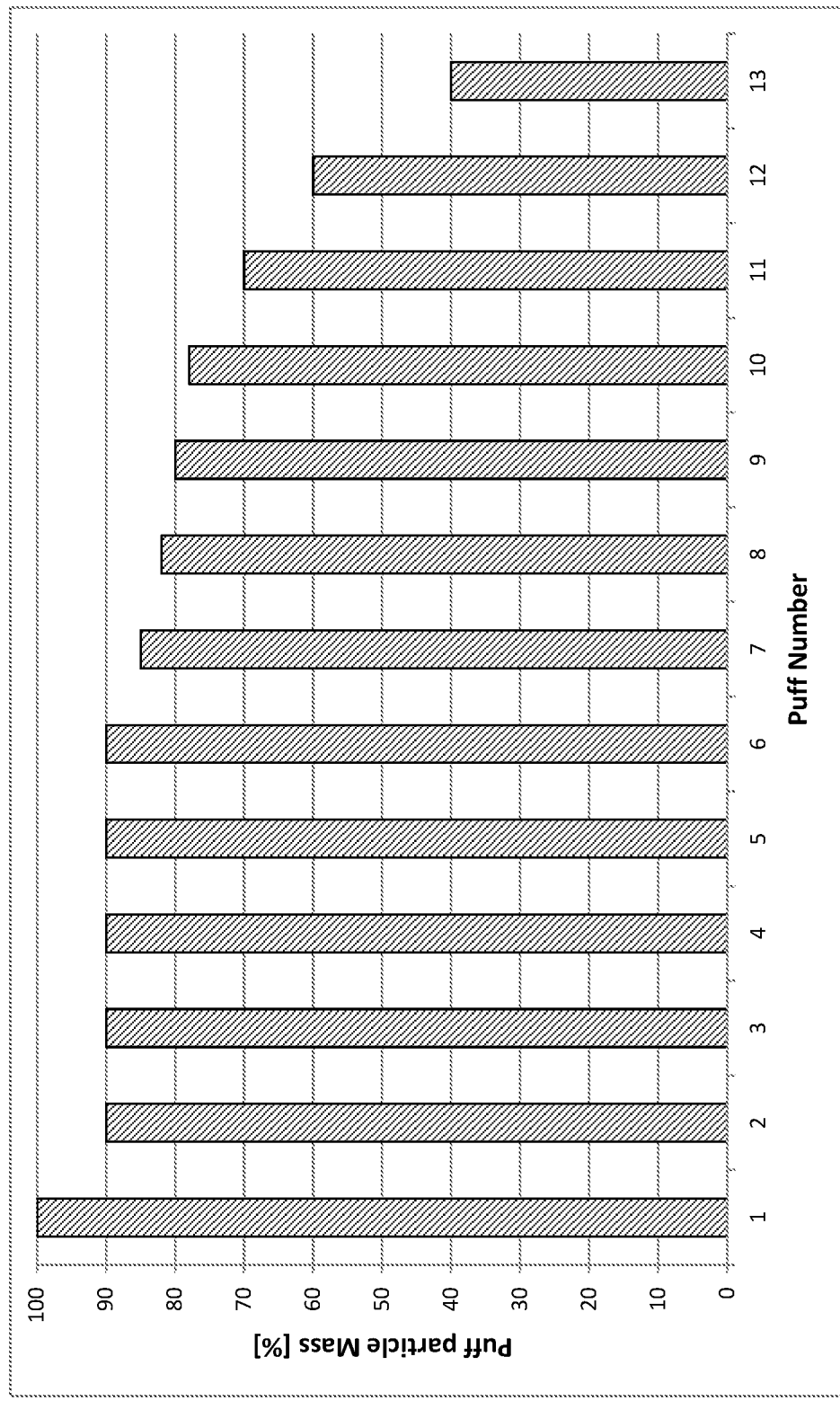
FIGS. 27A and 27B are bar charts showing the mass of active ingredient that is released from plant material with respective, successive puffs of a vaporizer, in accordance with some applications of the present invention.
Figure 27B:
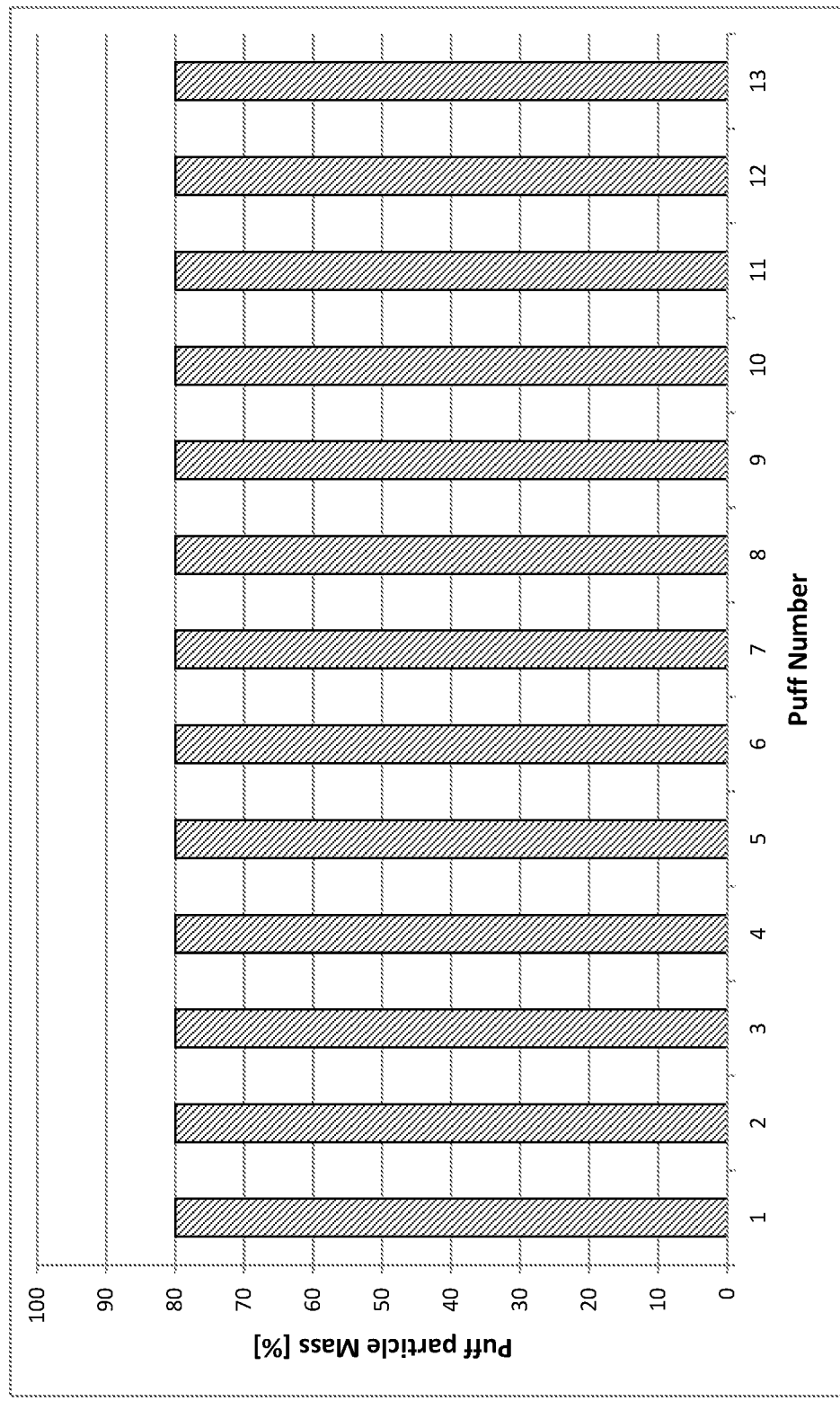

Reference is now made to FIGS. 27A and 27B, which are bar charts showing the mass of active ingredient that is released from plant material with respective, successive puffs of vaporizer, in accordance with some applications of the present invention. The y-axis of the bar charts measures the mass of active ingredient that is released from the plant material as a percentage of a given arbitrary mass. The bar charts show the mass of active ingredient that is released from plant material during each of the puffs, assuming that the total airflow through the capsule during each of the puffs is the same as each other.

FIG. 27A shows an example of the mass of active ingredient that is released from plant material during each of the puffs, if the capsule is heated to the same temperature during each of the puffs. As shown, during successive puffs, the mass of active ingredient that is released from plant material during successive puffs decreases, because with each successive puff, more of the active ingredient has already been released from the plant material, such that there is less of the active ingredient available to be released.

As described hereinabove, for some applications, the control circuitry accounts for the amount of active ingredient that has already been vaporized from the portion of the plant material that is currently being heated (which may, for example, be a portion of the plant material that is disposed inside a capsule). For example, in some cases, based on the rates of airflow and temperatures that have already been applied to the capsule that is currently being heated, the control circuitry may determine an amount of the active ingredient that has already been vaporized. For some applications, the control circuitry determines the target temperature to which to heat the capsule, in response to the amount of active ingredient that has already been vaporized. For example, for a given airflow rate, the control circuitry may heat the capsule to a greater temperature, the greater the amount of the active ingredient that has already been vaporized.

FIG. 27B shows an example of the mass of active ingredient that is released from plant material during successive puffs, in accordance with such applications. As shown, the mass of active ingredient that is released from plant material during successive puffs remains constant, because the control circuitry increases the temperature to which the plant material is heated, such as to account for the fact that, with each successive puff, more of the active ingredient has already been released from the plant material. In this manner, when the user is smoking a given portion of plant material (e.g., a given capsule), the experience is more similar to that of smoking a combustible cigarette, in that, when smoking a combustible cigarette, for any given inhalation airflow rate, there is no (or negligible) change in the strength, flavor, and/or mouthfullness of the smoke between the beginning of the cigarette and the end of the cigarette. Similarly, by the control circuitry of the vaporizer accounting for the fact that, with each successive puff, more of the active ingredient has already been released from the plant material, it is the case that, for any given inhalation airflow rate, there is no (or negligible) change in the strength, flavor, and/or mouthfullness of the vapors that are generated by the vaporizer between the beginning of the use of the portion of plant material (e.g., the capsule), and the end of use of the portion of plant material.

In general, the scope of the present application includes combing the apparatus and methods described herein with apparatus and methods described in WO 16/147188 to Raichman, and/or US 2016/0271347 to Raichman, both of which applications are incorporated herein by reference.

There is provided, in accordance with some applications of the present invention, the following inventive concepts:

Inventive concept 1. Apparatus for use with a vaporizer that is configured vaporize an active ingredient from a material that contains the active ingredient, the apparatus comprising:
  a capsule configured to be heated by the vaporizer, the capsule comprising:
    a portion of the material that contains the active ingredient; and
    perforated sheets disposed around the portion of the material, the perforated sheets defining perforations therethrough that are such as to guide airflow through the capsule along a predefined airflow path.

Inventive concept 2. Apparatus for use with a material that contains an active ingredient, the apparatus comprising:
  a capsule comprising:
    a portion of the material that contains the active ingredient; and
    sheets disposed around the portion of the material; and
  a vaporizer configured to receive the capsule, and to vaporize the active ingredient by heating the portion of the material within the capsule, the vaporizer comprising:
    a perforating mechanism that is configured to perforate the sheets prior to the plant material being heated inside the vaporizer.

Inventive concept 3. Apparatus for use with a plurality of capsules containing a material that contains an active ingredient, the apparatus comprising:
  a smoking device comprising:
    a vaporizing unit comprising a heating element configured, while each of the capsules is disposed at a vaporization location within the vaporizing unit, to cause the active ingredient of the material within the capsule to become at least partially vaporized by individually heating the capsule; and
    a reloading unit that:
      is reversibly couplable to the vaporizing unit,
      is shaped to define at least a first receptacle that is shaped to house the plurality of capsules in a stacked configuration, and
      comprises a capsule-loading mechanism configured, when the reloading unit is in a coupled state with respect to the vaporizing unit, to individually transfer each of the capsules from the first receptacle within the reloading unit to the vaporization location within the vaporizing unit.

Inventive concept 4. The apparatus according to inventive concept 3, wherein the reloading unit comprises a plurality of reloading units, each of the reloading units being configured for a single use, and wherein the vaporizing unit is configured to be reversibly couplable to each the plurality of reloading units.

Inventive concept 5. The apparatus according to inventive concept 3, wherein the capsule-loading mechanism is configured, by transferring a capsule from the first receptacle within the reloading unit to the vaporization location within the vaporizing unit, to eject a used capsule from the vaporization location within the vaporizing unit to outside the smoking device.

Inventive concept 6. The apparatus according to inventive concept 3, wherein the reloading unit comprises at least one power supply, and wherein the vaporizing unit comprises at least one power supply, and the power supply of the reloading unit is configured to charge the power supply of the vaporizing unit.

Inventive concept 7. The apparatus according to any one of inventive concepts 3-6, wherein the reloading unit is shaped to define a second receptacle that is shaped to house the plurality of capsules in stacked configurations, and wherein the capsule-loading mechanism is configured, when the reloading unit is in a coupled state with respect to the vaporizing unit, to individually transfer each of the capsules from the vaporization location within the vaporizing unit to the second receptacle within the reloading unit.

Inventive concept 8. The apparatus according to inventive concept 7, wherein, when the reloading unit is in a coupled state with respect to the vaporizing unit, the first and second receptacles and the vaporization location are configured to be linearly aligned with each other, and wherein the capsule-reloading mechanism comprises a linear capsule-loading mechanism, configured to move each of the capsules by moving linearly.

Inventive concept 9. A method comprising:
coupling a vaporizing unit and a reloading unit of a smoking device to each other,
the vaporizing unit including a vaporization location, and
the reloading unit being shaped to define at least a first receptacle that is shaped to house, in a stacked configuration, a plurality of capsules, each of the capsules including a material that contains an active ingredient;
using a capsule-loading mechanism, individually transferring a first one of the capsules from the first receptacle within the reloading unit to the vaporization location within the vaporizing unit; and
when the first capsule is disposed at the vaporization location within the vaporizing unit, causing the active ingredient within the material within the first capsule to become at least partially vaporized by individually heating the capsule.

Inventive concept 10. The method according to inventive concept 9, wherein transferring the first one of the capsules from the first receptacle within the reloading unit to the vaporization location within the vaporizing unit comprises ejecting a used capsule from the vaporization location within the vaporizing unit to outside the smoking device.

Inventive concept 11. The method according to inventive concept 9, wherein the reloading unit includes at least one power supply, and the vaporizing unit includes at least one power supply, the method further comprising, while the vaporizing unit is in a coupled state with respect to the loading unit, using the power supply of the reloading unit to charge the power supply of the vaporizing unit.

Inventive concept 12. The method according to any one of inventive concepts 9-11, wherein the reloading unit is shaped to define a second receptacle that is shaped to house the plurality of capsules in stacked configurations, the method further comprising using the capsule-loading mechanism individually transferring the first capsule from vaporization location within the vaporizing unit to the second receptacle within the reloading unit.

Inventive concept 13. The method according to inventive concept 12, wherein coupling the vaporizing unit and the reloading unit of to each other comprises coupling the vaporizing unit and the reloading unit of to each other, such that the first and second receptacles and the vaporization location are linearly aligned with each other, and wherein individually transferring the first one of the capsules from the first receptacle within the reloading unit to the vaporization location within the vaporizing unit comprises moving the capsule-loading mechanism linearly.

Inventive concept 14. Apparatus for use with a plant material that includes at least one active ingredient, the apparatus comprising:
a vaporizing unit comprising:
a heating element configured to vaporize the at least one active ingredient of a portion of the plant material that is disposed at a vaporization location within the vaporizing unit, by heating the portion of the plant material;
a sensor configured to detect an indication of airflow rate through the vaporizing unit that is generated by a user; and
control circuitry configured:
to receive the indication of the airflow rate through the vaporizing unit from the sensor,
to measure an amount of heating that the portion of the plant material has already undergone,
at least partially based upon the measured indication of the airflow rate and the amount of heating that the portion of the plant material has already undergone, to determine a temperature to which to heat the portion of the plant material; and
to drive the heating element to heat the portion of the plant material to the determined temperature.

Inventive concept 15. A method for use with a vaporizing unit that is configured to vaporize at least one active ingredient of a plant material, the method comprising:
vaporizing at least one active ingredient of at least a portion of a plant material disposed in the electronic cigarette by heating the portion of the plant material;
measuring an indication of airflow rate through the vaporizing unit generated by a user;
measuring an amount of heating that the portion of the plant material has already undergone;
at least partially based upon the measured indication of the airflow rate and the amount of heating that the portion of the plant material has already undergone, determining a temperature to which to heat the portion of the plant material; and
heating the portion of the plant material to the determined temperature.

Inventive concept 16. A method for use with a vaporizer that vaporizes at least one active ingredient of a material, the method comprising:
detecting an indication of a temperature of the material; and
sequentially:
heating the material, in a first heating step;
in response to detecting an indication that the temperature of the material is at a first temperature, withholding causing further temperature increase of the material, and maintaining the temperature of the material at approximately the first temperature for more than 5 seconds;
further heating the material in a second heating step;
in response to detecting an indication that the temperature of the material is at a second temperature that greater than the first temperature and that is less than 95 percent of a vaporization temperature of the active ingredient, withholding causing further temperature increase of the material, and maintaining the temperature of the material at approximately the second temperature for more than 5 seconds; and
heating the material to the vaporization temperature of the active ingredient, in a third heating step.

Inventive concept 17. Apparatus for use with a material that contains an active ingredient, the apparatus comprising:
a vaporizer comprising:
a heating element configured to vaporize the at least one active ingredient of a material by heating the material;
a temperature sensor configured to detect an indication of a temperature of the material; and
control circuitry configured, sequentially, to:
drive the heating element to heat the material, in a first heating step;
in response to receiving an indication from the temperature sensor that the temperature of the material is at a first temperature, withhold the heating element from causing further temperature increase of the material, and maintaining the temperature of the material at approximately the first temperature for more than 5 seconds;

drive the heating element to further heat the material in a second heating step;

in response to receiving an indication from the temperature sensor that the temperature of the material is at a second temperature that greater than the first temperature and that is less than 95 percent of a vaporization temperature of the active ingredient, withhold the heating element from causing further temperature increase of the material, and maintaining the temperature of the material at approximately the second temperature for more than 5 seconds; and drive the heating element to heat the material to the vaporization temperature of the active ingredient, in a third heating step.

Inventive concept 18. A method comprising:

providing a vaporizer that is configured to hold a material that contains at least one active ingredient;

activating a heating element within the vaporizer to cause the active ingredient within the material to become at least partially vaporized by the heating element heating the material;

detecting an indication of a temperature of the material, using a temperature sensor; and ventilating a space between the material and the temperature sensor, using a fan.

Inventive concept 19. Apparatus for use with a material that contains an active ingredient, the apparatus comprising:

a vaporizer comprising:
 a heating element configured to vaporize the at least one active ingredient of a material by heating the material;
 a temperature sensor configured to detect an indication of a temperature of the material; and
 a fan configured to ventilate a space between the material and the temperature sensor.

Inventive concept 20. Apparatus comprising:

a vaporizer configured to accommodate a mass of material that contains an active ingredient, the vaporizer comprising:
 upper and lower heating surfaces;
 an extraction mechanism configured:
  in response to being activated, to move the upper and lower heating surfaces apart from one another, to extract a given volumetric dose of the material from the mass of material, and to place the volumetric dose between the upper and lower surfaces; and
  subsequently, to cause the upper and lower surfaces to clamp the volumetric dose between the surfaces by allowing the upper and lower surfaces to move toward each other; and
 a heating element configured to vaporize the at least one active ingredient of the volumetric dose of the material by heating the upper and lower surfaces while the volumetric dose is clamped between the upper and lower surfaces.

Inventive concept 21. A method comprising:

providing a vaporizer configured to accommodate a mass of material that contains an active ingredient, the vaporizer including upper and lower heating surfaces, a heating element, and an extraction mechanism;

activating the extraction mechanism to:
 move the upper and lower heating surfaces apart from one another, to extract a given volumetric dose of the material from the mass of material, and to place the volumetric dose between the upper and lower surfaces; and
 subsequently, to cause the upper and lower surfaces to clamp the volumetric dose between the surfaces by allowing the upper and lower surfaces to move toward each other; and while the volumetric dose is clamped between the upper and lower surfaces, to activate the heating element to vaporize the at least one active ingredient of the volumetric dose of the material by heating the upper and lower surfaces.

Inventive concept 22. Apparatus comprising:

a vaporizer configured to accommodate a mass of material that contains an active ingredient, the vaporizer comprising:
 a surface;
 an extraction mechanism comprising a grinding element, the extraction mechanism being configured, in response to being activated, to drive the grinding element to grind off a given volumetric dose of the material from the mass of material and place the volumetric dose upon the surface; and
 a heating element configured to vaporize the at least one active ingredient of the volumetric dose of the material by heating the surface while the volumetric dose is disposed upon the surface.

Inventive concept 23. The apparatus according to inventive concept 22, wherein:

the extraction mechanism is configured to drive the grinding element by advancing the grinding element along an advancement axis, the apparatus further comprises a material advancement mechanism that is configured to advance the mass of material toward the advancement axis of the grinding element, and the extraction mechanism is configured to synchronize the advancements of the grinding element and the mass of material with one another.

Inventive concept 24. A method comprising:

providing a vaporizer configured to accommodate a mass of material that contains an active ingredient, the vaporizer including a surface, a heating element, and an extraction mechanism that includes a grinding element;

activating the extraction mechanism to drive the grinding element to grind off a given volumetric dose of the material from the mass of material and place the volumetric dose upon the surface; and while the volumetric dose is disposed upon the surface, activating the heating element to vaporize the at least one active ingredient of the volumetric dose of the material by heating the surface.

Inventive concept 25. The method according to inventive concept 24, wherein activating the extraction mechanism to drive the grinding element to grind off a given volumetric dose of the material from the mass of material comprises:

advancing the grinding element along an advancement axis;

activating a material advancement mechanism to advance the mass of material toward the advancement axis of the grinding element; and synchronizing the advancements of the grinding element and the mass of material with one another.

Inventive concept 26. Apparatus comprising:

a vaporizer configured to accommodate a mass of material that contains an active ingredient, the vaporizer comprising:

a surface;
an extraction mechanism comprising a pushing surface and a blade tip disposed at a bottom edge of the pushing surface, the extraction mechanism being configured, in response to being activated, to advance the pushing surface in a single direction, such that during advancement of the pushing surface, the blade tip cuts off a given volumetric dose of the material from the mass of material and the pushing surface pushes the volumetric dose onto the surface; and
a heating element configured to vaporize the at least one active ingredient of the volumetric dose of the material by heating the surface while the volumetric dose is disposed upon the surface.

Inventive concept 27. A method comprising:
providing a vaporizer configured to accommodate a mass of material that contains an active ingredient, the vaporizer including a surface, a heating element, and an extraction mechanism that includes a pushing surface and a blade tip disposed at a bottom edge of the pushing surface;
activating the extraction mechanism to advance the pushing surface in a single direction, such that during advancement of the pushing surface, the blade tip cuts off a given volumetric dose of the material from the mass of material and the pushing surface pushes the volumetric dose onto the surface; and
while the volumetric dose is disposed upon the surface, activating the heating element to vaporize the at least one active ingredient of the volumetric dose of the material by heating the surface.

Inventive concept 28. Apparatus comprising:
a vaporizer configured to accommodate a mass of material that contains an active ingredient, the vaporizer comprising:
a surface;
a wiping element; and
an extraction mechanism configured, in response to being activated, to extract an unused volumetric dose of the material from the mass of material and place the unused volumetric dose upon the surface;
a heating element configured to vaporize the at least one active ingredient of the unused volumetric dose of the material by heating the surface while the unused volumetric dose is disposed upon the surface,
the extraction mechanism being further configured, in response to being activated, to drive the wiping element to wipe from the surface a used volumetric dose of the material that has already been heated.

Inventive concept 29. A method comprising:
providing a vaporizer configured to accommodate a mass of material that contains an active ingredient, the vaporizer including a surface, a heating element, a wiping element, and an extraction mechanism;
activating the extraction mechanism:
to extract an unused volumetric dose of the material from the mass of material and place the unused volumetric dose upon the surface, and
to thereby drive the wiping element to wipe from the surface a volumetric dose of the material that has already been used; and
while the unused volumetric dose is disposed upon the surface, activating the heating element to vaporize the at least one active ingredient of the unused volumetric dose of the material by heating the surface.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A device, comprising:
at least one capsule including
a material containing at least one active ingredient,
a first covering layer and a second covering layer configured to cover the material, the first covering layer and the second covering layer opposing each other and being configured to direct an airflow into the first covering layer, through at least a portion of the material, and out of the second covering layer during an operational use of the at least one capsule, the first covering layer and the second covering layer each include a non-perforated sheet configured to be perforated to respectively define a first series of airflow paths and a second series of airflow paths on either side of the material prior to a heating of the at least one capsule, the first covering layer and the second covering layer being configured to direct the airflow into the at least one capsule into the first covering layer in a first direction, cause at least some of the airflow to be directed through the material in a second direction and exit the second covering layer in a third direction, the first direction and the third direction being parallel to each other, the second direction being substantially perpendicular to the first direction and the third direction, the first series of airflow paths and the second series of airflow paths being unaligned with each other, and
an internal heating element within the at least one capsule, the internal heating element directly contacting at least a portion of the material;
control circuitry configured to perform a classification of a type of the at least one capsule and to implement the heating of the at least one capsule via the internal heating element based on the classification to at least partially vaporize the at least one active ingredient of the material; and
a perforating mechanism, the perforating mechanism being configured to perforate the non-perforated sheet of the first covering layer and the second covering layer to respectively define the first series of airflow paths and the second series of airflow paths.

2. The device of claim 1, wherein the first covering layer and the second covering layer each include a mesh configured to receive an electric current to further implement the heating.

3. The device of claim 1, wherein the first covering layer and the second covering layer are each configured to receive an electric current to further implement the heating.

4. The device of claim 1, wherein the material comprises a plant material.

5. The device of claim 1, wherein the control circuitry is configured
to measure an indication of an airflow rate through the device, and
to adjust the heating of the material based on the airflow rate.

6. The device of claim 1, wherein the at least one capsule has a color associated with the type of the at least one capsule, and the control circuitry is further configured to perform the classification based on the color.

7. The device of claim 1, wherein the at least one capsule has a thermal emissivity associated with the type of the at least one capsule, and the control circuitry is further configured to perform the classification based on the thermal emissivity.

8. The device of claim 1, wherein the at least one capsule has an electrical resistance associated with the type of the at least one capsule, and the control circuitry is further configured to perform the classification based on the electrical resistance.

9. A device, comprising:
at least one capsule including
a material containing at least one active ingredient, and
a first covering layer and a second covering layer configured to cover the material, the first covering layer and the second covering layer opposing each other and being configured to direct an airflow into the first covering layer, through at least a portion of the material, and out of the second covering layer during an operational use of the at least one capsule, and
an internal heating element within the at least one capsule; and
control circuitry configured to perform a classification of a type of the at least one capsule and to implement a heating of the at least one capsule via the internal heating element based on the classification to at least partially vaporize the at least one active ingredient of the material,
the at least one capsule including at least one phase-change material associated with the type of the at least one capsule, the control circuitry being configured to perform the classification based on at least one first phase-change temperature of the at least one phase-change material.

10. The device of claim 9, wherein the at least one phase-change material includes a plurality of phase-change materials associated with the type of the at least one capsule, and the at least one first phase-change temperature includes a plurality of phase-change temperatures for the plurality of phase-change materials.

11. The device of claim 9, wherein the at least one phase-change material is configured to undergo a loss in quantity or phase-change property once heated to above the at least one first phase-change temperature, and the control circuitry is configured to not implement the heating of the at least one capsule when the loss in quantity or phase-change property of the at least one phase-change material is detected.

12. The device of claim 1, further comprising:
a vaporizing unit with a first housing, the vaporizing unit including the control circuitry, the vaporizing unit being configured to receive the at least one capsule.

13. The device of claim 12, wherein the control circuitry is configured to automatically perform the classification upon an insertion of the at least one capsule into the vaporizing unit.

14. The device of claim 12, further comprising:
a reloading unit with a second housing, the reloading unit including a power supply, the first housing being at least partially insertable into the second housing, the reloading unit being configured to selectively insert the at least one capsule into the vaporizing unit via an action of at least one of an electric motor or a pressing force on a capsule-loading button that is configured to cause an engagement plate to contact the at least one capsule and insert the at least one capsule into the vaporizing unit.

15. The device of claim 1, wherein the internal heating element includes a major body with at least one planar surface.

16. The device of claim 1, wherein the internal heating element includes a major body with a first planar surface and a second planar surface that oppose each other.

17. The device of claim 1, wherein the at least one capsule is planar in shape.

18. The device of claim 1, wherein the first covering layer and the second covering layer are opposing planar surfaces.

19. The device of claim 18, wherein the opposing planar surfaces span across a longitudinal length of the at least one capsule, the longitudinal length being greater than a width that spans between the opposing planar surfaces.

20. A device, comprising:
at least one capsule including
a material containing at least one active ingredient, and
a first covering layer and a second covering layer configured to cover the material, the first covering layer and the second covering layer opposing each other and being configured to direct an airflow into the first covering layer, through at least a portion of the material, and out of the second covering layer during an operational use of the at least one capsule, the first covering layer and the second covering layer each include a non-perforated sheet configured to be perforated to respectively define a first series of airflow paths and a second series of airflow paths on either side of the material prior to a heating of the at least one capsule, and
an internal heating element within the at least one capsule, the internal heating element directly contacting at least a portion of the material, the at least one capsule being planar in shape; and
a sensor configured to sense a temperature of at least one of the material or the at least one capsule; and
control circuitry operatively connected to at least the sensor and the internal heating element, the control circuitry being configured to automatically perform a classification of a type of the at least one capsule and to implement the heating of the at least one capsule via the internal heating element based on the classification to at least partially vaporize the at least one active ingredient of the material, the control circuitry being configured to perform the classification based on at least a detection of a pause in an increase in the temperature that is sensed by the sensor,
the first covering layer and the second covering layer being configured to direct the airflow into the at least one capsule into the first covering layer in a first direction, cause at least some of the airflow to be directed through the material in a second direction and exit the second covering layer in a third direction, the first direction and the third direction being parallel to each other, the second direction being substantially perpendicular to the first direction and the third direction, the first series of airflow paths and the second series of airflow paths being unaligned with each other.

21. The device of claim 1, wherein the internal heating element includes an internal mesh.

22. A device, comprising:
at least one capsule including
a material containing at least one active ingredient, and a first covering layer and a second covering layer configured to cover the material, the first covering layer and the second covering layer opposing each other and being configured to direct an airflow into the first covering layer, through at least a portion of the material, and out of the second covering layer during an operational use of the at least one capsule, and an internal heating element within the at least one capsule, the internal heating element directly contacting at least a portion of the material;

a sensor configured to sense a temperature of at least one of the material or the at least one capsule; and control circuitry operatively connected to at least the sensor and the internal heating element, the control circuitry being configured to automatically perform a classification of a type of the material and to implement a heating of the at least one capsule via the internal heating element based on the classification to at least partially vaporize the at least one active ingredient of the material, the control circuitry being configured to perform the classification based on at least a detection of a pause in an increase in the temperature that is sensed by the sensor.

* * * * *